United States Patent
Chetham et al.

(10) Patent No.: US 11,660,013 B2
(45) Date of Patent: May 30, 2023

(54) MONITORING SYSTEM

(71) Applicant: IMPEDIMED LIMITED, Pinkenba (AU)

(72) Inventors: Scott Chetham, Del Mar, CA (US); Leigh Cordwin Ward, Kenmore Hills (AU); Tim Essex, Clayfield (AU)

(73) Assignee: IMPEDIMED LIMITED, Pinkemba (AU)

( * ) Notice: Subject to any disclaimer, the term of this patent is extended or adjusted under 35 U.S.C. 154(b) by 762 days.

(21) Appl. No.: 15/482,347

(22) Filed: Apr. 7, 2017

(65) Prior Publication Data
US 2017/0209066 A1    Jul. 27, 2017

Related U.S. Application Data

(63) Continuation of application No. 11/993,219, filed as application No. PCT/AU2006/000924 on Jun. 30, 2006, now abandoned.

(Continued)

(30) Foreign Application Priority Data

| Jul. 1, 2005 | (AU) | ................................ | 2005903510 |
| Jul. 7, 2005 | (AU) | ................................ | 2005903603 |
| Aug. 23, 2005 | (AU) | ................................ | 2005904569 |

(51) Int. Cl.
*A61B 5/053*    (2021.01)
*A61B 5/0537*    (2021.01)
(Continued)

(52) U.S. Cl.
CPC .............. *A61B 5/053* (2013.01); *A61B 5/029* (2013.01); *A61B 5/0537* (2013.01); *A61B 5/061* (2013.01);
(Continued)

(58) Field of Classification Search
CPC .... A61B 5/053; A61B 5/0537; A61N 1/3686; A61N 1/3688
See application file for complete search history.

(56) References Cited

U.S. PATENT DOCUMENTS

| 3,316,896 A | 5/1967 | Thomasset |
| 3,851,641 A | 12/1974 | Toole et al. |

(Continued)

FOREIGN PATENT DOCUMENTS

| CA | 2231038 | 11/1999 |
| CA | 2638958 | 6/2000 |

(Continued)

OTHER PUBLICATIONS

Abdullah M. Z.; Simulation of an inverse problem in electrical impedance tomography using resistance electrical network analogues; International Journal of Electrical Engineering Education; vol. 36, No. 4, pp. 311-324; Oct. 1999.

(Continued)

*Primary Examiner* — Devin B Henson
*Assistant Examiner* — H. Q. Nguyen
(74) *Attorney, Agent, or Firm* — Knobbe, Martens, Olson & Bear, LLP

(57) ABSTRACT

A method of performing impedance measurements on a subject. The method includes using a processing system to determine at least one impedance measurement to be performed, and at one electrode arrangement associated with the determined measurement. A representation of the arrangement is displayed so the impedance measurement can be performed once the electrodes have been arranged in accordance with the displayed representation.

20 Claims, 27 Drawing Sheets

Related U.S. Application Data

(60) Provisional application No. 60/697,101, filed on Jul. 7, 2005, provisional application No. 60/697,100, filed on Jul. 7, 2005.

(51) Int. Cl.
    *A61B 5/00*            (2006.01)
    *A61B 5/06*            (2006.01)
    *A61B 5/029*          (2006.01)

(52) U.S. Cl.
    CPC ............ *A61B 5/063* (2013.01); *A61B 5/4842* (2013.01); *A61B 5/4878* (2013.01); *A61B 5/7278* (2013.01); *A61B 5/744* (2013.01); *A61B 2560/0271* (2013.01)

(56) References Cited

U.S. PATENT DOCUMENTS

| | | |
|---|---|---|
| 3,866,600 A | 2/1975 | Rey |
| 3,868,165 A | 2/1975 | Gonser |
| 3,871,359 A | 3/1975 | Pacela |
| 4,008,712 A | 2/1977 | Nyboer |
| 4,034,854 A | 7/1977 | Bevilacqua |
| 4,082,087 A | 4/1978 | Howson |
| 4,121,575 A | 10/1978 | Mills et al. |
| 4,144,878 A | 3/1979 | Wheeler |
| RE30,101 E | 9/1979 | Kubicek et al. |
| 4,169,463 A | 10/1979 | Piquard |
| 4,184,486 A | 1/1980 | Papa |
| 4,233,987 A | 11/1980 | Feingold |
| 4,291,708 A | 9/1981 | Frei et al. |
| 4,314,563 A | 2/1982 | Wheeler |
| 4,353,372 A | 10/1982 | Ayer |
| 4,365,634 A | 12/1982 | Bare et al. |
| 4,407,288 A | 10/1983 | Langer et al. |
| 4,407,300 A | 10/1983 | Davis |
| 4,450,527 A | 5/1984 | Sramek |
| 4,458,694 A | 7/1984 | Sollish et al. |
| 4,468,832 A | 9/1984 | Bai et al. |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,639 A | 10/1986 | Brown et al. |
| 4,638,807 A | 1/1987 | Ryder |
| 4,646,754 A | 3/1987 | Seale |
| 4,686,477 A | 8/1987 | Givens et al. |
| 4,688,580 A | 8/1987 | Ko et al. |
| 4,763,660 A | 8/1988 | Kroll et al. |
| 4,793,362 A | 12/1988 | Tedner |
| 4,832,608 A | 5/1989 | Kroll |
| 4,836,214 A | 6/1989 | Sramek |
| 4,890,630 A | 1/1990 | Kroll et al. |
| 4,895,163 A | 1/1990 | Libke et al. |
| 4,899,758 A | 2/1990 | Finkelstein et al. |
| 4,905,705 A | 3/1990 | Kizakevich et al. |
| 4,911,175 A | 3/1990 | Shizgal |
| 4,922,911 A | 5/1990 | Wada et al. |
| 4,924,875 A | 5/1990 | Chamoun |
| 4,942,880 A | 7/1990 | Slovák |
| 4,951,682 A | 8/1990 | Petre |
| 4,981,141 A | 1/1991 | Segalowitz |
| 5,020,541 A | 6/1991 | Marriott |
| 5,025,784 A | 6/1991 | Shao et al. |
| 5,063,937 A | 11/1991 | Ezenwa et al. |
| 5,078,134 A | 1/1992 | Heilman et al. |
| 5,086,781 A | 2/1992 | Bookspan |
| 5,101,828 A | 4/1992 | Welkowitz et al. |
| 5,143,079 A | 9/1992 | Frei et al. |
| 5,184,624 A | 2/1993 | Brown et al. |
| 5,197,479 A | 3/1993 | Hubelbank et al. |
| 5,199,432 A | 4/1993 | Quedens et al. |
| 5,233,982 A | 8/1993 | Kohl |
| 5,246,008 A | 9/1993 | Meuller |
| 5,272,624 A | 12/1993 | Gisser et al. |
| 5,280,429 A | 1/1994 | Whithers |
| 5,282,840 A | 2/1994 | Hudrlik |
| 5,284,142 A | 2/1994 | Goble et al. |
| 5,305,192 A | 4/1994 | Bonte et al. |
| 5,309,917 A | 5/1994 | Wang et al. |
| 5,311,878 A | 5/1994 | Brown et al. |
| 5,335,667 A | 8/1994 | Cha et al. |
| 5,351,697 A | 10/1994 | Cheney et al. |
| 5,353,802 A | 10/1994 | Ollmar |
| 5,372,141 A | 12/1994 | Gallup et al. |
| 5,381,333 A | 1/1995 | Isaacson et al. |
| 5,390,110 A | 2/1995 | Cheney et al. |
| 5,415,164 A | 5/1995 | Faupel |
| 5,421,345 A | 6/1995 | Lekholm et al. |
| 5,423,326 A | 6/1995 | Wang et al. |
| 5,427,113 A | 6/1995 | Hiroshi et al. |
| 5,449,000 A | 9/1995 | Libke et al. |
| 5,454,377 A | 10/1995 | Dzwonczyk et al. |
| 5,465,730 A | 11/1995 | Zadehoochak et al. |
| 5,469,859 A | 11/1995 | Tsoglin et al. |
| 5,503,157 A | 4/1996 | Sramek |
| 5,505,209 A | 4/1996 | Reining |
| 5,511,553 A | 4/1996 | Segalowitz |
| 5,526,808 A | 6/1996 | Kaminsky |
| 5,529,072 A | 6/1996 | Sramek |
| 5,544,662 A | 8/1996 | Saulnier et al. |
| 5,557,242 A | 9/1996 | Wetherell |
| 5,562,607 A | 10/1996 | Gyory |
| 5,575,929 A | 11/1996 | Yu et al. |
| 5,588,429 A | 12/1996 | Isaacson et al. |
| 5,611,351 A | 3/1997 | Sato et al. |
| 5,615,689 A | 4/1997 | Kotler |
| 5,626,146 A | 5/1997 | Barber et al. |
| 5,704,355 A | 1/1998 | Bridges |
| 5,730,136 A | 3/1998 | Laufer et al. |
| 5,732,710 A | 3/1998 | Rabinovich et al. |
| 5,735,284 A | 4/1998 | Tsoglin et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A | 9/1998 | Kun et al. |
| 5,810,742 A | 9/1998 | Pearlman |
| 5,876,353 A | 3/1999 | Riff |
| 5,919,142 A | 7/1999 | Boone et al. |
| 5,947,910 A | 9/1999 | Zimmet |
| 5,957,861 A | 9/1999 | Combs et al. |
| 5,964,703 A | 10/1999 | Goodman et al. |
| 5,994,956 A | 11/1999 | Concorso |
| 6,006,125 A | 12/1999 | Kelly et al. |
| 6,011,992 A | 1/2000 | Hubbard et al. |
| 6,015,389 A | 1/2000 | Brown |
| 6,018,677 A | 1/2000 | Vidrine et al. |
| 6,101,413 A | 8/2000 | Olson et al. |
| 6,115,626 A | 9/2000 | Whayne et al. |
| 6,122,544 A | 9/2000 | Organ |
| 6,125,297 A | 9/2000 | Siconolfi |
| 6,129,666 A | 10/2000 | DeLuca et al. |
| 6,142,949 A | 11/2000 | Ubby |
| 6,151,523 A | 11/2000 | Rosell Ferrer et al. |
| 6,167,300 A | 12/2000 | Cherepenin et al. |
| 6,173,003 B1 | 1/2001 | Whikehart et al. |
| 6,228,022 B1 | 5/2001 | Friesem et al. |
| 6,228,033 B1 | 5/2001 | Koobi |
| 6,233,473 B1 | 5/2001 | Shepherd et al. |
| 6,236,886 B1 | 5/2001 | Cherepenin et al. |
| 6,248,083 B1 | 6/2001 | Smith et al. |
| 6,253,100 B1 | 6/2001 | Zhdanov |
| 6,256,532 B1 | 7/2001 | Cha |
| 6,280,396 B1 | 8/2001 | Clark |
| 6,292,690 B1 | 9/2001 | Petrucelli et al. |
| 6,308,097 B1 | 10/2001 | Pearlman |
| 6,339,722 B1 | 1/2002 | Heethaar et al. |
| 6,354,996 B1 | 3/2002 | Drinan et al. |

(56) References Cited

U.S. PATENT DOCUMENTS

| | | |
|---|---|---|
| 6,376,023 B1 | 4/2002 | Mori |
| 6,432,045 B2 | 8/2002 | Lemperle et al. |
| 6,459,930 B1 | 10/2002 | Takehara et al. |
| 6,469,732 B1 | 10/2002 | Chang et al. |
| 6,472,888 B2 | 10/2002 | Oguma et al. |
| 6,496,725 B2 | 12/2002 | Kamada et al. |
| 6,497,659 B1 | 12/2002 | Rafert |
| 6,501,984 B1 | 12/2002 | Church et al. |
| 6,511,438 B2 | 1/2003 | Bernstein et al. |
| 6,512,949 B1 | 1/2003 | Combs et al. |
| 6,516,218 B1 | 2/2003 | Cheng et al. |
| 6,522,910 B1 | 2/2003 | Gregory |
| 6,532,384 B1 | 3/2003 | Fukuda |
| 6,551,252 B2 | 4/2003 | Sackner et al. |
| 6,556,001 B1 | 4/2003 | Wiegand et al. |
| 6,560,480 B1 | 5/2003 | Nachaliel et al. |
| 6,561,986 B2 | 5/2003 | Baura et al. |
| 6,564,079 B1 | 5/2003 | Cory et al. |
| 6,569,160 B1 | 5/2003 | Goldin et al. |
| 6,584,348 B2 | 6/2003 | Glukhovsky |
| 6,602,201 B1 | 8/2003 | Hepp et al. |
| 6,615,077 B1 | 9/2003 | Zhu et al. |
| 6,618,616 B2 | 9/2003 | Iijima et al. |
| 6,623,312 B2 | 9/2003 | Merry et al. |
| 6,625,487 B2 | 9/2003 | Herleikson |
| 6,631,292 B1 | 10/2003 | Liedtk |
| 6,633,777 B2 | 10/2003 | Szopinski |
| 6,636,754 B1 | 10/2003 | Baura et al. |
| 6,643,543 B2 | 11/2003 | Takehara et al. |
| 6,658,296 B1 | 12/2003 | Wong et al. |
| 6,714,813 B2 | 3/2004 | Ishigooka et al. |
| 6,714,814 B2 | 3/2004 | Yamada et al. |
| 6,723,049 B2 | 4/2004 | Skladnev et al. |
| 6,724,200 B2 | 4/2004 | Fukuda |
| 6,725,089 B2 | 4/2004 | Komatsu et al. |
| 6,760,617 B2 | 7/2004 | Ward et al. |
| 6,763,263 B2 | 7/2004 | Gregory et al. |
| 6,768,921 B2 | 7/2004 | Organ et al. |
| 6,788,966 B2 | 9/2004 | Kenan et al. |
| 6,790,178 B1 | 9/2004 | Mault et al. |
| 6,807,443 B2 | 10/2004 | Keren |
| 6,829,501 B2 | 12/2004 | Nielsen et al. |
| 6,829,503 B2 | 12/2004 | Alt |
| 6,840,907 B1 | 1/2005 | Brydon |
| 6,845,264 B1 | 1/2005 | Skladnev et al. |
| 6,870,109 B1 | 3/2005 | Villarreal |
| 6,875,176 B2 | 4/2005 | Mourad et al. |
| 6,906,533 B1 | 6/2005 | Yoshida |
| 6,922,586 B2 | 7/2005 | Davies |
| 6,936,012 B2 | 8/2005 | Wells |
| 6,940,286 B2 | 9/2005 | Wang et al. |
| RE38,879 E | 11/2005 | Goodman et al. |
| 6,980,852 B2 | 12/2005 | Jersey-Willuhn et al. |
| 6,980,853 B2 | 12/2005 | Miyoshi et al. |
| 7,065,399 B2 | 6/2006 | Nakada |
| 7,079,889 B2 | 7/2006 | Nakada |
| 7,096,061 B2 | 8/2006 | Arad |
| 7,122,012 B2 | 10/2006 | Bouton et al. |
| 7,130,680 B2 | 10/2006 | Kodama et al. |
| 7,132,611 B2 | 11/2006 | Gregaard et al. |
| 7,148,701 B2 | 12/2006 | Park et al. |
| 7,149,573 B2 | 12/2006 | Wang |
| 7,169,107 B2 | 1/2007 | Jersey-Willuhn et al. |
| 7,184,820 B2 | 2/2007 | Jersey-Willuhn et al. |
| 7,184,821 B2 | 2/2007 | Belalcazar et al. |
| 7,186,220 B2 | 3/2007 | Stahmann et al. |
| 7,206,630 B1 | 4/2007 | Tarler |
| 7,212,852 B2 | 5/2007 | Smith et al. |
| 7,233,823 B2 | 6/2007 | Simond et al. |
| 7,251,524 B1 | 7/2007 | Hepp et al. |
| 7,288,943 B2 | 10/2007 | Matthiessen et al. |
| D557,809 S | 12/2007 | Neverov et al. |
| 7,313,435 B2 | 12/2007 | Nakada et al. |
| 7,317,161 B2 | 1/2008 | Fukuda |
| 7,336,992 B2 | 2/2008 | Shiokawa |
| 7,440,796 B2 | 10/2008 | Woo et al. |
| 7,457,660 B2 | 11/2008 | Smith et al. |
| 7,477,937 B2 | 1/2009 | Iijima et al. |
| 7,496,450 B2 | 2/2009 | Ortiz Aleman et al. |
| 7,499,745 B2 | 3/2009 | Littrup et al. |
| D603,051 S | 10/2009 | Causevic et al. |
| 7,603,158 B2 | 10/2009 | Nachman |
| 7,603,171 B2 | 10/2009 | Eror et al. |
| 7,628,761 B2 | 12/2009 | Gozani et al. |
| 7,630,763 B2 * | 12/2009 | Kwok .................. A61B 5/053 607/27 |
| 7,638,341 B2 | 12/2009 | Rubinsky et al. |
| 7,657,292 B2 | 2/2010 | Baker et al. |
| 7,660,617 B2 | 2/2010 | Davis |
| 7,706,872 B2 | 4/2010 | Min et al. |
| 7,711,418 B2 | 5/2010 | Garber et al. |
| 7,729,756 B2 | 6/2010 | Mertelmeier et al. |
| 7,733,224 B2 | 6/2010 | Tran |
| 7,749,013 B2 | 7/2010 | Sato et al. |
| 7,860,557 B2 | 12/2010 | Istvan et al. |
| D641,886 S | 7/2011 | Causevic et al. |
| D647,208 S | 10/2011 | Rothman et al. |
| 8,233,617 B2 | 7/2012 | Johnson et al. |
| 8,233,974 B2 | 7/2012 | Ward et al. |
| D669,186 S | 10/2012 | Gozani |
| D669,187 S | 10/2012 | Gozani |
| D674,096 S | 1/2013 | Gaw et al. |
| 8,467,865 B2 | 6/2013 | Gregory et al. |
| D718,458 S | 11/2014 | Vosch et al. |
| D719,660 S | 12/2014 | Vosch et al. |
| D728,801 S | 5/2015 | Machon et al. |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0025139 A1 | 9/2001 | Pearlman |
| 2001/0051774 A1 | 12/2001 | Littrup et al. |
| 2002/0072686 A1 | 1/2002 | Hoey et al. |
| 2002/0020138 A1 | 2/2002 | Walker et al. |
| 2002/0022773 A1 | 2/2002 | Drinan et al. |
| 2002/0022787 A1 | 2/2002 | Takehara et al. |
| 2002/0079910 A1 | 6/2002 | Fukuda |
| 2002/0093991 A1 | 7/2002 | Plangger |
| 2002/0093992 A1 | 7/2002 | Plangger |
| 2002/0106681 A1 | 8/2002 | Wexler et al. |
| 2002/0109621 A1 | 8/2002 | Khair et al. |
| 2002/0111559 A1 | 8/2002 | Kurata et al. |
| 2002/0123694 A1 | 9/2002 | Organ et al. |
| 2002/0138019 A1 | 9/2002 | Wexler et al. |
| 2002/0161311 A1 | 10/2002 | Ward et al. |
| 2002/0193689 A1 | 12/2002 | Bernstein et al. |
| 2002/0194419 A1 | 12/2002 | Rajput et al. |
| 2003/0004403 A1 | 1/2003 | Drinan et al. |
| 2003/0009111 A1 | 1/2003 | Cory et al. |
| 2003/0023184 A1 | 1/2003 | Pitts/Crick et al. |
| 2003/0028221 A1 | 2/2003 | Zhu et al. |
| 2003/0036713 A1 | 2/2003 | Bouton et al. |
| 2003/0050570 A1 | 3/2003 | Kodama et al. |
| 2003/0073916 A1 | 4/2003 | Yonce |
| 2003/0105410 A1 | 6/2003 | Pearlman |
| 2003/0105411 A1 | 6/2003 | Smallwood et al. |
| 2003/0120170 A1 | 6/2003 | Zhu et al. |
| 2003/0120182 A1 | 6/2003 | Wilkinson et al. |
| 2003/0173976 A1 | 9/2003 | Wiegand et al. |
| 2003/0176808 A1 | 9/2003 | Masuo |
| 2003/0216661 A1 | 11/2003 | Davies |
| 2003/0216664 A1 | 11/2003 | Suarez |
| 2004/0015095 A1 | 1/2004 | Li et al. |
| 2004/0019292 A1 | 1/2004 | Drinan et al. |
| 2004/0059220 A1 | 3/2004 | Mourad et al. |
| 2004/0059242 A1 * | 3/2004 | Masuo ................ A61B 5/0537 600/547 |
| 2004/0073127 A1 | 4/2004 | Istvan et al. |
| 2004/0073130 A1 | 4/2004 | Bohm et al. |
| 2004/0077944 A1 | 4/2004 | Steinberg et al. |
| 2004/0092841 A1 * | 5/2004 | Singer .................. A61B 5/053 600/547 |
| 2004/0116819 A1 | 6/2004 | Alt |
| 2004/0127793 A1 | 7/2004 | Mendlein et al. |
| 2004/0158167 A1 | 8/2004 | Smith et al. |

(56) References Cited

U.S. PATENT DOCUMENTS

| | | |
|---|---|---|
| 2004/0167423 A1 | 8/2004 | Pillon et al. |
| 2004/0171961 A1 | 9/2004 | Smith et al. |
| 2004/0181163 A1 | 9/2004 | Acumen |
| 2004/0181164 A1 | 9/2004 | Smith et al. |
| 2004/0186392 A1 | 9/2004 | Ward et al. |
| 2004/0210150 A1 | 10/2004 | Virtanen |
| 2004/0210158 A1 | 10/2004 | Organ et al. |
| 2004/0220632 A1 | 11/2004 | Burnes |
| 2004/0234113 A1 | 11/2004 | Miga |
| 2004/0236202 A1 | 11/2004 | Burton |
| 2004/0242987 A1 | 12/2004 | Liew et al. |
| 2004/0242989 A1 | 12/2004 | Zhu et al. |
| 2004/0243018 A1 | 12/2004 | Organ et al. |
| 2004/0252870 A1 | 12/2004 | Reeves et al. |
| 2004/0253652 A1 | 12/2004 | Davies |
| 2004/0260167 A1 | 12/2004 | Leonhardt |
| 2004/0267333 A1 | 12/2004 | Kronberg |
| 2004/0267344 A1 | 12/2004 | Stett et al. |
| 2005/0039763 A1 | 2/2005 | Kraemer et al. |
| 2005/0049474 A1 | 3/2005 | Kellogg et al. |
| 2005/0080460 A1 | 4/2005 | Wang et al. |
| 2005/0085743 A1 | 4/2005 | Hacker et al. |
| 2005/0098343 A1 | 5/2005 | Fukuda |
| 2005/0101875 A1 | 5/2005 | Semler et al. |
| 2005/0107719 A1 | 5/2005 | Arad et al. |
| 2005/0113704 A1 | 5/2005 | Lawson et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177061 A1 | 8/2005 | Alanen et al. |
| 2005/0177062 A1 | 8/2005 | Skrabal et al. |
| 2005/0192488 A1 | 9/2005 | Bryenton et al. |
| 2005/0201598 A1 | 9/2005 | Harel et al. |
| 2005/0203435 A1 | 9/2005 | Nakada |
| 2005/0203436 A1 | 9/2005 | Davies |
| 2005/0215918 A1 | 9/2005 | Frantz |
| 2005/0228309 A1 | 10/2005 | Fisher et al. |
| 2005/0251062 A1 | 11/2005 | Choi et al. |
| 2005/0261743 A1 | 11/2005 | Kroll |
| 2005/0270051 A1 | 12/2005 | Yee et al. |
| 2005/0283091 A1 | 12/2005 | Kink et al. |
| 2006/0004300 A1 | 1/2006 | Kennedy |
| 2006/0025701 A1 | 2/2006 | Kasahara |
| 2006/0041280 A1 | 2/2006 | Stahmann et al. |
| 2006/0047189 A1 | 3/2006 | Takehara |
| 2006/0052678 A1 | 3/2006 | Drinan |
| 2006/0064029 A1 | 3/2006 | Arad (Abboud) |
| 2006/0070623 A1 | 4/2006 | Wilkinson et al. |
| 2006/0085048 A1 | 4/2006 | Cory et al. |
| 2006/0085049 A1* | 4/2006 | Cory .................. A61B 5/0536 607/48 |
| 2006/0100532 A1 | 5/2006 | Bae et al. |
| 2006/0111652 A1 | 5/2006 | McLeod |
| 2006/0116599 A1 | 6/2006 | Davis |
| 2006/0122523 A1 | 6/2006 | Bonmassar et al. |
| 2006/0122540 A1 | 6/2006 | Zhu et al. |
| 2006/0135886 A1 | 6/2006 | Lippert et al. |
| 2006/0184060 A1 | 8/2006 | Belalcazar |
| 2006/0197509 A1 | 9/2006 | Kanamori et al. |
| 2006/0200033 A1 | 9/2006 | Keren et al. |
| 2006/0224079 A1 | 10/2006 | Washchuck |
| 2006/0224080 A1 | 10/2006 | Oku et al. |
| 2006/0241512 A1* | 10/2006 | Kwok .................. A61N 1/3686 600/547 |
| 2006/0241513 A1 | 10/2006 | Hatlestad et al. |
| 2006/0241719 A1 | 10/2006 | Foster et al. |
| 2006/0247543 A1 | 11/2006 | Cornish et al. |
| 2006/0252670 A1 | 11/2006 | Fiorucci et al. |
| 2006/0253016 A1 | 11/2006 | Baker et al. |
| 2006/0258952 A1 | 11/2006 | Stahmann et al. |
| 2006/0264775 A1 | 11/2006 | Mills et al. |
| 2006/0264776 A1 | 11/2006 | Stahmann et al. |
| 2006/0270942 A1 | 11/2006 | McAdams |
| 2007/0007975 A1 | 1/2007 | Hawkins et al. |
| 2007/0010758 A1 | 1/2007 | Mattiessen et al. |
| 2007/0024310 A1 | 2/2007 | Tokuno et al. |
| 2007/0027402 A1 | 2/2007 | Levin et al. |
| 2007/0043303 A1 | 2/2007 | Osypka et al. |
| 2007/0049993 A1 | 3/2007 | Hofmann et al. |
| 2007/0087703 A1 | 4/2007 | Li et al. |
| 2007/0088227 A1 | 4/2007 | Nishimura |
| 2007/0106342 A1 | 5/2007 | Schumann |
| 2007/0118027 A1 | 5/2007 | Baker et al. |
| 2007/0156061 A1 | 7/2007 | Hess |
| 2007/0188219 A1 | 8/2007 | Segarra |
| 2007/0246046 A1 | 10/2007 | Teschner et al. |
| 2007/0270707 A1 | 11/2007 | Belalcazar |
| 2008/0001608 A1 | 1/2008 | Saulnier |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0009759 A1 | 1/2008 | Chetham |
| 2008/0027350 A1 | 1/2008 | Webler |
| 2008/0039700 A1 | 2/2008 | Drinan et al. |
| 2008/0048786 A1 | 2/2008 | Feldkamp et al. |
| 2008/0051643 A1 | 2/2008 | Park et al. |
| 2008/0064981 A1 | 3/2008 | Gregory |
| 2008/0091114 A1 | 4/2008 | Min et al. |
| 2008/0139957 A1 | 6/2008 | Hubbard et al. |
| 2008/0183098 A1 | 7/2008 | Denison et al. |
| 2008/0188757 A1 | 8/2008 | Rovira et al. |
| 2008/0200802 A1 | 8/2008 | Bhavaraju et al. |
| 2008/0205717 A1 | 8/2008 | Reeves et al. |
| 2008/0221411 A1 | 9/2008 | Hausmann et al. |
| 2008/0247502 A1 | 10/2008 | Liao |
| 2008/0252304 A1 | 10/2008 | Woo et al. |
| 2008/0262375 A1 | 10/2008 | Brown et al. |
| 2008/0287823 A1 | 11/2008 | Chetham |
| 2008/0306400 A1 | 12/2008 | Takehara |
| 2008/0306402 A1 | 12/2008 | Singer |
| 2008/0319336 A1 | 12/2008 | Ward et al. |
| 2009/0018432 A1 | 1/2009 | He |
| 2009/0043222 A1 | 2/2009 | Chetham |
| 2009/0054952 A1 | 2/2009 | Glukhovsky et al. |
| 2009/0069708 A1 | 3/2009 | Hatlestad et al. |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0076410 A1 | 3/2009 | Libbus et al. |
| 2009/0082679 A1 | 3/2009 | Chetham |
| 2009/0084674 A1 | 4/2009 | Holzhacker et al. |
| 2009/0093730 A1 | 4/2009 | Grassl |
| 2009/0105555 A1 | 4/2009 | Dacso et al. |
| 2009/0143663 A1 | 6/2009 | Chetham |
| 2009/0177099 A1 | 7/2009 | Smith et al. |
| 2009/0209828 A1 | 8/2009 | Musin |
| 2009/0209872 A1 | 8/2009 | Pop |
| 2009/0216140 A1 | 8/2009 | Skrabal |
| 2009/0216148 A1 | 8/2009 | Freed et al. |
| 2009/0234244 A1 | 9/2009 | Tanaka |
| 2009/0240163 A1 | 9/2009 | Webler |
| 2009/0264727 A1 | 10/2009 | Markowitz |
| 2009/0264745 A1 | 10/2009 | Markowitz et al. |
| 2009/0264776 A1 | 10/2009 | Vardy |
| 2009/0264791 A1 | 10/2009 | Gregory et al. |
| 2009/0275854 A1 | 11/2009 | Zielinski et al. |
| 2009/0275855 A1 | 11/2009 | Zielinski et al. |
| 2009/0287102 A1 | 11/2009 | Ward |
| 2009/0306535 A1 | 12/2009 | Davies et al. |
| 2009/0318778 A1 | 12/2009 | Dacso et al. |
| 2009/0326408 A1 | 12/2009 | Moon |
| 2010/0007357 A1 | 1/2010 | Ammari et al. |
| 2010/0049077 A1 | 2/2010 | Sadleir et al. |
| 2010/0056881 A1 | 3/2010 | Libbus et al. |
| 2010/0094160 A1 | 4/2010 | Eror et al. |
| 2010/0100003 A1 | 4/2010 | Chetham et al. |
| 2010/0100146 A1 | 4/2010 | Blomqvist |
| 2010/0106046 A1 | 4/2010 | Shochat |
| 2010/0152605 A1 | 6/2010 | Ward |
| 2010/0168530 A1 | 7/2010 | Chetham et al. |
| 2010/0191141 A1 | 7/2010 | Aberg |
| 2010/0228143 A1 | 9/2010 | Teschner et al. |
| 2011/0025348 A1 | 2/2011 | Chetham et al. |
| 2011/0054343 A1 | 3/2011 | Chetham et al. |

(56) References Cited

U.S. PATENT DOCUMENTS

| | | |
|---|---|---|
| 2011/0060239 A1 | 3/2011 | Gaw |
| 2011/0087129 A1 | 4/2011 | Chetham et al. |
| 2011/0118619 A1 | 5/2011 | Burton et al. |
| 2011/0190655 A1 | 8/2011 | Moissl et al. |
| 2011/0251513 A1 | 10/2011 | Chetham et al. |

FOREIGN PATENT DOCUMENTS

| | | |
|---|---|---|
| CA | 2613524 | 1/2007 |
| CA | 2615845 | 1/2007 |
| CN | 1180513 | 5/1998 |
| CN | 1236597 | 12/1999 |
| CN | 1329875 | 1/2002 |
| DE | 2912349 | 10/1980 |
| EP | 0249823 | 12/1987 |
| EP | 349043 | 3/1990 |
| EP | 0357309 | 3/1990 |
| EP | 377887 | 7/1990 |
| EP | 581073 | 2/1994 |
| EP | 339471 | 3/1997 |
| EP | 865763 | 9/1998 |
| EP | 0869360 | 10/1998 |
| EP | 1078597 | 2/2001 |
| EP | 1080686 | 3/2001 |
| EP | 1112715 | 4/2001 |
| EP | 1112715 | 7/2001 |
| EP | 1146344 | 10/2001 |
| EP | 1114610 | 11/2001 |
| EP | 1177760 | 2/2002 |
| EP | 1219937 | 7/2002 |
| EP | 1238630 | 9/2002 |
| EP | 1247487 | 10/2002 |
| EP | 1329190 | 7/2003 |
| EP | 1338246 | 8/2003 |
| EP | 1080686 | 3/2004 |
| EP | 1452131 | 9/2004 |
| EP | 1553871 | 7/2005 |
| EP | 1118308 | 11/2005 |
| EP | 1629772 | 3/2006 |
| EP | 1247487 | 1/2008 |
| EP | 1903938 | 4/2008 |
| EP | 1909642 | 4/2008 |
| EP | 1948017 | 7/2008 |
| EP | 1353595 | 8/2008 |
| FR | 2486386 | 1/1982 |
| FR | 2748928 | 11/1997 |
| GB | 1441622 | 7/1976 |
| GB | 2131558 | 6/1984 |
| GB | 2260416 | 4/1993 |
| GB | 2426824 | 12/2006 |
| JP | 6-74103 | 10/1994 |
| JP | 8191808 | 7/1996 |
| JP | 09051884 | 2/1997 |
| JP | 9220209 | 8/1997 |
| JP | 10000185 | 1/1998 |
| JP | 10014898 | 1/1998 |
| JP | 10014899 | 2/1998 |
| JP | 11070090 | 3/1999 |
| JP | 11-513592 | 11/1999 |
| JP | 2000107138 | 4/2000 |
| JP | 2000139867 | 5/2000 |
| JP | 2001037735 | 2/2001 |
| JP | 2001061804 | 3/2001 |
| JP | 2001-204707 | 7/2001 |
| JP | 2001224568 | 8/2001 |
| JP | 2001-245866 | 9/2001 |
| JP | 2001321352 | 11/2001 |
| JP | 2002502274 | 1/2002 |
| JP | 2002238870 | 8/2002 |
| JP | 202330938 | 11/2002 |
| JP | 2002350477 | 12/2002 |
| JP | 2003502092 | 1/2003 |
| JP | 2003075487 | 3/2003 |
| JP | 2003-116803 | 4/2003 |
| JP | 2003116805 | 4/2003 |
| JP | 2003230547 | 8/2003 |
| JP | 200461251 | 2/2004 |
| JP | 2006501892 | 1/2006 |
| JP | 2008502382 | 1/2008 |
| JP | 2008022995 | 7/2008 |
| JP | 2010526604 | 8/2010 |
| RU | 2112416 | 6/1998 |
| WO | WO 1991-019454 | 12/1991 |
| WO | WO 1993/18821 | 9/1993 |
| WO | WO 1993-018821 | 9/1993 |
| WO | WO 94/01040 | 1/1994 |
| WO | WO 1994-010922 | 5/1994 |
| WO | WO 1996-001586 | 1/1996 |
| WO | WO 1996/01586 | 1/1996 |
| WO | WO 1996/012439 | 5/1996 |
| WO | WO 1996/032652 | 10/1996 |
| WO | WO 1997/011638 | 4/1997 |
| WO | WO 1997-011638 | 4/1997 |
| WO | WO 1997/014358 | 4/1997 |
| WO | WO 1997-024156 | 7/1997 |
| WO | WO 1998-006328 | 2/1998 |
| WO | WO 1998/06328 | 2/1998 |
| WO | WO 98/12983 | 4/1998 |
| WO | WO 1998/023204 | 6/1998 |
| WO | WO 1998/033553 | 8/1998 |
| WO | WO 1998/033553 | 8/1998 |
| WO | WO 1988/007392 | 10/1998 |
| WO | WO 1998-051211 | 11/1998 |
| WO | WO 1999-042034 | 8/1999 |
| WO | WO 1999-048422 | 9/1999 |
| WO | WO 2000-019886 | 4/2000 |
| WO | WO 2000/040955 | 7/2000 |
| WO | WO 2000-078213 | 12/2000 |
| WO | WO 2000/079255 | 12/2000 |
| WO | WO 2001-027605 | 4/2001 |
| WO | WO 2001/050954 | 7/2001 |
| WO | WO 2001-052733 | 7/2001 |
| WO | WO 2001/067098 | 9/2001 |
| WO | WO 2002-053028 | 7/2002 |
| WO | WO 2002/062214 | 8/2002 |
| WO | WO 2004/000115 | 12/2003 |
| WO | WO 2004/002301 | 1/2004 |
| WO | WO 2004/006660 | 1/2004 |
| WO | WO 2004-021880 | 3/2004 |
| WO | WO 2004/026136 | 4/2004 |
| WO | WO 2004-030535 | 4/2004 |
| WO | WO 2004/032738 | 4/2004 |
| WO | WO 2004-043252 | 5/2004 |
| WO | WO 2004/047635 | 6/2004 |
| WO | WO 2004/047636 | 6/2004 |
| WO | WO 2004/047638 | 6/2004 |
| WO | WO 2004/047638 | 6/2004 |
| WO | WO 2004/083804 | 9/2004 |
| WO | WO 2004/084087 | 9/2004 |
| WO | WO 2004/084723 | 10/2004 |
| WO | WO 2004/098389 | 11/2004 |
| WO | WO 2004/112563 | 12/2004 |
| WO | WO 2005/018432 | 3/2005 |
| WO | WO 2005/027717 | 3/2005 |
| WO | WO 2005-051163 | 6/2005 |
| WO | WO 2005/051194 | 6/2005 |
| WO | WO 2005-122881 | 12/2005 |
| WO | WO 2005/122888 | 12/2005 |
| WO | WO 2006-045051 | 4/2006 |
| WO | WO 2006-056074 | 6/2006 |
| WO | WO 2006/129108 | 12/2006 |
| WO | WO 2006/129116 | 12/2006 |
| WO | WO 2007/002991 | 1/2007 |
| WO | WO 2007/002992 | 1/2007 |
| WO | WO 2007-002993 | 1/2007 |
| WO | WO 2007/009183 | 1/2007 |
| WO | WO 2007/041783 | 4/2007 |
| WO | WO 2007/045006 | 4/2007 |
| WO | WO 2007-056493 | 5/2007 |
| WO | WO 2007-070997 | 6/2007 |
| WO | WO 2007/105996 | 9/2007 |
| WO | WO 2007-105996 | 9/2007 |
| WO | WO 2007-128952 | 11/2007 |
| WO | WO 2008-011716 | 1/2008 |

(56) References Cited

FOREIGN PATENT DOCUMENTS

| WO | WO 2008/064426 | 6/2008 |
|---|---|---|
| WO | WO 2008-054426 | 8/2008 |
| WO | WO 2008-119166 | 10/2008 |
| WO | WO 2008/119166 | 10/2008 |
| WO | WO 2008-138062 | 11/2008 |
| WO | WO 2008/138062 | 11/2008 |
| WO | WO 2008/149125 | 12/2008 |
| WO | WO 2009-018620 | 2/2009 |
| WO | WO 2009-027812 | 3/2009 |
| WO | WO 2009/036369 | 3/2009 |
| WO | WO 2009-068961 | 6/2009 |
| WO | WO 2009/100491 | 8/2009 |
| WO | WO 2009-112965 | 9/2009 |
| WO | WO 2010-003162 | 1/2010 |
| WO | WO 2010-029465 | 3/2010 |
| WO | WO 2010-069023 | 6/2010 |
| WO | WO 2010-076719 | 7/2010 |
| WO | WO 2011/022068 | 2/2011 |
| WO | WO 2011/050393 | 5/2011 |
| WO | WO 2011/075769 | 6/2011 |

OTHER PUBLICATIONS

Al-Hatib, F.; Patient Instrument connection errors in bioelectrical impedance measurement; Physiological Measurement; vol. 19, No. 2, pp. 285-296; May 2, 1998.

Bella, et al., Relations Of Left Ventricular Mass To Fat-Free And Adipose Body Mass: The Strong Heart Study, (1998) Circulation, vol. 98, pp. 2538-2544.

Bernstein; A New Stroke Volume Equation for Thoracic Electrical Bio Impedance; Critical Care Medicine; vol. 14, pp. 904-909; 1986.

Blad et al.; Impedance Spectra of Tumour Tissue in Tomparison with Normal Tissue; A Possible Clinical Application for Electrical Impedance Tomography; Physiological Measurement; vol. 17, pp. A105-A115; 1996.

Boulier, A. et al.; Fat-Free Mass Estimation By Two Electrode Impedance Method; American Journal of Clinical Nutrition; vol. 52, pp. 581-585; 1990.

Bracco, D. et al., Bedside determination of fluid accumulation after cardiac surgery using segmental bioelectrical impedance, Critical Care Medicine, vol. 26, No. 6, pp. 1065-1070, 1998.

Chaudary, S.S. et al.; Dielectric Properties of Normal & Malignant Human Breast Tissues at Radiowave and Microwave Frequencies; Indian Journal of Biochemistry & Biophysics; vol. 21, No. 1, pp. 76-79; 1984.

Chiolero, R.L. et al.; Assessment of changes in body water by bioimpedance in acutely ill surgical patients; Intensive Care Medicine; vol. 18, pp. 322-326; 1992.

Chumlea et al.; Bioelectrical Impedance and Body Composition: Present Status and Future Directions; Nutrition Reviews; vol. 52, No. 4, pp. 123-131; 1994.

International Search Report and Written Opinion of the International Searching Authority issued in PCT/AU2006/000922 dated Oct. 10, 2006.

International Search Report and Written Opinion of the International Searching Authority issued in PCT/AU2006/000922 dated Oct. 13, 2006.

International Search Report and Written Opinion of the International Searching Authority issued in PCT/AU2006/000924 dated Oct. 5, 2006.

International Search Report and Written Opinion of the International Searching Authority issued in PCT/AU2006/001057 dated Oct. 25, 2006.

International Search Report and Written Opinion of the International Searching Authority issued in PCT/AU2008/000034 dated Mar. 17, 2008.

International Search Report and Written Opinion of the International Searching Authority issued in PCT/AU2008/000588 dated Aug. 13, 2008.

International Search Report and Written Opinion of the International Searching Authority issued in PCT/AU2008/001521 dated Jan. 15, 2009.

International Search Report and Written Opinion of the International Searching Authority issued in PCT/AU2009/000163 dated Apr. 16, 2009.

International Search Report and Written Opinion of the International Searching Authority issued in PCT/CA2008/000588 dated Aug. 13, 2008.

Cornish, B.H. et al.; Alteration of the extracellular and total body water volumes measured by multiple frequency bioelectrical impedance analysis; Nutrition Research; vol. 14, No. 5, pp. 717-727; 1994.

Cornish, B.H. et al.; Bioelectrical impedance for monitoring the efficacy of lymphoedema treatment programmes; Breast Cancer Research and Treatment; vol. 38, pp. 169-176; 1996.

Cornish, B.H. et al.; Data analysis in multiple-frequency bioelectrical impedance analysis; Physiological Measurement; vol. 19, No. 2, pp. 275-283; May 1, 1998.

Cornish, B.H. et al.; Early diagnosis of lymphedema using multiple frequency bioimpedance; Lymphology; vol. 34, pp. 2-11; Mar. 2001.

Cornish, B.H. et al.; Early diagnosis of lymphoedema in postsurgery breast cancer patients; Annals New York Academy of Sciences; pp. 571-575; May 2000.

Cornish, B.H. et al.; Quantification of Lymphoedema using Multi-frequency Bioimpedance; Applied Radiation and Isotopes; vol. 49, No. 5/6, pp. 651-652; 1998.

Cornish, et al., "A New Technique for the Quantification of Peripheral Edema With Application in Both Unilateral and Bilateral Cases" Angiology, 2002, pp. 41-47, vol. 53, No. 1.

Cornish, et al., "Optimizing Electrode Sites for Segmental Bioimpedance Measurements" Physiological Measurement, Institute of Physics, 1999, pp. 241-250, vol. 20, No. 3.

De Lorenzo et al.; Determination of Intracellular Water by Multifrequency Bioelectrical Impedance; Ann. Nutr. Metab.; vol. 39, pp. 177-184; 1995.

De Luca, F. et al., Use of low-frequency electrical impedance measurements to determine phospoholipid content in amniotic fluid; Physics in Medicine and Biology, vol. 41, pp. 1863-1869, 1996.

Deurenberg, P. et al., Multi-frequency bioelectrical impedance: a comparison between the Cole-Cole modelling and Hanai equations with the classically impedance index approach, Annals of Human Biology, vol. 23, No. 1, pp. 31-40, 1996.

Dines K.A. et al.; Analysis of electrical conductivity imaging; Geophysics; vol. 46, No. 7, pp. 1025-1036; Jul. 1981.

Edwards, L.S.; A Modified Pseudosection for Resistivity and IP; Geophysics; vol. 42, No. 5, pp. 1020-1036; 1977.

Ellis, K.J. et al; Human hydrometry: comparison of multifrequency bioelectrical impedance with 2H2O and bromine dilution; Journal of Applied Physiology; vol. 85, No. 3, pp. 1056-1062; 1998.

Ezenwa, B.N. et al.; Multiple Frequency System for Body Composition Measurement; Proceedings of the Annual International Conference of the Engineering in Medicine and Biology Society; vol. 15; pp. 1020-1021; 1993.

Fenech, et al., "Extracellular and Intracellular Volume Variations During Postural Change Measured by Segmental and Wrist-Ankle Bioimpedance Spectroscopy" IEEE Transactions On Biomedical Engineering, IEEE Service Center, 2004, pp. 166-175, vol. 51, No. 1.

Forslund, A.H. et al.; Evaluation of modified multicompartment models to calculate body composition in healthy males; American Journal of Clinical Nutrition; vol. 63, pp. 856-862; 1996.

Gersing, E., Impedance spectroscopy on living tissue for determination of the state of Organs; Bioelectrochemistry and Bioenergetics; vol. 45, pp. 145-149; 1998.

Gerth, W.A. et al., A computer-based bioelectrical impedence spectroscopic system for noninvasive assessment of Compartment fluid destribution; Third Annual IEEE Symposium on Computer Based Medical System, Jun. 3-6, 1990, University of NC. At Chapel Hill; pp. 446-453; Jun. 1990.

(56) References Cited

OTHER PUBLICATIONS

Golden, et al., "Assessment of Peripheral Hemodynmics Using Impedence Plethysmogrphy" Physical Therapy , 1986, pp. 1544-1547, vol. 66, No. 10.
Gudivaka R. et al; Single and multifrequency models for bioelectrical impedence analysis of body water compartments; Applied Physiology; vol. 87, Issue 3, pp. 1087-1096; 1999.
Hansen, E.; On the Influence of Shape and Variations in Conductivity of the Sample on Four-Point Measurements; Applied Scientific Research; Section B; vol. 8, Issue 1, pp. 93-104 1960.
Iacobellis, G., et al. Influence Of Excess Fat On Cardiac Morphology And Function: Study In Uncomplicated Obesity, (2002) Obesity Research, vol. 10, pp. 767-773.
Igel, J.; On the Small-Scale Variability of Electrical Soil Properties and Its Influence on Geophysical Measurements; Ph.D. Thesis; Frankfurt University; Hanover, Germany; p. 188; 2007.
Ivorra, A., et al.; Bioimpedence dispersion width as a parameter to monitor living tissues; Physiol. Meas. 26 (2005) S165-S173.
Jones, C.H. et al; Extracellular fluid volume determined by bioelectric impedance and serum albumin in CAPD patients; Nephrology Dialysis Transplantation; vol. 13, pp. 393-397; 1998.
Jossinet, J. et al.; A Study For Breast Imaging with a Circular Array of Impedence Electrodes; Proc. Vth Int. Conf. Bioelectrical Impedence, 1981, Tokyo, Japan; pp. 83-86; 1981.
Jossinet, J. et al.; Technical Implementation and Evaluation of a Bioelectrical Breast Scanner; Proc. 10.sup.th Int. Conf. IEEE Engng. Med. Biol., 1988, New Orleans, USA (Imped. Imaging II); vol. 1. p. 289; 1988.
Kanai, H. et al.; Electrical Measurement of Fluid Distribution in Legs and Arms; Medical Progress through technology; pp. 159-170; 1987.
Karason, K., et al., Impact Of Blood Pressure And Insulin On The Relationship Between Body Fat And Left Ventricular Structure, (2003) European Heart Journal, vol. 24, pp. 1500-1505.
Kim, C.T. et al.; Bioelectrical impedence changes in regional extracellular fluid alterations; Electromyography and Clinical Neurophysiology; vol. 37, pp. 297-304; 1997.
Kim, et al., "Impedence Tomography and Its Application in Deep Venous Thrombosis Detection" IEEE Engineering in Medicine and Biology Magazine, IEEE Service Center, 1989, pp. 46-49, vol. 8, No. 1.
Kyle et al.; Bioelectrical Impedance Analysis—Part I: Review of Principles and Methods; Clinical Nutrition; vol. 23, pp. 1226-1243; 2004.
Liu R. et al; Primary Multi-frequency Data Analyze in Electrical Impedence Scanning; Proceeding of the IEEE-EMBS 2005, 27th Annual International Conference of the Engineering in Medicine and Biology Society, Shanghai, China; pp. 1504-1507;, Sep. 1-4, 2005.
Loke et al.; Least Squares Deconvolution of Apparent Resistivity Pseudosections; Geophysics; vol. 60, No. 6, pp. 1682-1690; 1995.
Lozano, A. et al.; Two-frequency impedance plethysmograph: real and imaginary parts; Medical & Biological Engineering & Computing; vol. 28, No. 1, pp. 38-42; Jan. 1990.
Lukaski, H.C. et al.; Estimation of Body Fluid Volumes Using Tetrapolar Bioelectrical Impedance Measurements; Aviation, Space, and Environmental Medicine; pp. 1163-1169; Dec. 1998.
Man, B. et al. Results of Preclinical Tests for Breast Cancer Detection by Dielectric Measurements; XII Int. Conf. Med. Biol. Engng. 1979, Jerusalem, Israel. Springer Int., Berlin; Section 30.4; 1980.
Mattar, J.A., Application of Total Body Impedance to the Critically Ill Patient, New Horizons, vol. 4, No. 4, pp. 493-503, 1996.
McAdams et al.; Tissue Impedance: a Historical Overview Physiological Measurement; Institute of Physics Publishing; vol. 16. (3A), pp. A1-A13; 1995.
McCullagh, W. A. et al., IFMBE Proceedings, vol. 17, p. 619, 2007.
McDougal D., et al.; Body Composition Measurements From Whole Body Resistance and Reactance; Surgical Forum; vol. 36, pp. 43-44; 1986.
McEwan et al.; Battery Powered and Wireless Electrical Impedance Tomography Spectroscopy Imaging Ssing Bluetooth; Medicon IFMBE Proceedings; vol. 16, pp. 798-801; 2007.
Nawarycz, et al., "Triple-Frequency Electroimpedance Method for Evaluation of Body Water Compartments" Medical & Biological Engineering & Computing, 1996, pp. 181-182, vol. 34, No. Supp. 01, PT. 02.
Noshiro, et al., "Electrical Impedance in the Lower Limbs of Patients With Duchenne Muscular Dystrophy: A Preliminary Study" Medical & Biological Engineering & Computing, 1993, pp. 97-102, vol. 31, No. 2.
Organs; Bioelectrochemistry and Bioenergetics; vol. 45, pp. 145-149; 1998.
Osterman K.S. et al.; Multifrequency electrical impedance imaging: preliminary in vivo experience in breast; Physiological Measurement; vol. 21, No. 1, pp. 99-109; Feb. 2000.
Ott, M. et al.; Bioelectrical Impedance Analysis as a Predictor of Survival in Patients with Human Immunodeficiency Virus Infection; Journal of Acquired Immune Deficiency Syndromes and Human Retrovirology; vol. 9, pp. 20-25; 1995.
Pethig, R. et al.; The Passive Electrical Properties of Biological Systems: Their Significance In Physiology, Biophysics and Biotechnology; Physics in Medicine and Biology; vol. 32, pp. 933-970; 1987.
Piperno, G. et al.; Breast Cancer Screening by Impedance Measurements; Frontiers of Medical & Biological Engineering; vol. 2, pp. 111-117; 1990.
Rigaud, B. et al.; Bioelectrical Impedance Techniques in Medicine; Critical Reviews in Biomedical Engineering; vol. 24 (4-6), pp. 257-351; 1996.
Roy, A.; Depth of investigation in Direct Current Methods Geophysics; vol. 36, pp. 943-959 ; 1971.
Scharfetter, H. et al.; Effect of Postural Changes on the Reliability of Volume Estimations from Bioimpedance Spectroscopy Data; Kidney International; vol. 51, No. 4, pp. 1078-2087; 1997.
Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; vol. 5, pp. 1934-1935; Oct. 31, 1996.
Seo, et al., "Measuring Lower Leg Swelling: Optimum Frequency for Impedance Method" Medical & Biological Engineering & Computing , 2001, pp. 185-189, vol. 39.
Seoane, et al., "Current Source for Wideband Electrical Bioimpedance Spectroscopy Based on a Single Operational Amplifier" World Congress on Medical Physics and Biomedical Engineering 2006, pp. 707-710 , vol. 14.
Skidmore, R. et al.; A Data Collection System for Gathering Electrical Impedance Measurements from the Human Breast; Clinical Physics Physiological Measurement; vol. 8, pp. 99-102; 1987.
Smith, et al., "A Pilot Study for Tissue Characterization Using Bio-Impedance Mapping" 13th International Conference on Electrical Bio-Impedance and the 8th Conference on Electrical Impedance Tomography 2007, pp. 146-149.
Sollish, B.D. et al.; Microprocessor-assisted Screening Techniques; Israel Journal of Medical Sciences; vol. 17, pp. 859-864; 1981.
Stanton, et al., "Non-Invasive Assessment of the Lymphedematous Limb" Lymphology, the International Society of Lymphology , 2000, pp. 122-135, vol. 33, No. 3.
Steijaert, M. et al.; The use of multi-frequency impedance to determine total body water and extracellular water in obese and lean female individuals; International Journal of Obesity; vol. 21, pp. 930-934; 1997.
Surowiec, A.J. et al.; Dielectric Properties of Brest Carcinoma and the Surrounding Tissues; IEEE Transactions on Biomedical Engineering; vol. 35, pp. 257-263; 1988.
Tedner, B.; Equipment Using Impedance Technique for Automatic Recording of Fluid-Volume Changes During Haemodialysis; Medical & Biological Engineering & Computing; pp. 285-290; 1983.
Thomas. B.J. et al.; Bioelectrical impedance analysis for measurement of body fluid volumes—A review; Journal of Clinical Engineering; vol. 17, No. 16, pp. 505-510; 1992.

(56) References Cited

OTHER PUBLICATIONS

Thomas. B.J. et al.; Bioimpedance Spectrometry in Determination of Body Water Compartments: Accuracy and Clinical Significance; Applied Radiation and Isotopes; vol. 49, No. 5/6, pp. 447-455; 1998.

Thomas. B.J.; Future Technologies; Asia Pacific Journal Clinical Nutrition; vol. 4, pp. 157-159; 1995.

Ulgen, Y. et al.; Electrical parameters of human blood; Engineering in Medicine and Biology Society, 1998. Proceedings of the 20th Annual International Conference of the IEEE; vol. 6, pp. 2983-2986; Nov. 1, 1998.

Ward, L.C. et al., Multi-frequency bioelectrical impedance augments the diagnosis and management of lymphoedema in post-mastectomy patients, European Journal of Clinical Investigation, vol. 22, pp. 751-754, 1992.

Ward, L.C. et al.; Determination of Cole parameters in multiple frequency bioelectrical impedance analysis using only the measurement of impedances; Four-frequency fitting; Physiological Measurement; vol. 27, No. 9, pp. 839-850; Sep. 2006.

Ward, L.C. et al.; There is a better way to measure Lymphoedema; National Lymphedema Network Newsletter; vol. 7, No. 4, pp. 89-92; Oct. 1995.

Wilson et al.; Feasibility Studies of Electrical Impedance Spectroscopy for Monitoring Tissue Response to Photodynamic Therapy; Optical Methods for Tumor Treatment and Detections: Mechanisms and Techniques in Photodynamic Therapy VII; Proc. SPIE 3247; pp. 69-80; 1998.

Woodrow, G. et al.; Effects of icodextrin in automated peritoneal dialysis on blood pressure and bioelectrical impedance analysis; Nephrology Dialysis Transplantation; vol. 15, pp. 862-866; 2000.

Yamakoshi, K.; Non-Invasive Cardiovascular Hemodynamic Measurements; Sensors in Medicine and Health Care; pp. 107-160; 2004.

Yoshinaga, M., Effect Of Total Adipose Weight And Systemic Hypertension On Left Ventricular Mass In Children, American Journal of Cardiology, (1995) vol. 76, pp. 785-787.

* cited by examiner

| Date and time | Age | Weight | R arm ratio | At risk | L arm ratio | At risk | R leg ratio | At risk | L leg ratio | At risk | RA Rzero |
|---|---|---|---|---|---|---|---|---|---|---|---|
| 27/06/2005 9:39:29 AM | 33.6 | 86.5 | 0.70 | N | 0.71 | N | 0.40 | Y | 0.29 | Y | 239.052 |
| 27/06/2005 9:44:32 AM | 33.6 | 86.5 | 0.73 | N | 0.74 | N | 0.37 | Y | 0.29 | Y | 235.045 |
| 27/06/2005 9:55:47 AM | 33.6 | 86.5 | 0.51 | N | 0.51 | N | 0.51 | Y | 0.29 | Y | 560.684 |
| 27/06/2005 9:59:12 AM | 33.6 | 86.5 | 0.51 | N | 0.51 | N | 0.51 | Y | 0.29 | Y | 560.768 |
| 27/06/2005 12:10:45 PM | 33.6 | 86.5 | 0.51 | N | 0.51 | N | 0.51 | Y | 0.29 | Y | 560.655 |

```
System    Measurements    Markers    Analysis    Print    Help
Current User  Test User
SUBJECT DETAILS  [Search]  [Edit]  [New]

First name [         ]  Family name [         ]   Date of birth [4/08/2005 ▽]  File number [    ]
Address    [normal population sample]              Sex [    ▽]                  Height [    ] cm
Comments   [                         ]             At-risk limbs  □R Arm  □L Arm  □R Leg  □L Leg Baseline start         Baseline end              Dom Arm  Dom Leg
[1/01/2000 ▽] [Set]   [1/01/2000 ▽] [Set]       [  ▽]    [  ▽]     [Done]  [Cancel]
```

RESULTS

| Date and time | Age | Weight | Height | Sex | Dom. arm | Dom. leg | R arm ratio | RA R zero | RA R inf | L arm ratio | LA R zero | LA R inf |
|---|---|---|---|---|---|---|---|---|---|---|---|---|
| 27/06/2005 1:08:19 PM | 45.0 | 64.7 | 178 | M | L | R | 0.56 | 559.538 | 359.092 | 0.56 | 559.361 | 359.1 |
| 27/06/2005 1:09:57 PM | 55.0 | 74.0 | 150 | F | R | R | 0.56 | 559.443 | 359.168 | 0.56 | 559.461 | 359.1 |
| 27/06/2005 1:10:54 PM | 55.0 | 74.0 | 150 | F | R | R | 0.56 | 559.093 | 359.093 | 0.56 | 559.371 | 359.1 |
| 27/06/2005 3:57:27 PM | 34.0 | 35.0 | 123 | F | L | L | 0.98 | 6.79 | 293.359 | 0.94 | 17.139 | 293.1 |

```
System    Measurements    Markers    Analysis    Print    Help
Current User  Test User
SUBJECT DETAILS  [Search]  [Edit]  [New]

First name [Joe]        Family name [Smith]       Date of birth [17/08/1971 ▽]  File number [Q301]
Address    [impedimed offices]                     Sex [Male ▽]                  Height [198.0] cm
Comments   [                         ]             At-risk limbs  □R Arm  □L Arm  ☑R Leg  ☑L Leg Baseline start         Baseline end              Dom Arm  Dom Leg
[5/05/2005 ▽] [Set]   [9/05/2005 ▽] [Set]        [Left ▽] [Right ▽]   [Done]  [Cancel]
```

RESULTS

| Date and time | Age | Weight | R arm ratio | At risk | RA R zero | RA R inf | L arm ratio | At risk | LA R zero | LA R inf |
|---|---|---|---|---|---|---|---|---|---|---|
| 10/05/2005 10:27:46 AM | 33.7 | 26.4 | 0.56 | Y | 560.664 | 359.646 | 0.14 | N | 560.181 | 489.758 |
| 10/05/2005 10:32:00 AM | 33.7 | 26.4 | 0.56 | Y | 560.371 | 359.551 | 0.56 | N | 560.39 | 359.51 |
| 10/05/2005 10:32:52 AM | 33.7 | 26.4 | 0.56 | Y | 560.3 | 359.571 | 0.56 | N | 560.357 | 359.483 |
| 11/05/2005 2:25:19 PM | 33.7 | 26.2 | 0.56 | Y | 560.949 | 359.762 | 0.94 | N | 560.849 | 359.739 |
| 11/05/2005 2:26:43 PM | 33.7 | 26.3 | 0.56 | Y | 560.588 | 359.705 | 0.56 | N | 560.607 | 359.685 |
| 25/05/2005 2:44:46 PM | 33.8 | 34.0 | 0.56 | Y | 559.676 | 358.389 | 0.56 | N | 559.633 | 358.366 |
| 25/05/2005 2:59:43 PM | 33.8 | 34.0 | 0.56 | Y | 559.597 | 358.234 | 0.56 | N | 559.497 | 358.237 |
| 25/05/2005 3:05:29 PM | 33.8 | 34.0 | 0.56 | Y | 559.343 | 358.294 | 0.59 | N | 560.702 | 352.777 |
| 25/07/2005 1:02:17 PM | 33.9 | 23.0 | 0.50 | N | 604.161 | 404.046 | 0.50 | Y | 604.176 | 403.949 |
| 25/07/2005 2:08:01 PM | 33.9 | 23.0 | 0.50 | N | 604.033 | 403.938 | 0.50 | Y | 604.104 | 403.952 |

MONITORING SYSTEM

CROSS-REFERENCE TO RELATED APPLICATIONS

This application is a continuation of U.S. patent application Ser. No. 11/993,219, filed Nov. 8, 2010, which is a U.S. National Phase under 35 U.S. C. § 371 of International Patent Application No. PCT/AU06/000924, filed Jun. 30, 2006, and published in English on Jan. 11, 2007 as WO 2007/002993, which claims the benefit of U.S. Provisional Application No. 60/697,100, filed Jul. 7, 2005, U.S. Provisional Application No. 60/697,101, filed Jul. 7, 2005, Australian Application No. 2005903510, filed Jul. 1, 2005, Australian Application No. 2005903603, filed Jul. 7, 2005, and Australian Application No. 2005904569, filed Aug. 23, 2005. The disclosure of U.S. patent application Ser. No. 11/993,219 is hereby incorporated by reference in its entirety.

BACKGROUND OF THE INVENTION

The present invention relates to a method and apparatus for monitoring biological parameters, and in particular to a method and apparatus for performing impedance measurements.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

One existing technique for determining biological parameters relating to a subject, such as cardiac function, involves the use of bioelectrical impedance. This involves measuring the electrical impedance of a subject's body using a series of electrodes placed on the skin surface. Changes in electrical impedance at the body's surface are used to determine parameters, such as changes in fluid levels, associated with the cardiac cycle or oedema.

Accordingly, complex signal processing is required to ensure measurements can be interpreted. Typically devices for achieving this utilise custom hardware configurations that are application specific. As a result, the devices can typically only be used in a limited range of circumstances.

Lymphoedema is a condition characterised by excess protein and oedema in the tissues as a result of reduced lymphatic transport capacity and/or reduced tissue proteolytic capacity in the presence of a normal lymphatic load. Acquired, or secondary lymphoedema, is caused by damaged or blocked lymphatic vessels. "The commonest inciting events are surgery and/or radiotherapy. However, onset of lymphoedema is unpredictable and may develop within days of its cause or at any time during a period of many years after that cause.

WO00/79255 describes a method of detection of oedema by measuring bioelectrical impedance at two different anatomical regions in the same subject at a single low frequency alternating current. The two measurements are analysed to obtain an indication of the presence of tissue oedema by comparing with data obtained from a normal population.

Other known methods of analysis of bioelectrical impedance measurements involve determining a phase and amplitude value for the measured signals. The measurement of amplitude is straightforward but the measurement of phase is more complicated and therefore the required equipment is costly.

In view of the different types of impedance measurement that can be performed, operators of impedance monitoring units have to be knowledgeable regarding their operation. In particular, it is necessary for the operator to know the location at which electrodes must be fitted, as well as the manner in which the electrodes must be coupled to the monitoring unit. It may also be necessary to change the connections midway through the monitoring process and this is often a difficult process.

In some situations, machines are only adapted to provide only one form of impedance analysis and as a result, provide a standard output that must then be interpreted by the operator. However, in the event that different operating modes can be selected, it is necessary for the operator of the machine to be aware of any intricacies associated with the selected measurement mode, as well as being able to interpret the different outputs that may be available.

SUMMARY OF THE PRESENT INVENTION

In a first broad form the present invention provides a method of performing impedance measurements on a subject, the method including, in a processing system:
  a) determining at least one impedance measurement to be performed;
  b) determining at least one electrode arrangement associated with the determined impedance measurement;
  c) displaying a representation indicative of the electrode arrangement; and,
  d) causing the impedance measurement to be performed once the electrodes have been arranged in accordance with the displayed representation.

Typically the method includes, in the processing system:
  a) receiving input commands indicating that the electrodes are arranged in accordance with the displayed arrangement; and,
  b) causing the impedance measurement to be performed in accordance with the received input command.

Typically the representation is indicative of:
  a) the position of a set of electrodes; and,
  b) lead connections between the processing system and a number of the set of electrodes.

Typically the representation includes, for each lead connection, a respective colour indication, the colour indication being indicative of a colour for a respective lead.

Typically the method includes, in the processing system:
  a) determining a sequence of measurements; and,
  b) generating a sequence of representations, each representation defining a respective electrode arrangement for performing a respective measurement.

Typically each measurement is performed for a corresponding body segment.

Typically the method includes:
  a) determining an impedance measurement type; and,
  b) determining, using the determined impedance measurement type, an impedance measurement profile, the profile being indicative of the at least one impedance measurement to be performed.

Typically the method includes, in the processing system:
  a) displaying an indication of available impedance measurement types; and, b) determining a respective one of the available impedance measurement types in accordance with input commands from an operator.

Typically the impedance measurement type is for determining at least one of:
a) one or more parameters relating to cardiac function;
b) the presence, absence or degree of oedema;
c) one or more parameters relating to body composition; and,
d) the subject's total body water; and,
e) the subject's Fat Free Mass (FFM).

Typically the method includes, in the processing system:
a) receiving data representing at least one measured impedance value; and,
b) generating a representation of the at least one measured impedance value.

Typically the method includes, in the processing system:
a) selecting a representation type based on a selected impedance measurement type; and,
b) generating the representation in accordance with the selected representation type.

Typically the representation is in the form of at least one of:
a) a Wessel plot;
b) an argand diagram;
c) a list of impedance values;
d) a reactance against frequency plot; and,
e) resistance against frequency plot.

Typically the method includes, in the processing system:
a) receiving data representing at least one measured impedance value;
b) processing the at least one measured impedance value to determine at least one impedance parameter; and,
c) generating a representation of the at least one impedance parameter.

Typically the method includes, in the processing system:
a) determining a processing operation based on a selected impedance measurement type; and,
b) processing the at least one measured impedance value in accordance with the determined processing operation.

Typically the method includes in the processing system:
a) determining at least one subject parameter relating to the subject; and,
b) at least one of:
  i) determining the impedance measurement to be performed in accordance with the determined at least one subject parameter, and,
  ii) processing at least one measured impedance value in accordance with the determined at least one subject parameter.

Typically the subject parameter is at least one of.
a) an indication of a presence, absence or degree of a condition;
b) an indication of an intervention;
c) an indication of a body segment at risk of a condition;
d) age;
e) height;
f) weight; and,
g) sex.

Typically the method includes, in the processing system, determining the at least one subject parameter from a remote database.

Typically the method includes, in the processing system:
a) determining a unique identifier indicative of an identity of the subject; and,
b) determining the at least one subject parameter using the unique identifier.

Typically the processing system is coupled to a reader for sensing coded data from a surface, and wherein the method includes, in the processing system:
a) receiving indicating data from the reader, the indicating data being indicative of the unique identifier and being determined by sensing coded data provided on a subject identification device; and,
b) using the indicating data to determine the unique identifier.

Typically the subject identification device is a bracelet having coded data disposed thereon.

Typically the method includes, in the processing system:
a) determining the availability of at least one reference; and,
b) at least one of
  i) determining the impedance measurement to be performed in accordance with the determined availability; and,
  ii) processing at least one measured impedance value in accordance with the determined availability.

Typically the positioning of the electrodes is performed in accordance with the theory of equal potentials.

Typically the positioning of the electrodes includes:
a) a first current supply electrode positioned on a limb being measured;
b) a second current supply electrode on a second limb on a the same lateral side of the subject as the limb being measured;
c) a first voltage electrode positioned on a limb being measured; and,
d) a second voltage electrode positioned on a third limb contra-lateral to the limb being measured.

Typically the processing system is coupled to a monitoring unit, and wherein the method includes, in the processing system:
a) generating instructions; and,
b) transferring the instructions to the monitoring unit, the monitoring unit being responsive to the instructions to cause the impedance measurements to be performed.

Typically the monitoring unit includes at least two channels, each channel being adapted to measure the impedance across a respective body segment, and wherein the method includes, in the processing system, causing at least one impedance measurement to be performed using each channel.

Typically the monitoring unit includes a processor, and wherein the processor is for
a) receiving the instructions; and,
b) causing one or more impedance measurements to be performed using the instructions.

Typically the method includes, causing the impedance measurement to be performed by:
a) causing one or more excitation signals to be applied to the subject; and,
b) determining one or more voltage signals measured across the subject.

Typically the one or more excitation signals are at least one of:
a) a number of current signals, each current signal having a respective frequency; and,
b) a current signal formed from a number of superposed frequencies.

In a second broad form the present invention provides apparatus for performing impedance measurements on a subject, the apparatus including a processing system for:

a) determining at least one impedance measurement to be performed;
b) determining at least one electrode arrangement associated with the determined impedance measurement;
c) displaying a representation indicative of the electrode arrangement; and,
d) causing the impedance measurement to be performed once the electrodes have been arranged in accordance with the displayed representation.

In a third broad form the present invention provides a method of performing impedance measurements on a subject, the method including, in a processing system:
a) determining at least one impedance measurement to be performed;
b) receiving data representing at least one measured impedance value;
c) processing the at least one measured impedance value to determine at least one impedance parameter; and,
d) generating a representation of the at least one impedance parameter, wherein at least one of the processing and the generating are performed in accordance with the at least one impedance measurement.

Typically the method includes, in the processing system:
a) selecting a representation type based on a selected impedance measurement type; and,
b) generating a representation of the at least one measured impedance value in accordance with the selected representation type.

Typically the representation is in the form of at least one of:
a) a Wessel plot;
b) an argand diagram;
c) a list of impedance values;
d) a reactance against frequency plot; and,
e) resistance against frequency plot.

Typically the method includes, in the processing system:
a) determining a processing operation based on a selected impedance measurement type; and,
b) processing the at least one measured impedance value in accordance with the determined processing operation.

Typically the method includes in the processing system:
a) determining at least one subject parameter relating to the subject; and,
b) at least one of
i) determining the impedance measurement to be performed in accordance with the determined at least one subject parameter, and,
ii) processing the at least one measured impedance value in accordance with the determined at least one subject parameter.

Typically the subject parameter is at least one of:
a) an indication of a presence, absence or degree of a condition;
b) an indication of an intervention;
c) an indication of a body segment at risk of a condition;
d) age;
e) height;
f) weight; and,
g) sex.

Typically the method includes, in the processing system:
a) determining the availability of at least one reference; and,
b) at least one of:
i) determining the impedance measurement to be performed in accordance with the determined availability; and,
ii) processing the at least one measured impedance value in accordance with the determined availability.

In a fourth broad form the present invention provides apparatus for performing impedance measurements on a subject, the apparatus including a processing system for:
a) determining at least one impedance measurement to be performed;
b) receiving data representing at least one measured impedance value;
c) processing the at least one measured impedance value to determine at least one impedance parameter, and,
d) generating a representation of the at least one impedance parameter, wherein at least one of the processing and generating representation are performed in accordance with the at least one impedance measurement.

In another broad form the present invention provides a method of performing impedance measurements on a subject, the method including, in a processing system:
a) determining at least one impedance measurement type;
b) determining a profile indicative of a sequence of impedance measurements;
c) displaying a representation indicative of required electrode arrangements; and,
d) causing the impedance measurements to be performed.

Typically the processing system is coupled to a monitoring unit, and wherein the method includes, in the processing system:
a) generating instructions; and,
b) transferring the instructions to the monitoring unit, the monitoring unit being responsive to the instructions to cause the impedance measurements to be performed.

Typically the method includes using a monitoring unit including a processor, and wherein the processor is for:
a) receiving the instructions; and,
b) causing one or more impedance measurements to be performed using the instructions.

Typically the method includes, causing the impedance measurement to be performed by:
a) causing one or more excitation signals to be applied to the subject; and,
b) determining one or more voltage signals measured across the subject.

Typically the one or more excitation signals are at least one of:
a) a number of current signals, each current signal having a respective frequency; and,
b) a current signal formed from a number of superposed frequencies.

Typically the method includes using a monitoring unit including at least two channels, each channel being adapted to measure the impedance across a respective body segment, and wherein the method includes, in the processing system, causing at least one impedance measurement to be performed using each channel.

Typically each channel being adapted to measure the impedance across a respective body segment, and wherein the method includes, in the processing system, causing at least one impedance measurement to be performed using each channel.

Typically the method includes, in the processing system:
a) displaying an indication of available impedance measurement types; and,
b) determining a respective one of the available impedance measurement types in accordance with input commands from an operator.

Typically the impedance measurement type is for determining at least one of:
a) one or more parameters relating to cardiac function;
b) the presence, absence or degree of oedema;
c) one or more parameters relating to body composition; and,
d) the subject's total body water; and,
e) the subject's Fat Free Mass (FFM).

Typically the method includes in the processing system:
a) determining at least one subject parameter relating to the subject; and,
b) at least one of:
  i) determining the impedance measurement to be performed in accordance with the determined at least one subject parameter; and,
  ii) processing at least one measured impedance value in accordance with the determined at least one subject parameter.

Typically the subject parameter is at least one of:
a) an indication of a presence, absence or degree of a condition;
b) an indication of an intervention;
c) an indication of a body segment at risk of a condition;
d) age;
e) height;
f) weight; and,
g) sex.

Typically the method includes, in the processing system, determining the at least one subject parameter from a remote database.

Typically the method includes, in the processing system:
a) determining a unique identifier indicative of an identity of the subject; and,
b) determining the at least one subject parameter using the unique identifier.

Typically the processing system is coupled to a reader for sensing coded data from a surface, and wherein the method includes, in the processing system:
a) receiving indicating data from the reader, the indicating data being indicative of the unique identifier and being determined by sensing coded data provided on a subject identification device; and,
b) using the indicating data to determine the unique identifier.

Typically the subject identification device is a bracelet having coded data disposed thereon.

In a fifth broad form the present invention provides apparatus for performing impedance measurements on a subject, the apparatus including a processing system for:
a) determining at least one impedance measurement type;
b) determining a profile indicative of a sequence of impedance measurements;
c) displaying a representation indicative of required electrode arrangements; and,
d) causing the impedance measurements to be performed.

In a sixth broad form the present invention provides a method for configuring a processing system for use in impedance analysis of a subject, the method including, in a processing system:
a) receiving configuration data, the configuration data being indicative of at least one feature;
b) determining, using the configuration data, instructions representing the at least one feature; and,
c) causing, at least in part using the instructions, at least one of:
  i) impedance measurements to be performed; and,
  ii) analysis of impedance measurements.

Typically the configuration data includes the instructions.
a) determining an indication of the at least one feature using the configuration data; and,
b) determining the instructions using the indication of the at least one feature.

Typically the method includes, in the processing system, decrypting the received configuration data.

Typically the method includes, in the processing system:
a) determining a device identifier associated with the processing system;
b) determining, using the device identifier, a key; and,
c) decrypting the received configuration data using the key.

Typically the processing system includes first and second processing systems, and wherein the method includes:
a) in the first processing system, selecting the instructions using the configuration data; and,
b) in the second processing system, generating the control signals using selected instructions.

Typically the method includes, in the processing first system, at least one of
a) transferring the instructions to the second processing system; and,
b) causing the second processing system to access the instructions from a store.

Typically the method includes, in the processing system, receiving the configuration data from at least one of a computer system and a communications network.

Typically the method includes, in the processing system:
a) determining if a feature selected by a user is available;
b) if the feature is not available, determining if the user wishes to enable the feature; and,
c) if the user wishes to enable the feature, causing configuration data to be received.

Typically the method includes, in the processing system:
a) causing the user to provide a payment to a device provider; and,
b) receiving the configuration data in response to payment.

In a seventh broad form the present invention provides apparatus for configuring a processing system for use in impedance analysis of a subject, the apparatus including a processing system for:
a) receiving configuration data, the configuration data being indicative of at least one feature;
b) determining, using the configuration data, instructions representing the at least one feature; and,
c) causing, at least in part using the instructions, at least one of:
  i) impedance measurements to be performed; and,
  ii) analysis of impedance measurements.

Typically the processing system forms at least part of at least one of
a) an end station; and,
b) a measuring device.

In an eighth broad form the present invention provides a method for configuring a processing system for use in impedance analysis of a subject, the method including, in a computer system:
a) determining configuration data required for the processing system, the configuration data being indicative of at least one feature; and,
b) causing the configuration data to be received by the processing system being responsive to the configuration data to cause, at least one of:
  i) impedance measurements to be performed; and,
  ii) analysis of impedance measurements.

Typically the method includes, in the computer system:
a) determining a device identifier, the device identifier being associated with the processing system to be configured; and,
b) using the device identifier to at least one of:
  i) transfer the configuration data to the processing system; and,
  ii) encrypt the configuration data.

Typically the method includes, in the computer system, determining the configuration data is required in response to at least one of
a) payment made by a user of the processing system; and,
b) approval of the feature.

Typically the method includes, in the computer system:
a) determining regulatory approval of the at least one feature in at least one region;
b) determining at least one processing system in the at least one region; and,
c) configuring the at least one processing system.

In a ninth broad form the present invention provides apparatus for configuring a processing system for use impedance analysis of a subject, the method including, in a computer system:
a) determining configuration data required for a processing system, the configuration data being indicative of at least one feature; and,
b) causing the configuration data to be received by the processing system being responsive to the configuration data to cause, at least one of
  i) impedance measurements to be performed; and,
  ii) analysis of impedance measurements.

It will be appreciated that the broad forms of the invention may be used individual or in combination, and may be used for diagnosis of the presence, absence or degree of a range of conditions and illnesses, including, but not limited to oedema, pulmonary oedema, lymphoedema, body composition, cardiac function, and the like.

BRIEF DESCRIPTION OF THE DRAWINGS

An example of the present invention will now be described with reference to the accompanying drawings, in which:—

FIGS. 8A and 8B are examples of a GUI used in providing subject details;

FIGS. 9D to 9I are examples of a GUI used in performing the impedance measurements;

FIGS. 11A and 11B are examples of a GUI used in selecting references;

FIG. 12 is an example of a GUI used in performing total body impedance measurements;

FIG. 14 is a schematic of a GUI used in configuring the apparatus of FIG. 3;

DETAILED DESCRIPTION OF THE PREFERRED EMBODIMENTS

Figure 1:
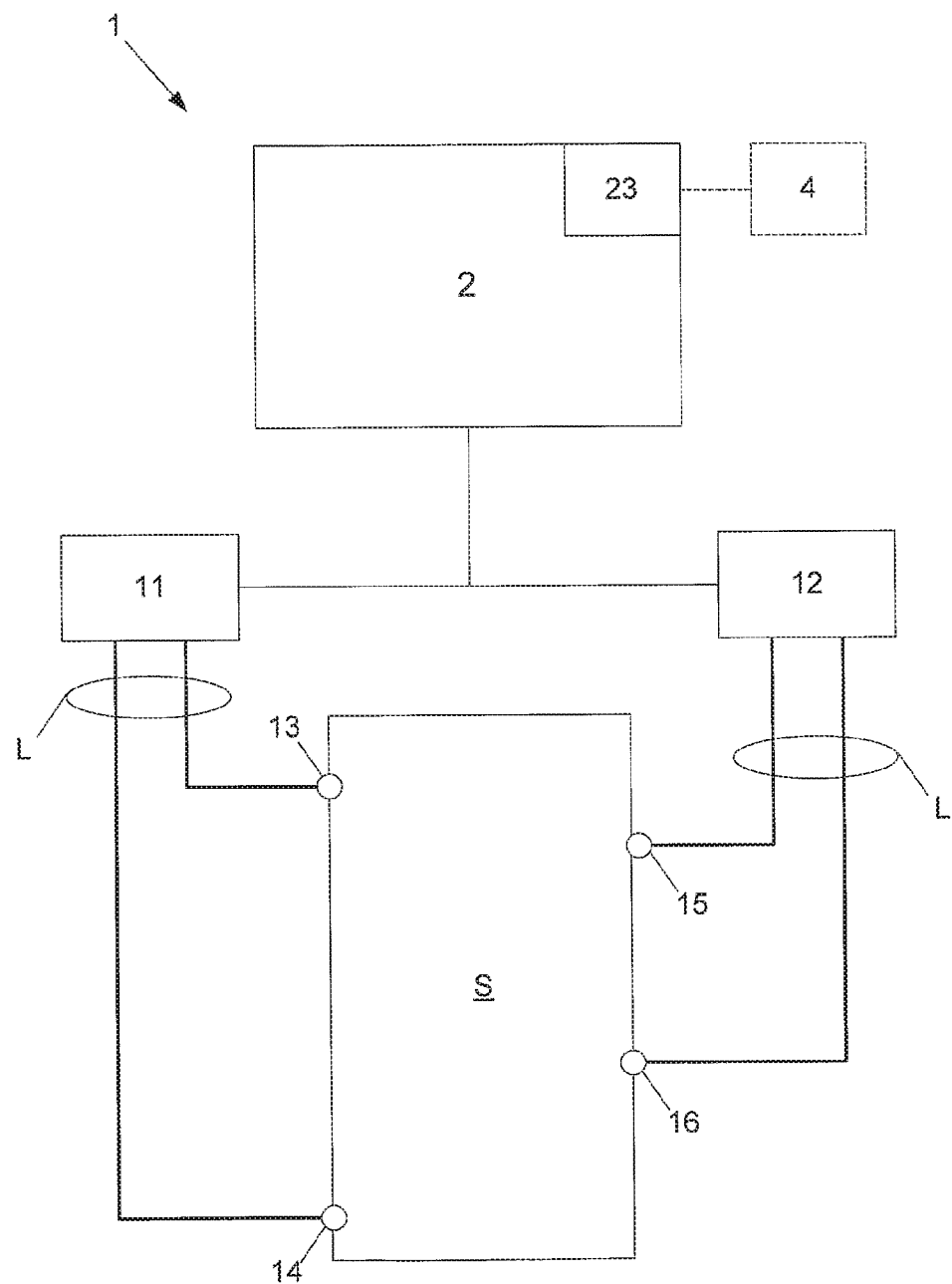
FIG. 1 is a schematic of an example of impedance determination apparatus.

An example of apparatus suitable for performing an analysis of a subject's impedance will now be described with reference to FIG. 1.

As shown the apparatus includes a measuring device 1 including a processing system 2 coupled to a signal generator 11 and a sensor 12. In use the signal generator 11 and the sensor 12 are coupled to respective electrodes 13, 14, 15, 16, provided on a subject S, via leads L, as shown. An optional external interface 23 can be used to couple the measuring device 1 to one or more peripheral devices 4, such as an external database or computer system, barcode scanner, or the like.

In use, the processing system 2 is adapted to generate control signals, which causes the signal generator 11 to generate one or more alternating signals, such as voltage or current signals, which can be applied to a subject S, via the electrodes 13, 14. The sensor 12 then determines the voltage across or current through the subject S, using the electrodes 15, 16 and transfers appropriate signals to the processing system 2.

Accordingly, it will be appreciated that the processing system 2 may be any form of processing system which is suitable for generating appropriate control signals and interpreting an indication of the measured signals to thereby determine the subject's bioelectrical impedance, and optionally determine other information such as the cardiac parameters, presence absence or degree of oedema, or the like.

The processing system 2 may therefore be a suitably programmed computer system, such as a laptop, desktop, PDA, smart phone or the like. Alternatively the processing system 2 may be formed from specialised hardware. Similarly, the I/O device may be of any suitable form such as a touch screen, a keypad and display, or the like.

It will be appreciated that the processing system 2, the signal generator 11 and the sensor 12 may be integrated into a common housing and therefore form an integrated device. Alternatively, the processing system 2 may be connected to the signal generator 11 and the sensor 12 via wired or wireless connections. This allows the processing system 2 to be provided remotely to the signal generator 11 and the sensor 12. Thus, the signal generator 11 and the sensor 12 may be provided in a unit near, or worn by the subject S, whilst the processing system 2 is situated remotely to the subject S.

In one example, the outer pair of electrodes 13, 14 are placed on the thoracic and neck region of the subject S. However, this depends on the nature of the analysis being performed. Thus, for example, whilst this electrode arrangement is suitable for cardiac function analysis, in lymphoedema, the electrodes would typically be positioned on the limbs, as required.

Once the electrodes are positioned, an alternating signal is applied to the subject S. This may be performed either by applying an alternating signal at a plurality of frequencies simultaneously, or by applying a number of alternating signals at different frequencies sequentially. The frequency range of the applied signals may also depend on the analysis being performed.

In one example, the applied signal is a frequency rich current from a current source clamped, or otherwise limited, so it does not exceed the maximum allowable subject auxiliary current. However, alternatively, voltage signals may be applied, with a current induced in the subject being measured. The signal can either be constant current, impulse function or a constant voltage signal where the current is measured so it does not exceed the maximum allowable subject auxiliary current.

A potential difference and/or current are measured between an inner pair of electrodes 15, 16. The acquired signal and the measured signal will be a superposition of potentials generated by the human body, such as the ECO, and potentials generated by the applied current Optionally the distance between the inner pair of electrodes may be measured and recorded. Similarly, other parameters relating to the subject may be recorded, such as the height, weight, age, sex, health status, any interventions and the date and time on which they occurred. Other information, such as current medication, may also be recorded.

To assist accurate measurement of the impedance, buffer circuits may be placed in connectors that are used to connect the voltage sensing electrodes 15 to the leads L. This ensures accurate sensing of the voltage response of the subject S, and in particular helps eliminate contributions to the measured voltage due to the response of the leads L, and reduce signal loss.

This in turn greatly reduces artefacts caused by movement of the leads L, which is particularly important during dialysis as sessions usually last for several hours and the subject will move around and change positions during this time.

A further option is for the voltage to be measured differentially, meaning that the sensor used to measure the potential at each electrode 15, 16 only needs to measure half of the potential as compared to a single ended system.

The current measurement system may also have buffers placed in the connectors between the electrodes 13, 14 and the leads L. In one example, current can also be driven or sourced through the subject S symmetrically, which again greatly reduced the parasitic capacitances by halving the common-mode current Another particular advantage of using a symmetrical system is that the micro-electronics built into the connectors for each electrode 13, 14 also removes parasitic capacitances that arise when the subject S, and hence the leads L move.

The acquired signal is demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a processing technique such as multiplying the measured signal with a reference sine wave and cosine wave derived from the signal generator, or with measured sine and cosine waves, and integrating over a whole number of cycles. This process rejects any harmonic responses and significantly reduces random noise.

Other suitable digital and analog demodulation techniques will be known to persons skilled in the field.

Impedance or admittance measurements are determined from the signals at each frequency by comparing the recorded voltage and current signal. The demodulation algorithm will produce an amplitude and phase signal at each frequency.

Figure 2:
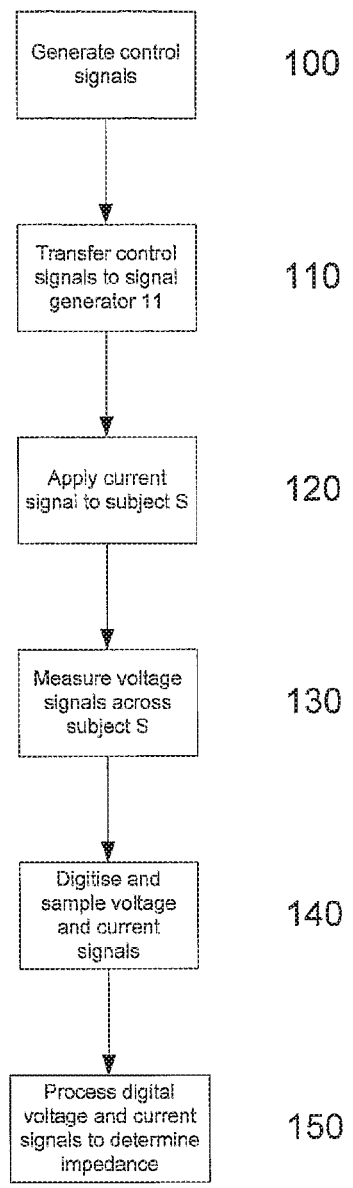
FIG. 2 is a flowchart of an example of a process for performing impedance determination.

An example of the operation of the apparatus for performing bioimpedance analysis will now be described with reference to FIG. 2.

At step 100, the processing system 2 operates to generate control signals which are provided to the signal generator 11 at step 110, thereby causing the signal generator to apply an alternating current signal to the subject S, at step 120. Typically the signal is applied at each of a number of frequencies $f_i$ to allow multiple frequency analysis to be performed.

At step 130 the sensor 12 senses voltage signals across the subject S. At step 140 the measuring device, operates to digitise and sample the voltage and current signals across the subject S, allowing these to be used to determine instantaneous bioimpedance values for the subject S at step 150.

Figure 3:
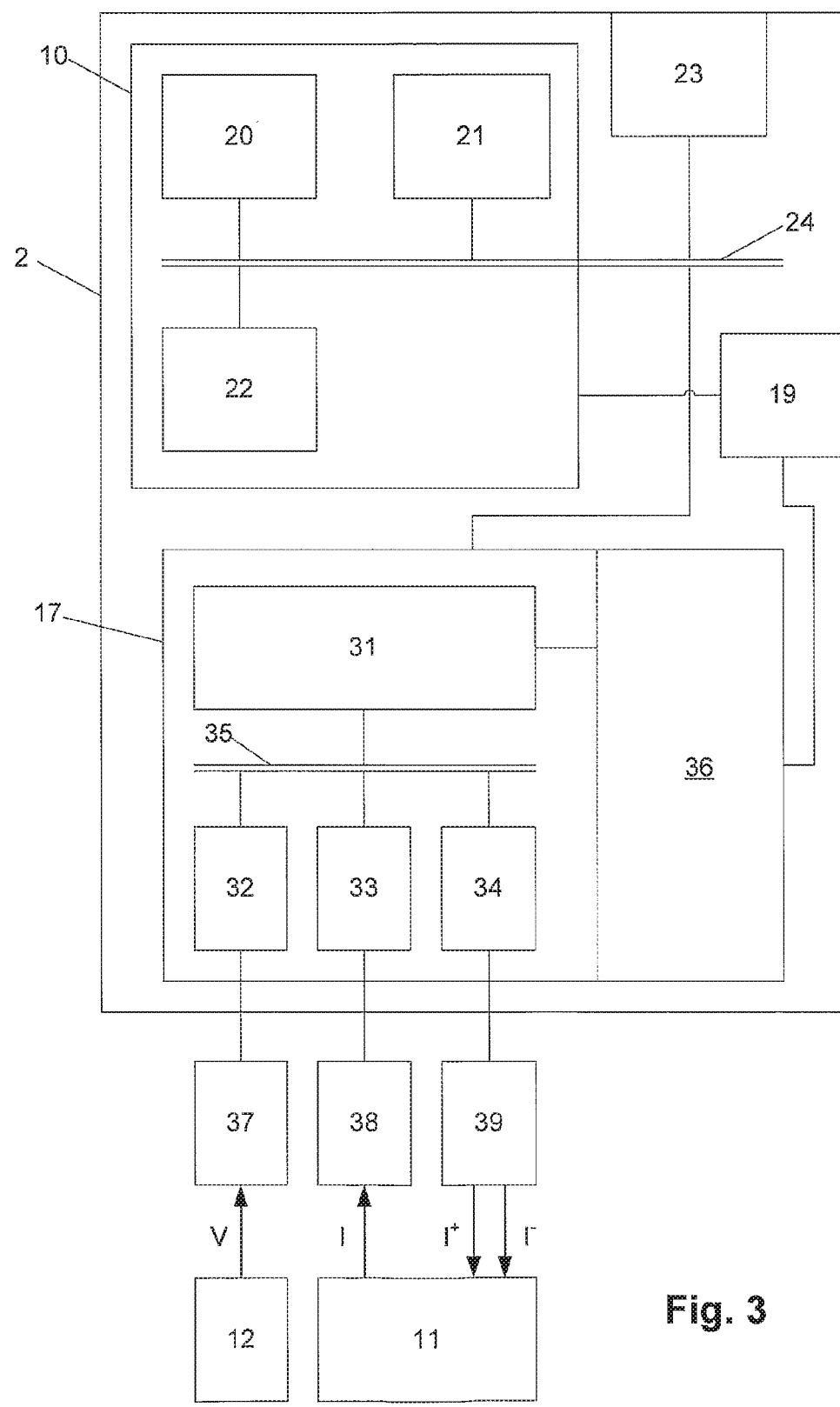
FIG. 3 is a schematic of a second example impedance determination apparatus.
Figure 4A:
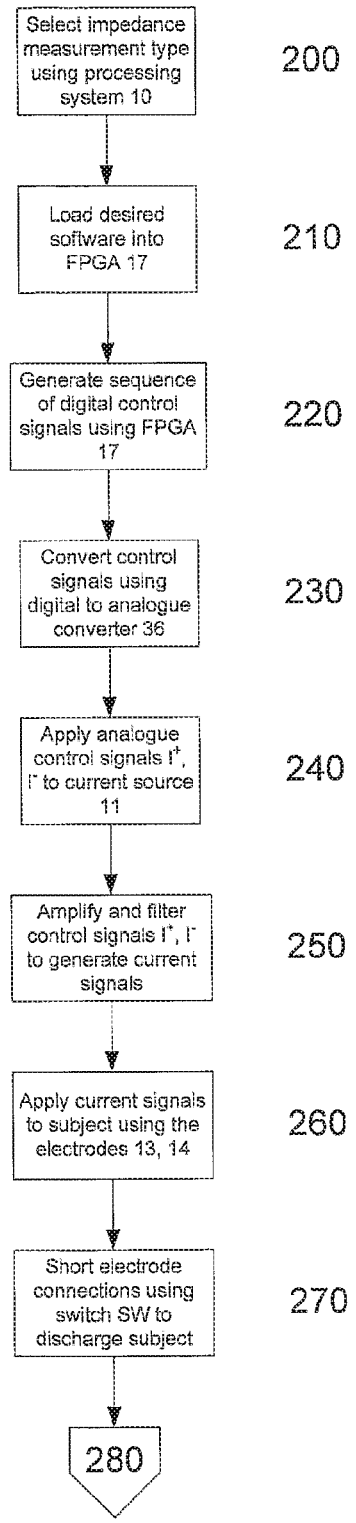
FIGS. 4A and 4B are a flowchart of a second example of a process for performing impedance determination.
Figure 4B:
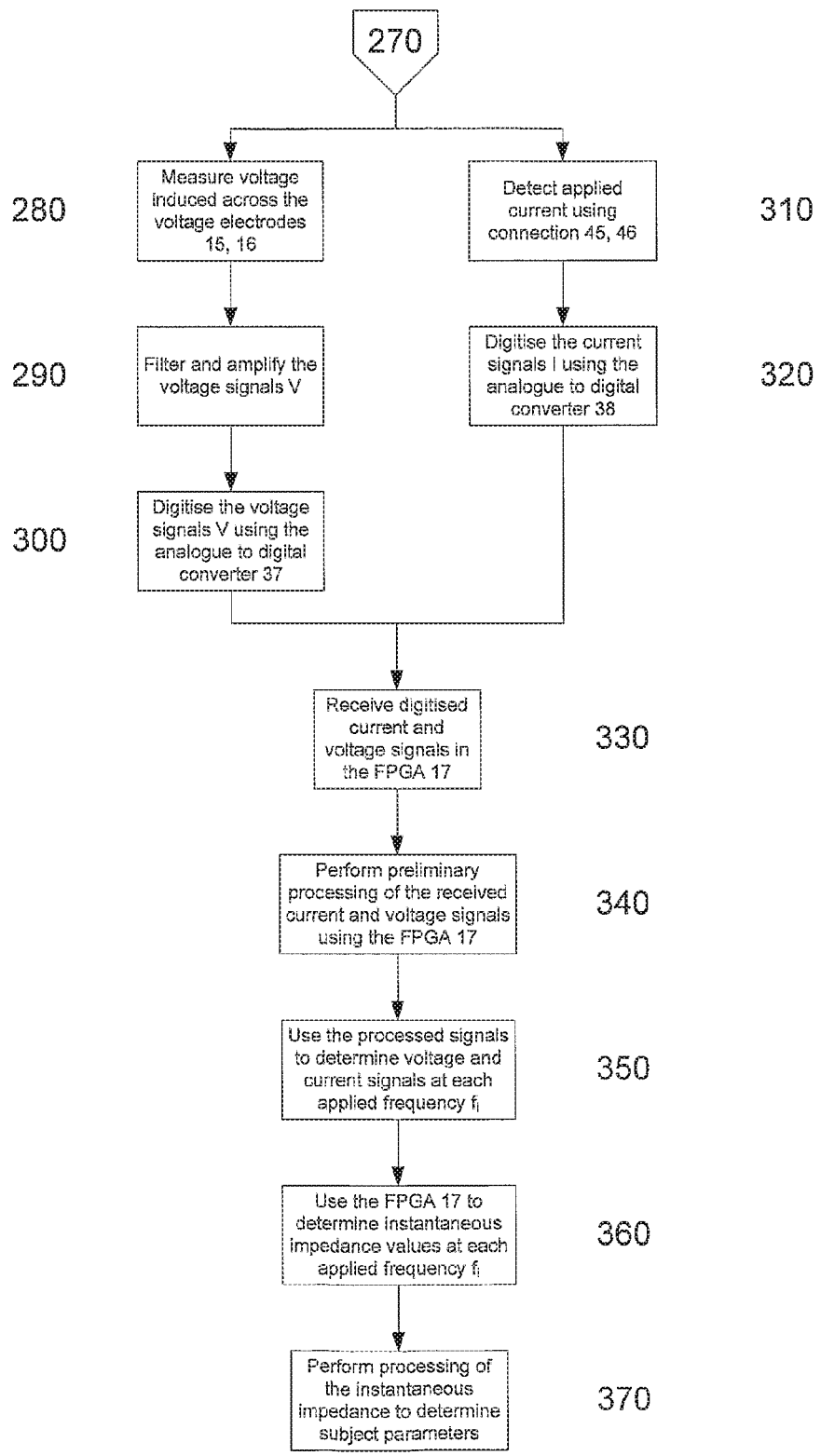

A specific example of the apparatus will now be described in more detail with respect to FIG. 3.

In this example, the processing system 2 includes a first processing system 10 having a processor 20, a memory 21, an input/output (I/O) device 22, and an external interface 23, coupled together via a bus 24. The processing system 2 also includes a second processing system 17, in the form of a processing module. A controller 19, such as a micrologic controller, may also be provided to control activation of the first and second processing systems 10, 17.

In use, the first processing system 10 controls the operation of the second processing system 17 to allow different impedance measurement procedures to be implemented, whilst the second processing system 17 performs specific processing tasks, to thereby reduce processing requirements on the first processing system 10.

Thus, the generation of the control signals, as well as the processing to determine instantaneous impedance values is performed by the second processing system 17, which may therefore be formed from custom hardware, or the like. In one particular example, the second processing system 17 is formed from a Field Programmable Gate Array (FPGA), although any suitable processing module, such as a magnetologic module, may be used.

The operation of the first and second processing systems 10, 17, and the controller 19 is typically controlled using one or more sets of appropriate instructions. These could be in any suitable form, and may therefore include, software, firmware, embedded systems, or the like.

The controller 19 typically operates to detect activation of the measuring device through the use of an on/off switch (not shown). Once the controller detects device activation, the controller 19 executes predefined instructions, which in turn causes activation of the first and second processing systems 10, 17, including controlling the supply of power to the processing systems as required.

The first processing system 10 can then operate to control the instructions, such as the firmware, implemented by the second processing system 17, which in turn alters the operation of the second processing system 17. Additionally, the first processing system 10 can operate to analyse impedance determined by the second processing system 17, to allow biological parameters to be determined. Accordingly, the first processing system 10 may be formed from custom hardware or the like, executing appropriate applications software to allow the processes described in more detail below to be implemented.

It will be appreciated that this division of processing between the first processing system 10, and the second processing system 17, is not essential, but there are a number of benefits that will become apparent from the remaining description.

In this example, the second processing system 17 includes a PCI bridge 31 coupled to programmable module 36 and a bus 35, as shown. The bus 35 is in turn coupled to processing modules 32, 33, 34, which interface with ADCs (Analogue to Digital Converters) 37, 38, and a DAC (Digital to Analogue Converter) 39, respectively.

The programmable module 36 is formed from programmable hardware, the operation of which is controlled using the instructions, which are typically downloaded from the first processing system 10.

The firmware that specifies the configuration of hardware 36 may reside in flash memory (not shown), in the memory 21, or may be downloaded from an external source via the external interface 23.

Alternatively, the instructions may be stored within inbuilt memory on the second processing system 17. In this example, the first processing system 10 typically selects firmware for implementation, before causing this to be implemented by the second processing system 17. This may be achieved to allow selective activation of functions encoded within the firmware, and can be performed for example using configuration data, such as a configuration file, or instructions representing applications software or firmware, or the like, as will be described in more detail below.

In either case, this allows the first processing system 10 to be used to control operation of the second processing system 17 to allow predetermined current sequences to be applied to the subject S. Thus, for example, different firmware would be utilised if the current signal is to be used to analyse the impedance at a number of frequencies simultaneously, for example, by using a current signal formed from a number of superposed frequencies, as compared to the use of current signals applied at different frequencies sequentially.

An example of operation of the apparatus will now be described with reference to FIGS. 6A to 6C.

At step 200 an operator selects an impedance measurement type using the first processing system 10. This may be achieved in a number of ways and will typically involve having the first processing system 10 store a number of different profiles, each of which corresponds to a respective impedance measurement protocol.

Thus, for example, when performing cardiac function determination, it will be typical to use a different applied current sequence and a different impedance analysis, as compared to performing lymphoedema measurements, body composition, pulmonary oedema, or the like. The profile will typically be stored in the memory 21, or alternatively may be downloaded from flash memory (not shown), or via the external interface 23.

Once an appropriate measurement type has been selected by the operator, this will cause the first processing system 10 to load desired code module firmware into the programmable module 36 of the second processing system 17 at step 210, or cause embedded firmware to be activated. The type of code module used will depend on the preferred implementation, and in one example this is formed from a wishbone code module, although this is not essential.

At step 220, the second processing system 17 is used to generate a sequence of digital control signals, which are transferred to the DAC 39 at step 230. This is typically achieved using the processing module 34, by having the module generate a predetermined sequence of signals based on the selected impedance measurement profile. This can therefore be achieved by having the second processing system 17 program the processing module 34 to cause the module to generate the required signals.

The DAC 39 converts the digital control signals into analogue control signals $I^+$, $I^-$ which are then applied to the current source 11 at step 240.

As described above, the current source circuit operates to amplify and filter the electrical control signals $I^+$, $I^-$ at step 250, applying the resulting current signals to the electrodes 13, 14 at step 260.

During this process, the current circuit through the subject can optionally be shorted at step 270, using a switch SW, to thereby discharge any residual field in the subject S, prior to readings being made.

At step 280, the measurement procedure commences, with the voltage across the subject being sensed from the electrodes 15, 16. In this regard, the voltage across the electrodes is filtered and amplified using the buffer circuit shown in FIG. 5 at step 290, with the resultant analogue voltage signals V being supplied to the ADC 37 and digitised at step 300. Simultaneously, at step 310 the current applied to the subject S is detected with the analogue current signals I being digitised using the ADC 38 at step 320.

The digitised voltage and current signals V, I are received by the processing modules 32, 33 at step 330, with these being used to performed preliminary processing of the signals at step 340.

The processing performed will again depend on the impedance measurement profile, and the consequent configuration of the processing modules 32, 33. This can include for example, processing the voltage signals V to extract ECG signals. The signals will also typically be filtered to ensure that only signals at the applied frequencies $f_i$, are used in impedance determination. This helps reduce the effects of noise, as well as reducing the amount of processing required.

At step 350 the second processing system 17 uses the processing signals to determine voltage and current signals at each applied frequency $f_i$, with these being used at step 360 to determine instantaneous impedance values at each applied frequency $f_i$.

The ADCs 37, 38 and the processing modules 32, 33 are typically adapted to perform sampling and processing of the voltage and current signals V, I in parallel so that the voltage induced at the corresponding applied current are analysed simultaneously. This reduces processing requirements by avoiding the need to determine which voltage signals were measured at which applied frequency. This is achieved by having the processing modules 32, 33 sample the digitised signals received from the ADCs 37, 38, using a common clock signal generated by the processing module 36, which thereby ensures synchronisation of the signal sampling.

Once the instantaneous impedance values have been derived, these can undergo further processing in either the first processing system 10, or the second processing system 17, at step 370. The processing of the instantaneous impedance signals will be performed in a number of different manners depending on the type of analysis to be used and this in turn will depend on the selection made by the operator at step 200.

Accordingly, it will be appreciated by persons skilled in the art that a range of different current sequences can be applied to the subject by making an appropriate measurement type selection. Once this has been performed, the FPGA operates to generate a sequence of appropriate control signals $I^+$, $I^+$, which are applied to the subject S using the signal generator 11. The voltage induced across the subject is then sensed using the sensor 12, allowing the impedance values to be determined and analysed by the second processing system 17.

Using the second processing system 17 allows the majority of processing to be performed using custom configured hardware. This has a number of benefits.

Firstly, the use of a second processing system 17 allows the custom hardware configuration to be adapted through the use of appropriate firmware. This in turn allows a single measuring device to be used to perform a range of different types of analysis.

Secondly, this vastly reduces the processing requirements on the first processing system 10. This in turn allows the first processing system 10 to be implemented using relatively straightforward hardware, whilst still allowing the measuring device to perform sufficient analysis to provide interpretation of the impedance. This can include for example generating a "Wessel" plot, using the impedance values to determine parameters relating to cardiac function, as well as determining the presence or absence of lymphoedema.

Thirdly, this allows the measuring device 1 to be updated. Thus for example, if an improved analysis algorithms is created, or an improved current sequence determined for a specific impedance measurement type, the measuring device can be updated by downloading new firmware via flash memory (not shown) or the external interface 23.

It will be appreciated that in the above examples, the processing is performed partially by the second processing system 17, and partially by the first processing system 10. However, it is also possible for processing to be performed by a single element, such as an FPGA, or a more generalised processing system.

As the FPGA is a custom processing system, it tends to be more efficient in operation than a more generic processing system. As a result, if an FPGA alone is used, it is generally possible to use a reduced overall amount of processing, allowing for a reduction in power consumption and size. However, the degree of flexibility, and in particular, the range of processing and analysis of the impedance which can be performed is limited.

Conversely, if only a generic processing system is used, the flexibility is enhanced at the expensive of a decrease in efficiency, and a consequent increase in size and power consumption.

Accordingly, the above described example strikes a balance, providing custom processing in the form of an FPGA to perform partial processing. This can allow for example, the impedance values to be determined. Subsequent analysis, which generally requires a greater degree of flexibility can then be implemented with the generic processing system.

A further disadvantage of utilising an FPGA alone is that it complicates the process of updating the processing, for example, if improved processing algorithms are implemented.

Figure 5:
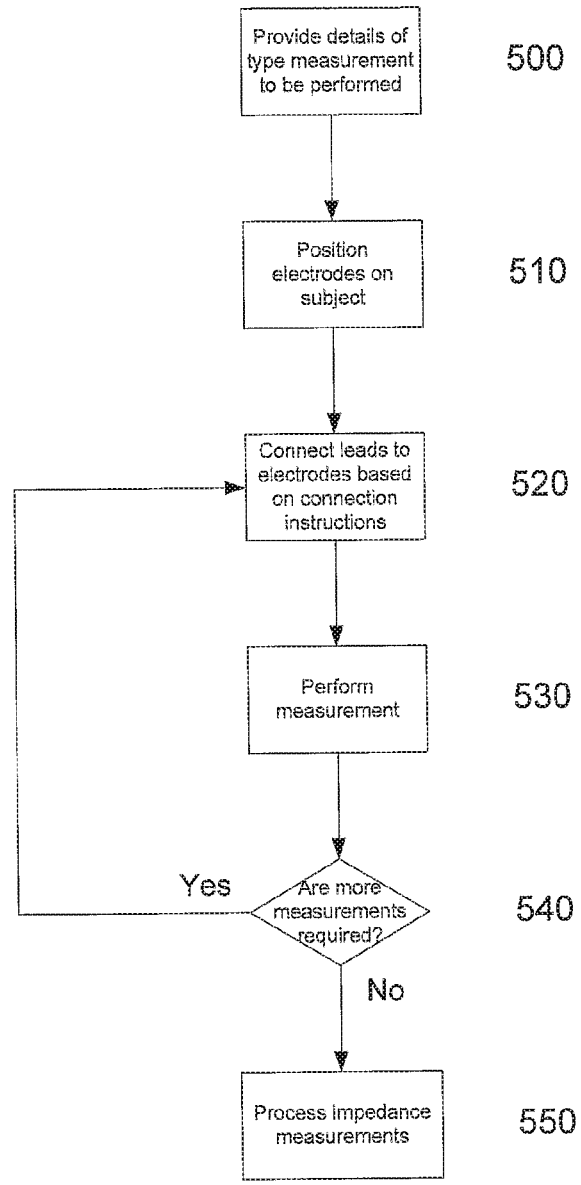
FIG. 5 is a flowchart of an example of a process for performing impedance determination.

An example of the process for performing impedance measurements utilising the apparatus to FIG. 3 will now be described with reference to FIG. 5.

At step 500 an operator of the apparatus provides details of a type of impedance measurement to be performed. At step 510 the operator positions electrodes on the subject before connecting leads to the electrodes based on connection instructions provided by the apparatus at step 520.

This process will therefore typically involve having the operator place a number of electrodes on the subject and then connecting leads to selected ones of the electrodes based on the particular measurement being performed.

At step 530 the measuring device 1 will operate to perform impedance measurements by generating an appropriate current sequence and applying this to the subject via the electrodes 13, 14.

At step 540 the measuring device 1 determines if further impedance measurements are required and if so the process returns to step 520 to allow the operator to connect leads to different ones of the electrodes as required. This process is repeated until sufficient impedance measurements have been collected to perform the required analysis.

At this stage, the process moves on to step 550 with the measuring device 1 operating to process the impedance measurements and provide an indication of required information to the operator.

It will therefore be appreciated that this may be achieved in a number of ways and that typically, this involves having the operator select a predetermined impedance measurement procedure and then follow instructions provided by the measuring device 1 to allow the impedance measurements to be correctly collected.

This process will now be described in more detail with respect to FIGS. 6A and 6B, which describe the process of collecting impedance data.

Figure 6A:
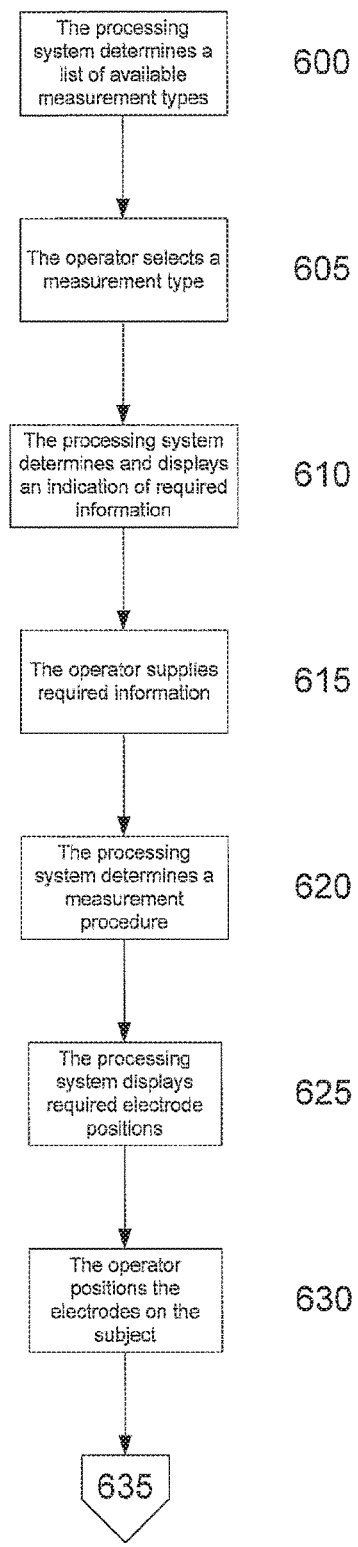
FIGS. 6A and 6B are a flow chart of a second example of a process for performing impedance determination.
Figure 6B:
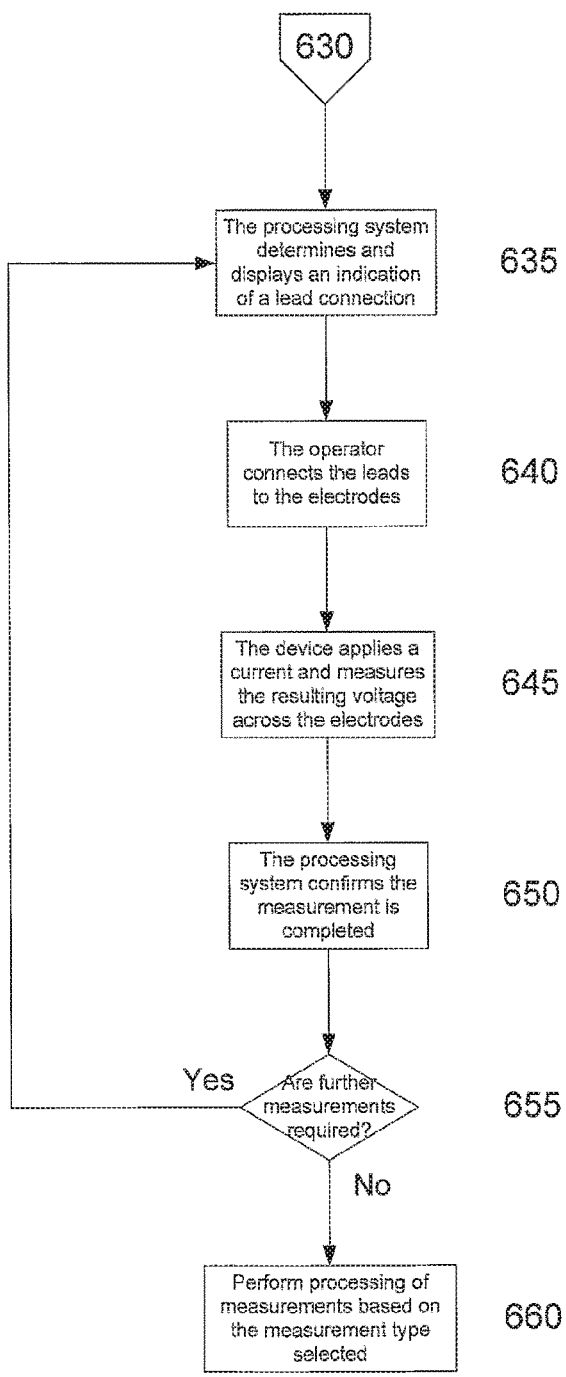

In the example set out in FIG. 6A at step 600 the operator activates the measuring device 1 causing the first processing system 10 to determine a list of the available measurement types. The available measurement types will be determined either from the memory 21, or alternatively downloaded via the external interface 23 and are based on predetermined profiles which provide suitable instructions to allow the measuring device 1 to perform the required impedance measurements.

Thus, it will be appreciated by a person skilled in the art that the profiles will depend for example on factors such as the type of impedance measurements to be performed, or the like. Thus, for example the profile will be different for cardiac parameter determination as compared to oedema detection.

In any event, the first processing system 10 will display a list of available measurement types to the operator utilising a suitable GUI.

At step 605 the operator selects an appropriate one of the measurement types. This causes the first processing system 10 to access the corresponding profile and determine if any additional information is required, such as body parameters including age, weight, sex, an indication of body segments, such as limbs to be analysed, or the like.

Additionally the first processing system 10 can be adapted to assist the operator in selecting the correct measurement type. For example, the particular measurement that should be made may depend on a number of factors, such as the body parameters, as well as whether any interventions have occurred. In this instance, the operator can provide details of the body parameters, interventions, or the like. The first processing system 10 can then uses these to access details of available measurement types and determine the preferred measurement type for the given situation.

The selection of the preferred measurement type can be performed in a number of ways. For example, the first processing system 10 may access an LUT (look-up table) that specifies the measurement profile that should be used in different circumstances. The relationships in the LUT can be defined by medically qualified personnel, thereby removing the requirement on the operator to make a medical decision. Alternatively rules may be provided in the profiles, so that the first processing system 10 is only able to access profiles that are suitable for the current body parameter and intervention status.

Rules can alternatively be derived using heuristic algorithms based on selections made by medically qualified operators during measurement procedures. It will be appreciated that in this instance, as the device is used, the first processing system 10 will collate information regarding the body parameters and intervention status of the subject and the measurement profile selected, and use this to derive rules used in future profile selection. Such heuristic algorithms are known in the art and will not be described in any further detail.

In any event these techniques allow different measurement profiles to be selected based on factors such as the age, height, weight, race, sex or the like, of the subject, as well as the current intervention status.

A further feature that can be implemented is to allow the first processing system 10 to access one or more remote databases, which may form one of the peripheral devices 4, to determined information regarding the subject. This can include information such as the body parameters, and details of any interventions or the like.

In this instance, when the operator is required to provide subject information, either before or following profile selection, the operator can select a search database option allowing the subject information to be retrieved. This is typically performed on the basis of a subject identifier, such as a unique number assigned to the individual upon admission to a medical institution, or may alternatively be performed on the basis of name or the like. Such a database is generally in the form of an HL7 compliant remote database, although any suitable database may be used.

In one example, the subject can be provided with a wristband or the like which includes coded data indicative of the subject identifier. In this case, the measuring device 1 can be coupled to a peripheral device 4 for determining the subject identifier. Thus, for example, the data may be in the form of a barcode, with the peripheral device 4 being a barcode scanner. It will be appreciated however that any suitable mechanism could be used for encoding the subject identifier such as RFID (Radio Frequency ID) tags could be used, in which case the peripheral device will be a corresponding reader. In this example, the barcode reader detects the barcode provided on the subject's wrist band, and determines a subject identifier from the detected barcode. The barcode reader provides data indicative of the sensed subject identifier to the first processing system 10, thereby allowing the first processing system 10 to access the subject record from the database as described above.

In any event, the first processing system 10 displays an indication of the required information, or an appropriate database search screen at step 610, allowing the operator to provide or retrieve subject information at step 615.

Once the required information is provided, the first processing system 10 operates to determine a measurement procedure at step 620. The measurement procedure will be determined from the profile and is typically in the form of a sequence of measurements that need to be made.

The profile will also include an indication of electrode placements for each of the measurements, together with details of the required current sequence that must be applied to each electrode configuration in order for the necessary measurements to be collected.

At step 625, the first processing system 10 displays an indication of the required electrode positions allowing the operator to position the electrodes on the subject at step 630. At step 635 the first processing system 10 determines and displays an indication of a lead connection. The lead connection represents the next body segment to be measured and this is achieved utilising a suitable representation described in more detail below.

Typically, for example, this may be achieved using four leads corresponding to two current leads, and two voltage leads, with each lead having a respective colour. The display highlights particular electrode positions in an appropriate colour thereby allowing the operator to connect each lead to the corresponding electrode at step 640.

Once this has been performed the first processing system 10 determines a current sequence which is to be applied to the subject and causes this to be generated utilising the processing module, which in this example is an second processing system 17.

In this example, the operation of the second processing system 17 can be controlled using instructions provided by the first processing system 10. The instructions could be in any one of a number of forms, and may correspond to firmware, embedded systems, software, or the like. In the event that firmware is used, this may be either provided by the first processing system 10, or retrieved from an internal or external memory by the second processing system 17 as required, based on instructions from the first processing system 10.

In any event, the instructions specify the configuration of the second processing system 17 thereby allowing the impedance measurements to be correctly made and subsequently analysed. It will therefore be appreciated that the instructions will depend on the selected impedance measurement profile selected above. It will be appreciated that if firmware is used, this may reside in flash memory (not shown), in the memory 21, or may be downloaded from an external source via the external interface 23.

At step 645 the second processing system 17 measures the current through and/or voltage across the electrodes for each of the applied current frequencies $f_i$ before confirming that the measurement is completed at step 650.

Once the particular measurement sequence for a given electrode position has been completed the measuring device 1 operates to determine if further measurements are required at step 655. In the event that further measurements are required the process returns to step 635 to allow the measurements to be performed.

If no further measurements are required, then processing of the impedance measurements is performed based on the selected measurement type. The analysis may be performed either in the first processing system 10, or the second processing system 17, or in a combination of the second processing system 17 or the first processing system 10, depending on the preferred implementation. In either case, the software implemented by the first processing system 10, or the firmware used by the second processing system 17 will typically be selected based on selected impedance measurement type and will therefore be indicated in the impedance measurement profile.

As a result, from the operator's perspective, the operator need only select a respective profile to perform an impedance measurement and obtain a result. In particular, the first processing system 10 uses the selected profile to determine the sequence of measurements that need to be performed, operates to instruct the operator in locating the electrodes and then connecting these in the necessary sequence.

The first processing system 10 can also determine from the profile, the software and/or firmware which is needed to perform the analysis, allowing this to be downloaded into the first processing system 10 and/or the second processing system 17 as required. Consequently, the measuring device 1 can automatically determine the required processing to be performed on the impedance measurements, allowing a result to be presented directly to the operator, thereby obviating the need for the operator to provide any input during the process.

An example of the process as used for determining the presence, absence or degree of oedema in a subject's limbs will now be described. In this regard, oedema is a build-up of fluid in a particular limb. Accordingly, in this example, by measuring the impedance of the limb it is possible to determine information regarding fluid levels and hence determine the presence or absence of oedema.

The manner in which this is achieved is heavily dependent on which limbs are effected and whether reference values are available.

For example, oedema typically occurs after an injury has occurred or surgery has been performed. Accordingly, if it is possible to perform a measurement of the limb prior to surgery, analysis of the impedance after surgery can be used to detect the onset of oedema. However, if no such measurement has been made, it is necessary to use an alternative reference to determine whether the current fluid levels are indicative of the presence of oedema.

In the case of unilateral oedema this can be achieved by comparing the impedance measurements from one limb to those obtained from the other corresponding contra-lateral limb. Thus, if it suspected that a subject might have oedema in their left arm, the impedance measurements obtained for the left arm are compared to those from the right arm.

In the event that neither longitudinal data, nor a corresponding reference limb, is available, it is then necessary to perform measurements in which different limbs are compared, and this requires the use of indices to counteract for the effect of different inherent fluid levels in different limbs.

Figure 7A:
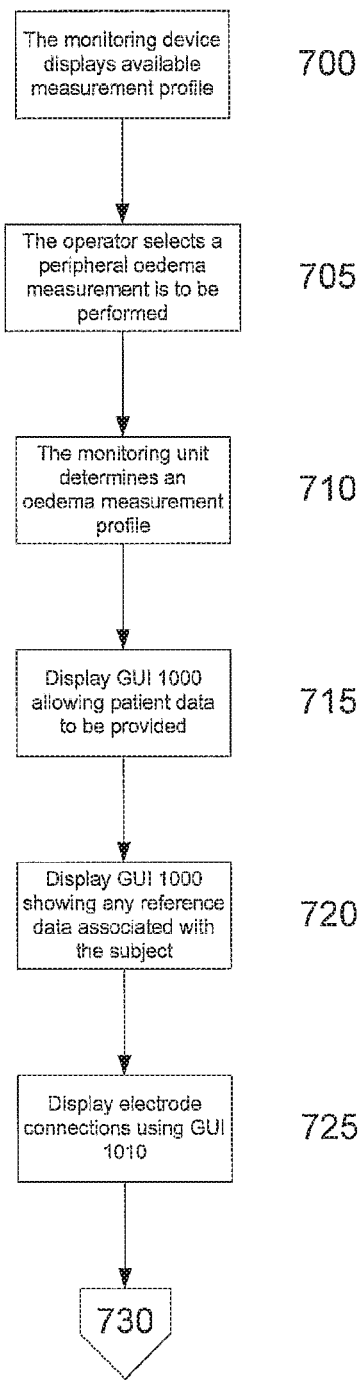
FIGS. 7A to 7C are a flow chart of an example of a process for oedema analysis.
Figure 7B:
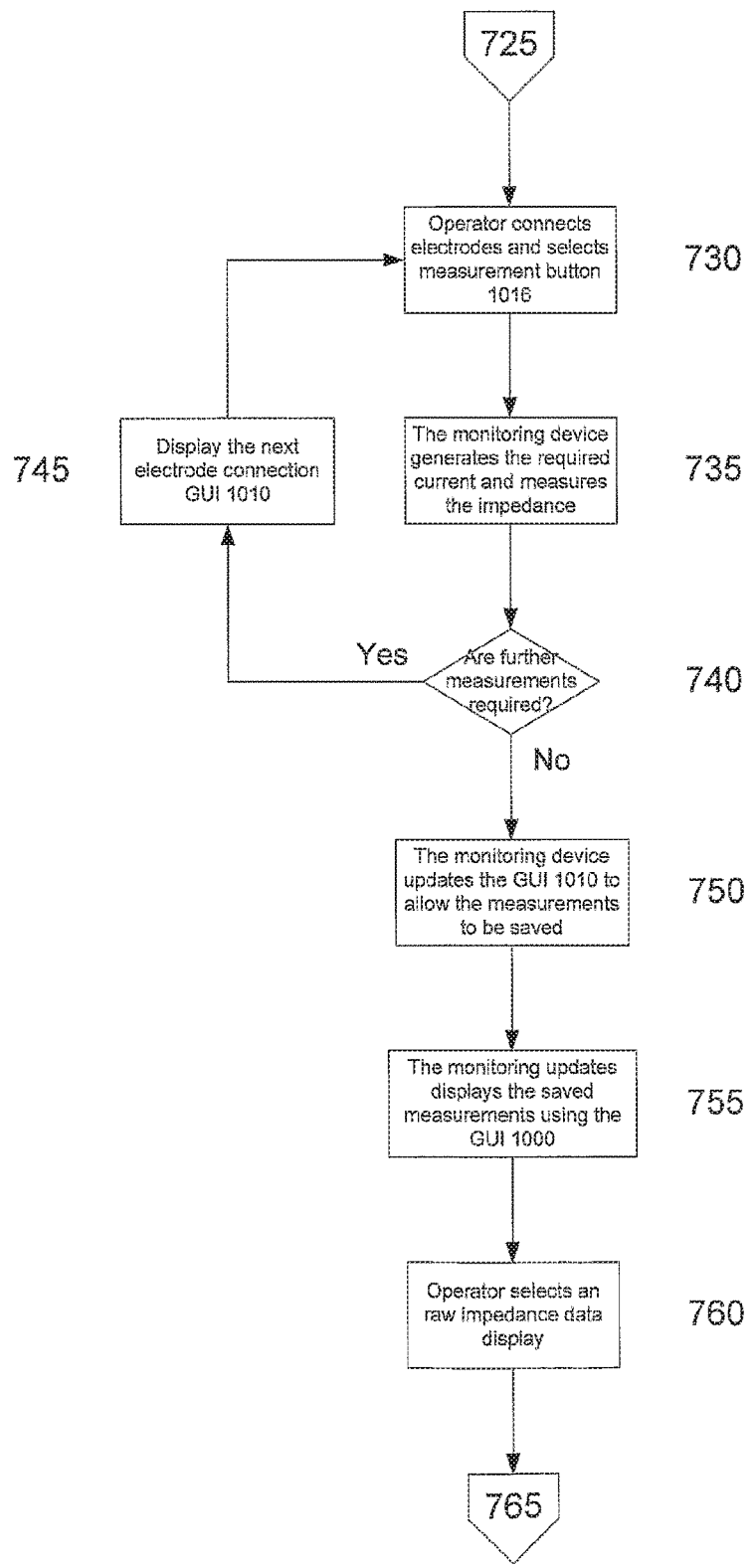
Figure 7C:
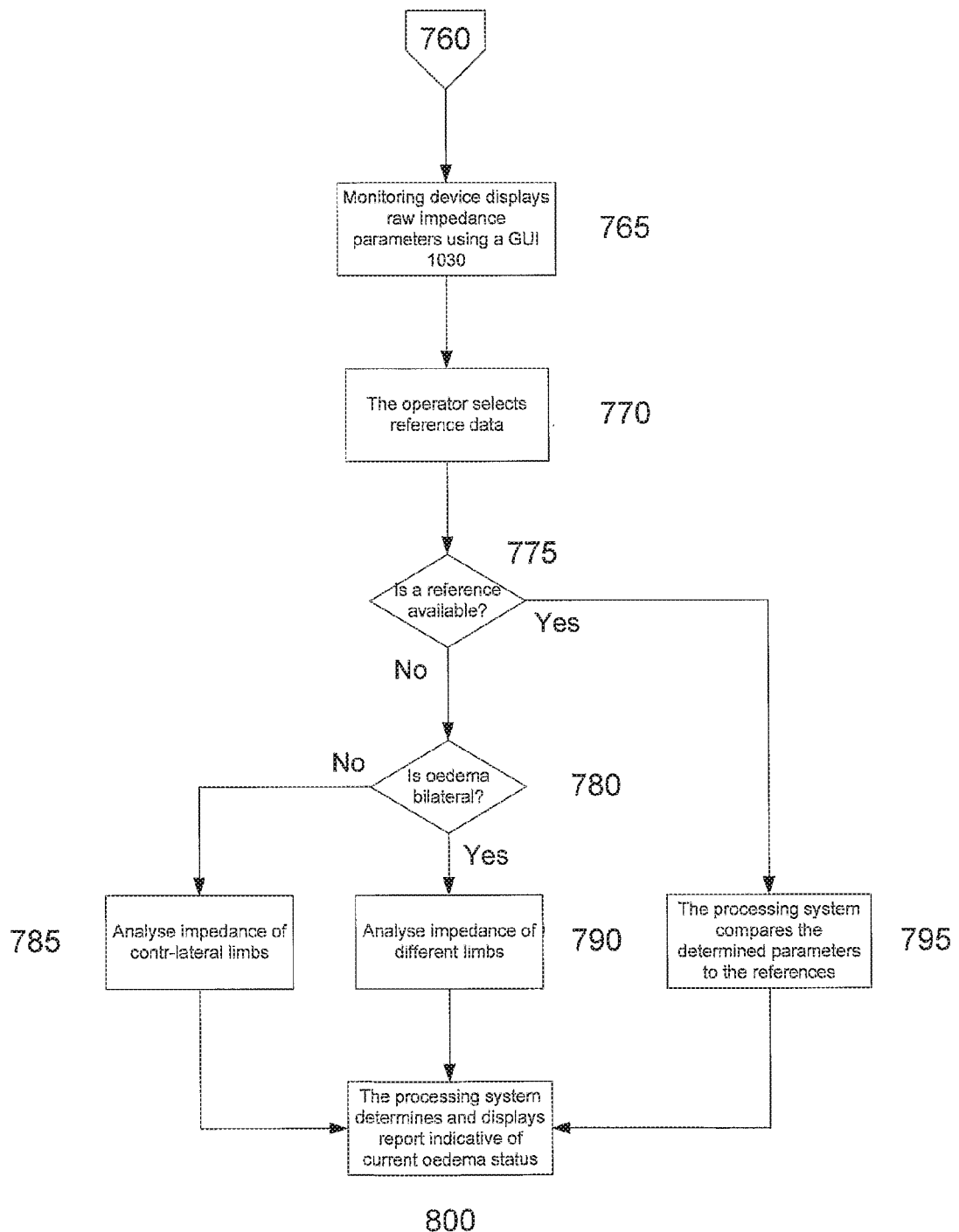

An example of the process for allowing oedema measurements to be made will now be described with reference to the flowchart shown in FIGS. 7A to 7C and with reference to the graphical user interface (GUI) screen shots shown in FIGS. 8, 9, 10 and 11.

Initially, at step 700 an operator of the monitoring device 1 views available measurement profiles displayed by the measuring device 1. At step 705 the operator selects a peripheral oedema measurement, with the first processing system 10 operating to select an appropriate oedema measurement profile, typically from the memory 21, at step 710. At this stage, the first processing system 10 may download appropriate firmware into the second processing system 17, allowing the correct current sequences to be generated, and the measured potentials to be analysed.

At step 715 the measuring device 1 displays a GUI 1000 as shown in FIG. 8A. The GUI includes a number of fields, shown generally at 1001, which allow data regarding the individual to be provided. The data includes name information such as name, address, sex, height, weight or the like. Additionally, an indication of the limbs at risk from oedema can be input as shown at 1002.

This is used to create a subject record, which is typically stored in a subject database accessed via the external interface 23, or the like. The subject record includes the subject data, and details of any performed impedance measurements for the respective subject, thereby allowing the subject record to form a subject history for use in longitudinal analysis. Thus, it will be appreciated that in the event that a record already exists for the current subject, then the operator can perform a search to retrieve the record from the database.

The database is typically a HL7 compliant remote database, and it will therefore be appreciated that the database may be the same database from which the subject details are retrieved, as described above with respect to step 705.

Once this information is provided, the processing system will update the GUI 1000 at step 720, as shown in FIG. 8B to display any previously measured impedance values, which may be used as reference data, as will be described in more detail below. Searching, editing and creation of records using the input controls shown generally at 1004.

Figures 9A, 9B, 9C:
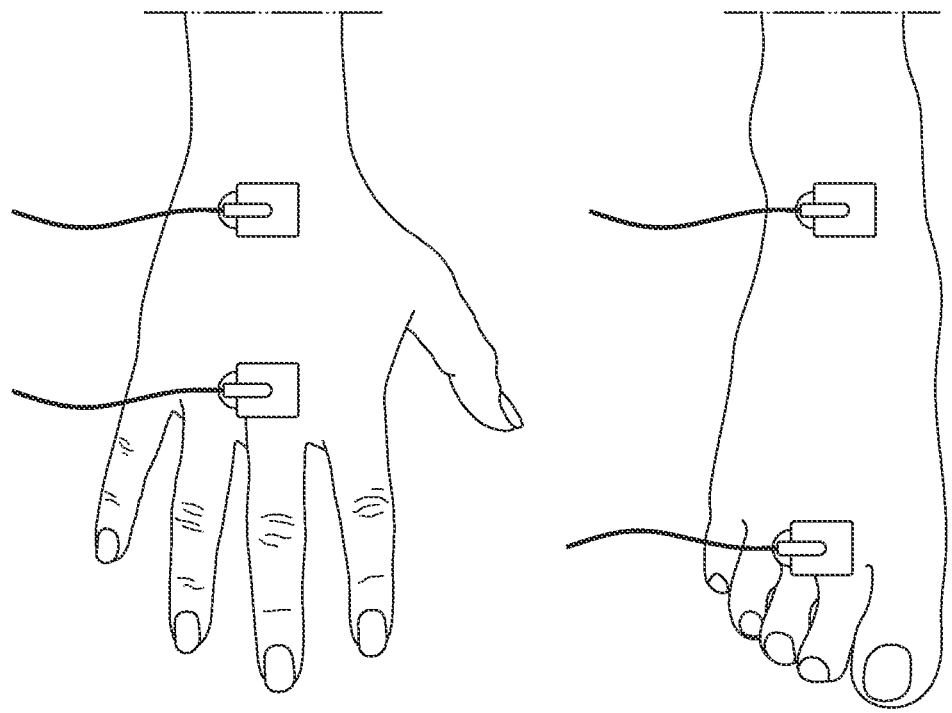
FIG. 9A is an example of a GUI used in providing electrodes on a subject.
FIGS. 9B and 9C are examples of typically electrode placements.

At step 725 the first processing system 10 generates a GUI 1010, an example of which is shown in FIG. 9A, and which is used in allowing the operator to provide electrode connections. In this example, the GUI 1010 includes an indication of subject details at 1011. A representation 1012 of the subject is provided, which shows general electrode connection points 1012A, indicating where on the subject electrodes should be provided.

The general arrangement is to provide electrodes on the hand at the base of the knuckles and between the bony protuberances of the wrist, as shown in FIG. 9B, and on the feet at the base of the toes and at the front of the ankle, as shown in FIG. 9C.

The GUI 1010 also displays details for each limb at 1017A, 1017B, 1017C, 1017D, including an indication of whether the limb is an at risk limb. This is also shown on the representation 1012 at 1017E.

An instruction field is shown generally at 1018 is provided to display instructions to the operator, with an indication of the selected measurement procedure being shown at 1019, and general measuring device status information being provided at 1020. A comments field 1021 can also be used to record comments regarding the measurements made.

At this stage the operator typically updates the weight of the subject in the subject details 1011, which may undergo significant variations over time due to changes in fluid levels within the subject's body. The operator may also respecify the at risk limbs, which is useful when a subject develops further lymphoedema. For example, a subject may start off with unilateral lymphoedema of the left leg and over time may develop a lymphoedema in the right leg. This leg can be recorded at that point as being affected by the use of the "at risk" check boxes.

Once the weight and comments are entered the measurement procedure can be initiated by clicking the "ok button" 1022. At this stage, both the weight and comments for each measurement are recorded as part of the corresponding subject record in the subject database. This allows the practitioner to track weight and clinical comments over the period of measurement.

Figures 9D, 9E:
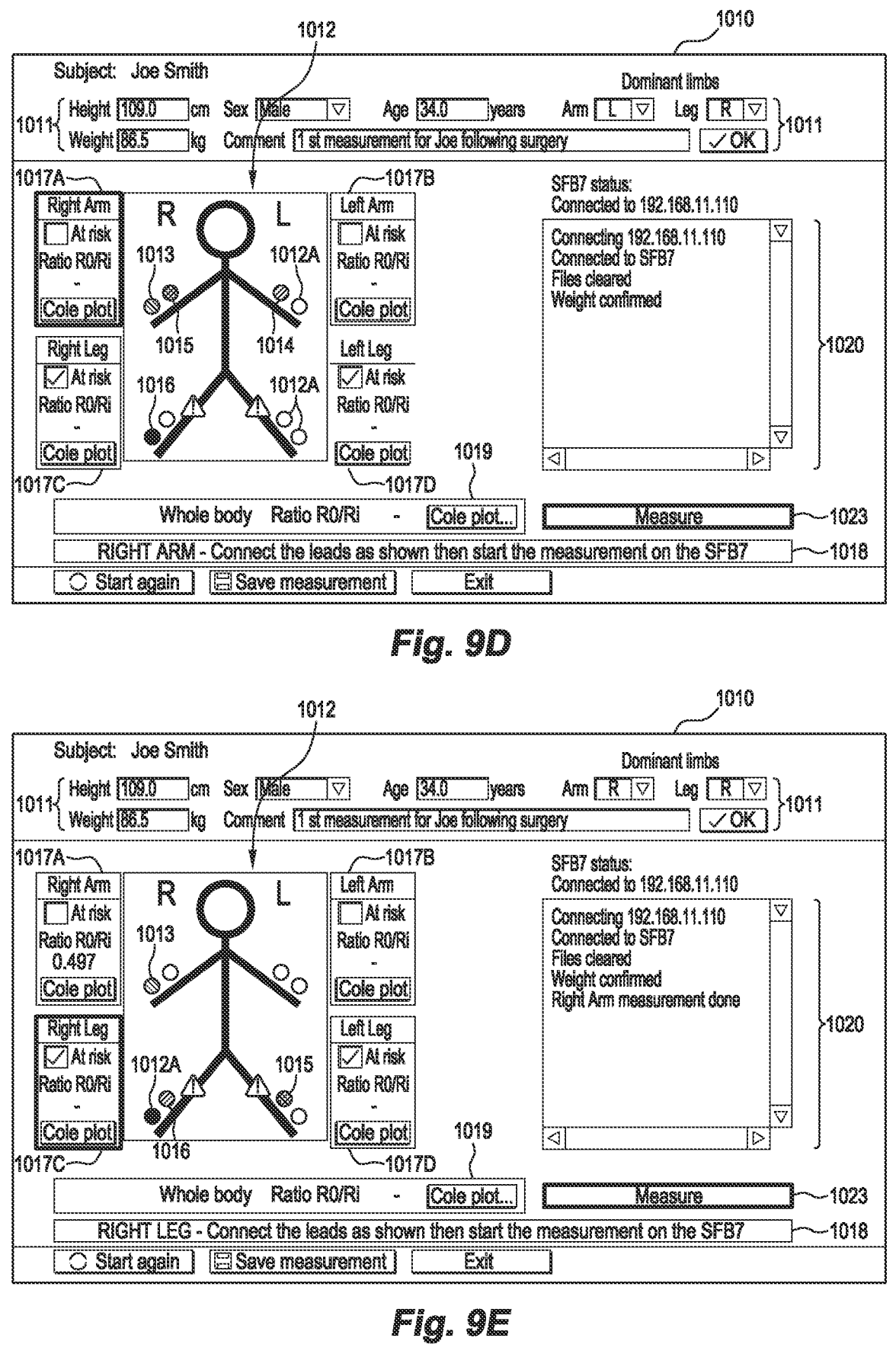

Once the ok button is clicked the electrode-lead placement GUI 1010 is updated as shown in FIG. 9D to direct the operator to connect the leads from the measuring device 1 the electrodes. In this example, the representation 1012 indicates which of the electrodes should be connected to the monitoring apparatus, as shown at 1013, 1014, 1015, 1016, to thereby form the current electrodes 13, 14, and the voltage electrodes 15, 16. This is achieved using colour coding, by using leads having colours corresponding to those shown on the representation, thereby ensure that each electrode is correctly connected to the measuring device 1.

Thus, in this example, the representation 1012 shows the electrode configuration required to measure the impedance in the right arm.

It will be appreciated that this configuration uses the theory of equal potentials, allowing the electrode positions to provide reproducible results for impedance measurements. For example when current is injected between electrodes 1013 and 1016 in FIG. 9D, electrode 1014 could be placed anywhere along the left arm, since the whole arm is at an equal potential. This is advantageous as it greatly reduces the variations in measurements caused by poor placement of the electrodes by the operator. It also greatly reduces the number of electrodes required to perform segmental body measurements, as well as allowing the limited connections shown to be used to measure each of limbs separately.

Once the leads are correctly connected the operator uses a measure button 1023 to cause the measuring device 1 to perform the impedance measurement, with general measuring device status information being provided at 1020.

Thus, it will be appreciated that the first processing system 10 determines from the profile, the next measurement to be performed, and generates the GUI including appropriate information in the representation 1012 and the instruction field 1018.

At step 730, the operator connects electrodes in accordance with the electrode connections shown on the representation 1012, and once this has been completed selects the measurement button 1023, causing the measurement to be performed.

At this point the monitoring device 1 generates the required current signal(s), and applies these to the subject, before measuring the current and voltage across the subject at step 735, to allow instantaneous impedance values to be determined at a number of different frequencies ft.

At step 740 it is determined if further measurements are required. If so, the measuring device 1 operates to update the GUI 1010, at step 745, based on the next measurement to be performed, as shown for example, in FIG. 9E.

In this example, the representation 1012 is updated to show the next required electrode connections 1013, 1014, 1015, 1016, which in this case correspond to performing measurements on the right leg.

Additionally, the first processing system 10 will also display preliminary results from the completed measurement. Thus, in this example, as the right arm has already been measured, an impedance parameter indication is shown at 1017A, in FIG. 9E.

Figures 9F, 9G:
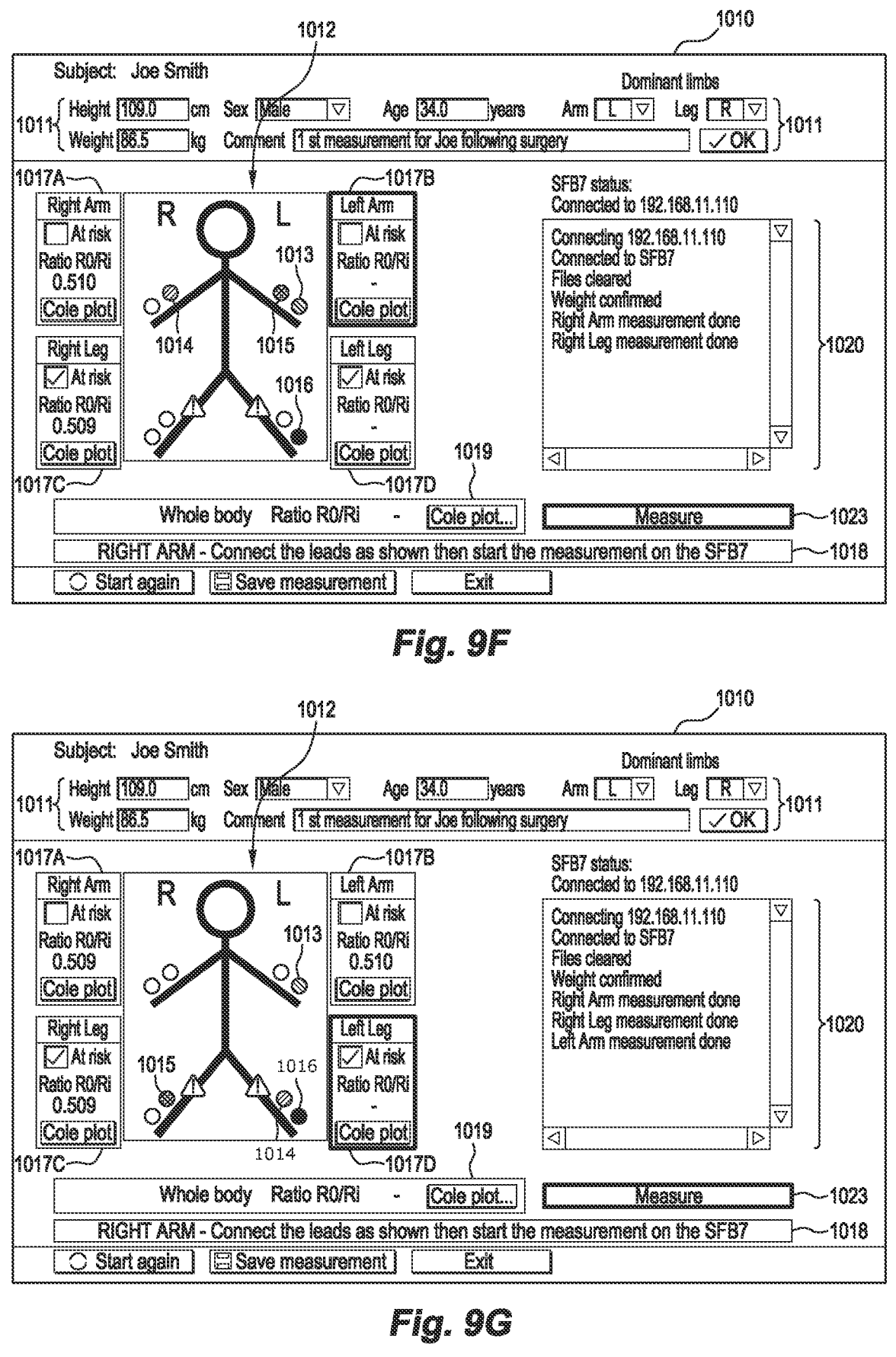

Steps 730 to 745 are then repeated as required, which in this case involves performing at least four sets of measurements, one for each limb, as shown in FIGS. 9F and 9G.

Figures 9H, 9I:
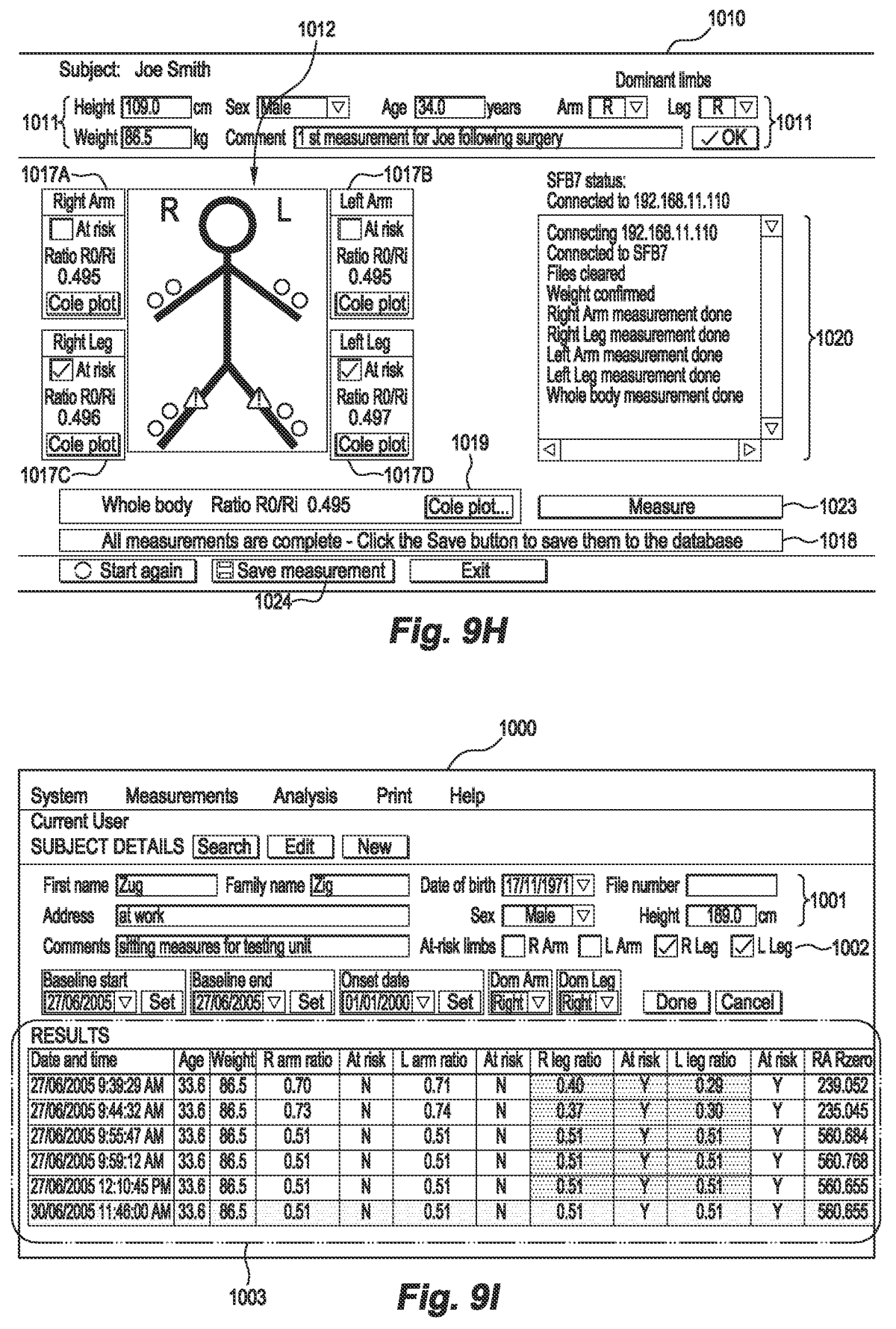

Once no further measurements are required the process moves on to step 750 with the monitoring device updating the GUI 1010 to indicate that the measurement process is completed 1018, and that the measurements can be saved using the button 1024, as shown in FIG. 9H. At this point, the first processing system 10 can update the GUI 1000 to reflect the saved measurements as shown in FIG. 9I, at step 755.

At this point the operator can review the measured impedances as well as analysing the impedances to determine the onset of oedema.

In this example, at step 760 the operator selects raw impedance data display. At step 765, the first processing system 10 displays the raw impedance parameters utilising a GUI 1030. In this example, the GUI includes subject details at 1031, and a measurement selection inputs 1032. This allows the operator to select measurements of interest, which in this example includes measurements from the left arm.

Once the measurements are selected, the first processing system 10 displays an overview of parameters determined from the impedance measurements at 1033.

The parameters derived will depend on the analysis being performed and will typically include parameters such as the impedance at zero, characteristic and infinite frequencies ($R_0$, $Z_c$, $R_\infty$). These can be derived based on the impedance response of the subject, which at a first level can be modelled using the equation (1), known as the Cole model, in which:

$$Z = R_\infty + \frac{R_0 - R_\infty}{1 + (j\omega\tau)} \quad (1)$$

where:
$R_\infty$=impedance at infinite applied frequency,
$R_0$=impedance at zero applied frequency,
$\omega$=angular frequency,
$\tau$ is the time constant of a capacitive circuit modelling the subject response.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^{(1-\alpha)}} \quad (2)$$

where $\alpha$ has a value between 0 and 1 and can be thought of as an indicator of the deviation of a real system from the ideal model.

The value of the impedance parameters $R_0$ and $R_\infty$ may be determined in any one of a number of manners such as by:
solving simultaneous equations based on the impedance values determined at different frequencies;
using iterative mathematical techniques;
extrapolation from a "Wessel plot";
performing a function fitting technique, such as the use of a polynomial function.

At this stage the first processing system 10 can also be adapted to test adherence of the measurements to the Cole model. In particular, the Cole model assumes that the impedance measurements lie on a semi-circular impedance locus. Accordingly, the first processing system 10 can determine if the measured values fit a semi-circular locus to thereby determine if the Cole model is satisfied. Alternatively, the measured impedance parameter values can be compared to theoretical values derived using the equation (2), to thereby allow the degree of concordance to the Cole model to be determined.

In the event that the Cole model is not satisfied, an indication of this can be provided to the operator allowing an appropriate analysis technique to be utilised.

Figure 10A:
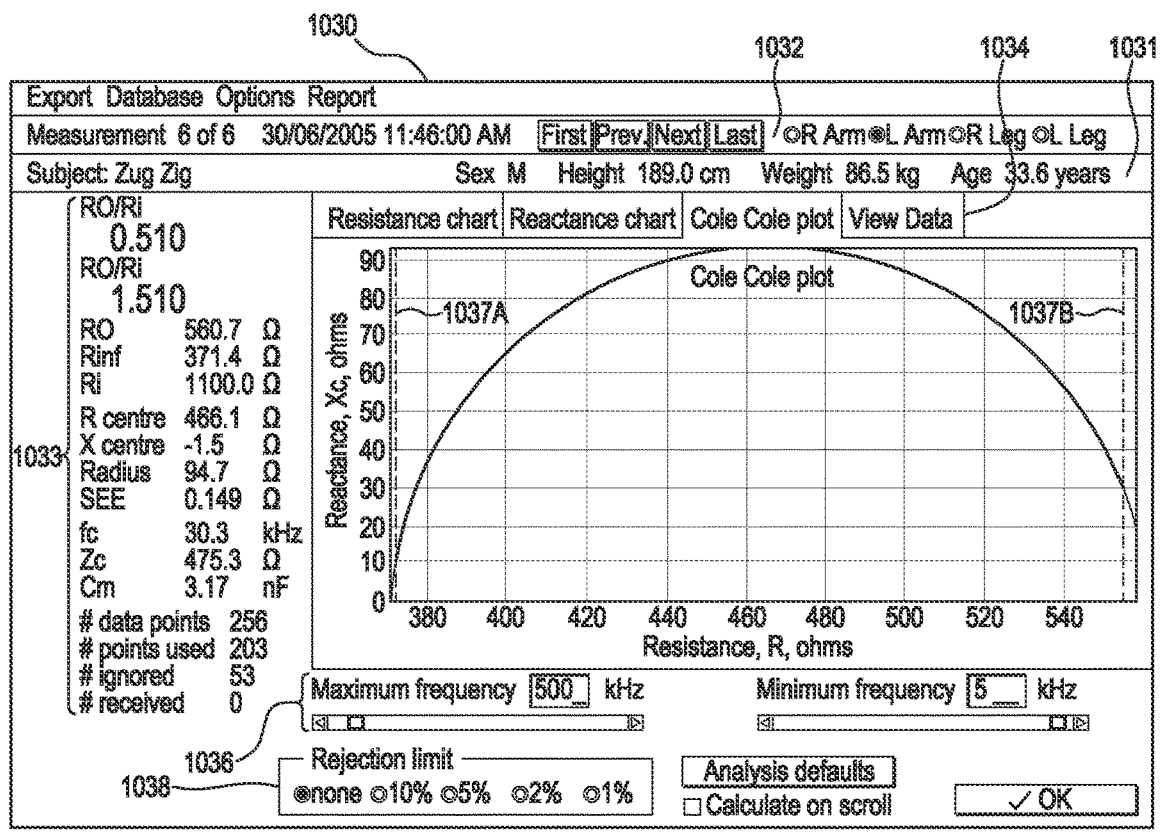
FIGS. 10A to 10D are examples of a GUI used in viewing measured impedance parameters.
Figure 10B:
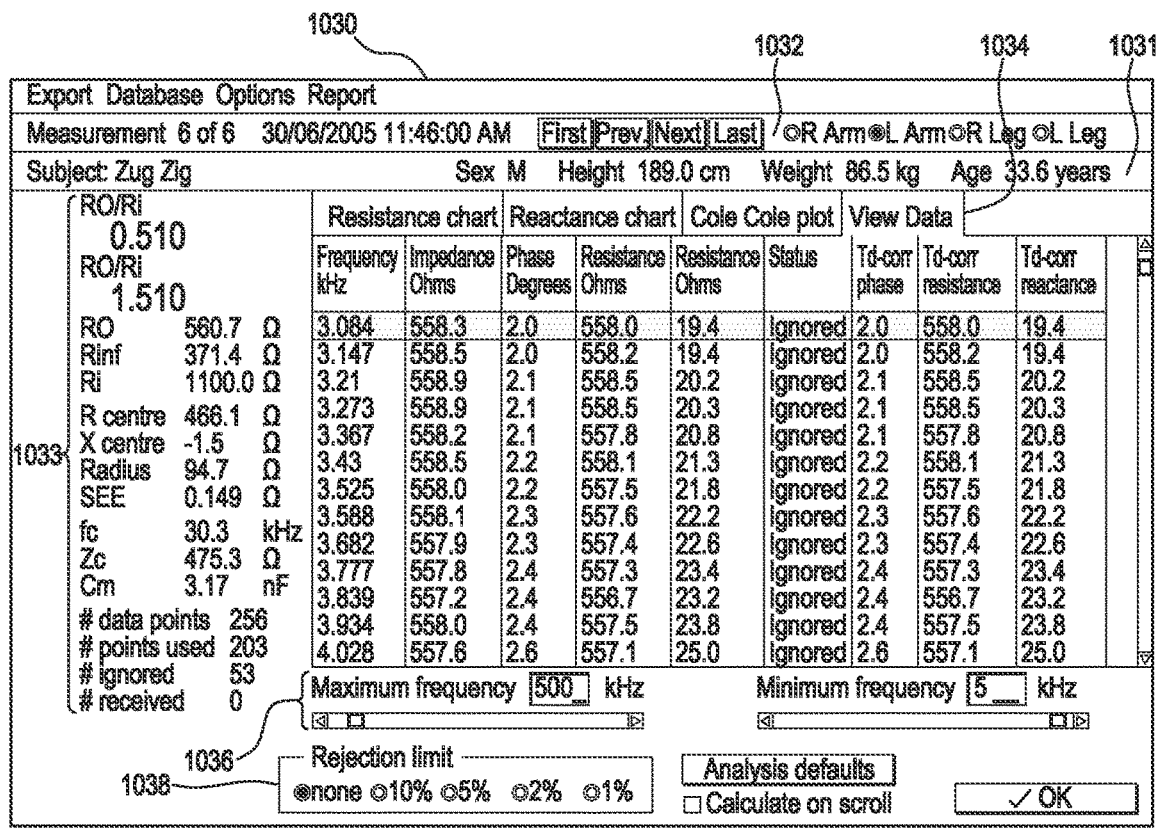
Figure 10C:
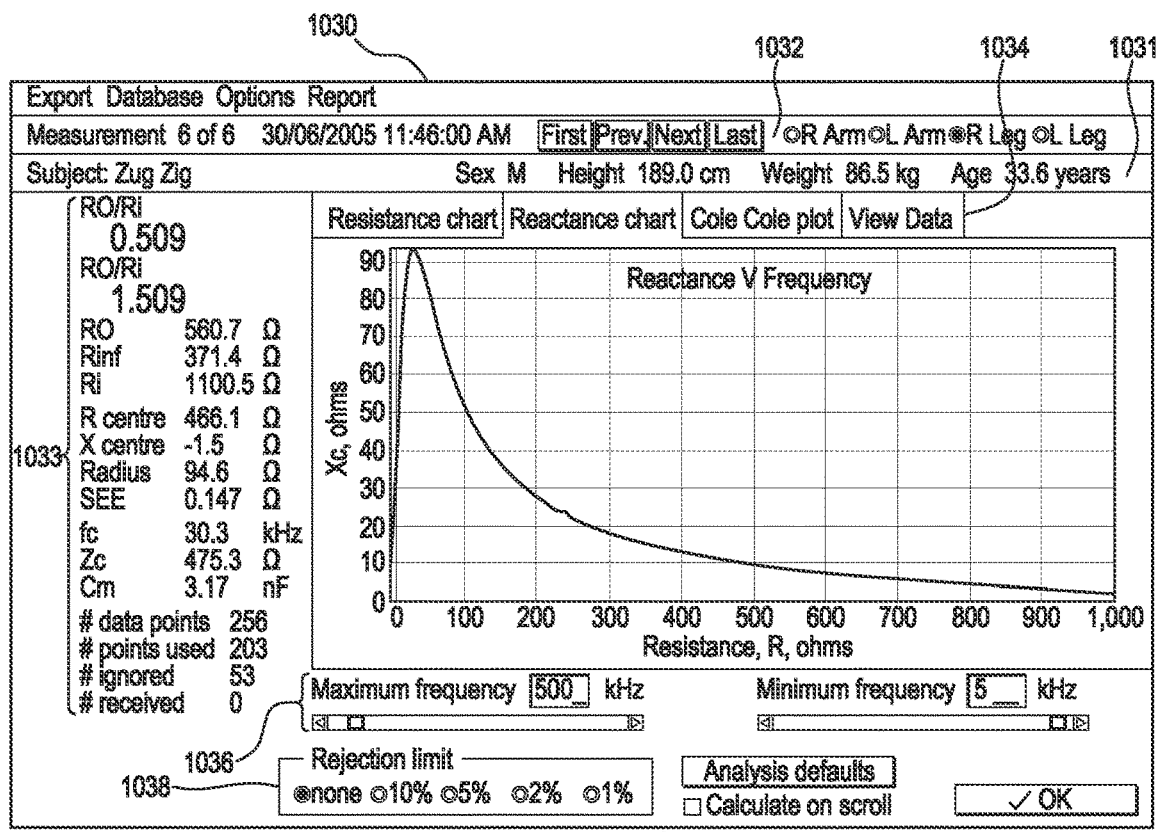
Figure 10D:
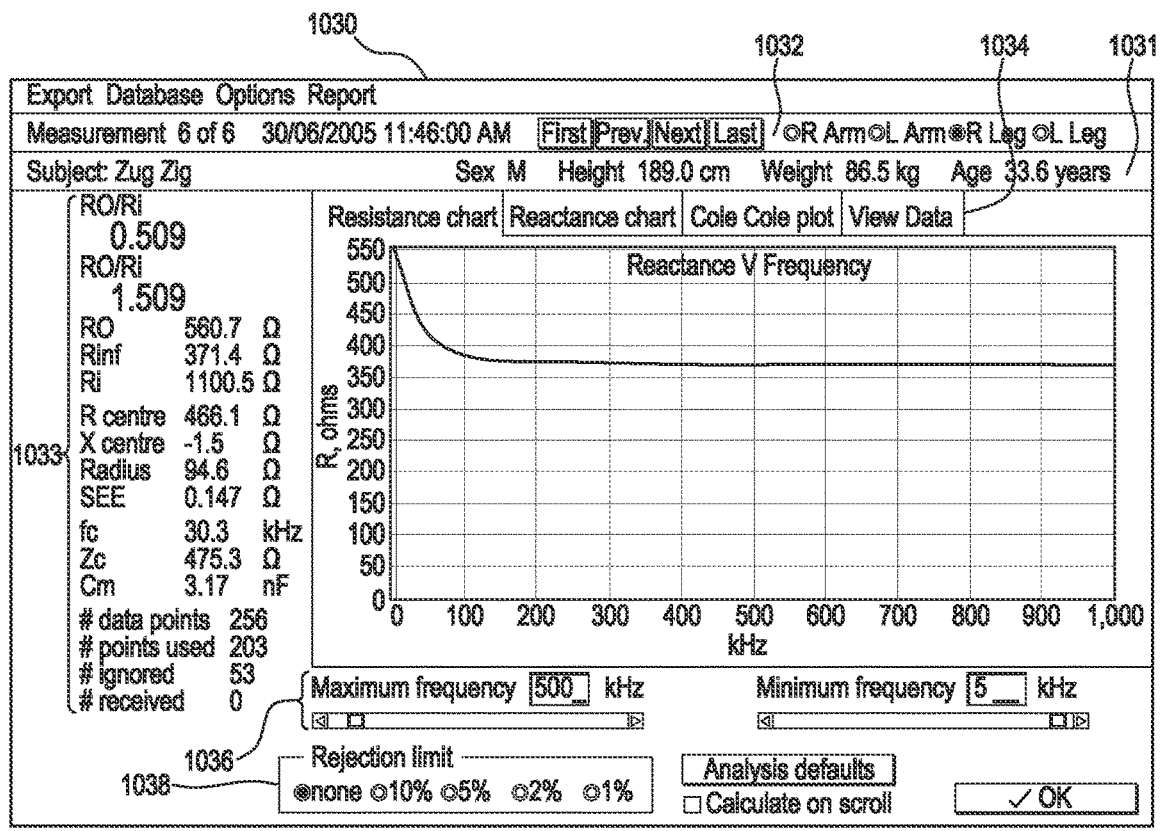

Once the parameters have been determined, and displayed, a number of tabs 1034 can be used to allow different representations of the measured impedance values to be provided in a window 1035. This includes, for example, producing a "Wessel" type plot, also commonly referred to as a Cole-Cole plot, as shown in FIG. 10A. Alternatively the impedance values can be listed as shown in FIG. 10B, or plotted as reactance verses frequency or resistance verses frequency as shown in FIGS. 10C and 10D respectively.

Frequency controls 1036 are provided to allow impedance measurements above or below threshold limits to be omitted from the displayed results, as shown by threshold markers 1037A, 1037B. Additionally a rejection limit can be applied to discard data points that fall outside a threshold variation from an idealised semi-circular locus provided on the "Wessel" plot.

At step 770, the operator selects any references to be used. The reference will typically be in the form of earlier data collected for the respective subject, thereby allowing a longitudinal analysis to be performed.

However, the system may also or alternatively use a normal population database table, which includes reference values obtained from different subjects. This database table is essentially a single subject database table into which all measurements of normal population subjects (people without lymphoedema) are added.

An example of such normal population data displayed using the GUI 1000 is shown in FIG. 11A. This table then acts as a pool of data from which normalised values for raw impedance data and ratios of impedance data can be generated, allowing comparison with measured values for the subject to be performed.

This generation of this normalised data is in the form of mean (averaged) values that are selected to be relevant to the test subject. The selection is performed based on the subject information and may be performed on the basis of any one of a number of factors, such as age, sex, height, weight, race, interventions, or the like.

Therefore if the test subject has unilateral lymphoedema of the dominant arm and is female then the normalised data drawn from the normal population database will be calculated from the dominant arm measurements from female subjects that are present in the in the normal population database.

Accordingly, at step 775, the operator is presented with a GUI 1040 similar to that shown in FIG. 11A, which allows the operator to select appropriate records from the normal population table, as shown by the highlighted entry at 1041.

In the case of using a subject specific reference, this is generally achieved by ensuring measurements taken prior to surgery or events that put them at risk of developing lymphoedema. A common example is baseline measurements taken before surgical intervention for breast cancer that can be use to track subjects fluid shifts post surgery by comparison of study measurements to these baseline generated mean values.

Subject specific baselines can be generated automatically from measurements in the subject's database table. This can be achieved using the GUI 1000 shown in FIG. 11B, in which the subject's record is displayed. Located on the GUI 1000 are two selection windows 1042, 1043 that are used to define the measurements used from the subject's database table to generate mean data values for comparison to study measurements.

It will be appreciated that the process can also be used to add data to the normal population table. This is achieved by performing the measurement process outlined above, and in the event that the subject does not suffer from oedema, for example if surgery has not yet been performed, importing the data into the normal population table. This can be performed in addition to adding the measurements to the subject record, so that measurements collected from a healthy individual can be used for subsequent longitudinal analysis and/or as a normal population reference.

At step 775 the measuring device 1 determines if a reference is available, and if so, the first processing system 10 compares the currently determined parameters to one or more reference values at step 795, and utilises this to generate reports which are displayed at step 800.

If no reference is available, it is determined whether or not the oedema is bilateral at step 780. In this instance, if the oedema is not bilateral, then the first processing system 10 can analyse the impedance of contra-lateral limbs at step 785 and provide an appropriate output at step 800. This may be achieved for example by determining an index based on a ratio of the extra- to intra-cellular fluid levels in each leg, and then comparing the values determined to assess whether there is difference between the limbs, and hence whether there is a likelihood of oedema being present.

The extracellular fluid resistance $R_e$ is determined from:

$$R_e = R_0$$

and intracellular fluid resistance $R_i$ is determined from:

$$R_i = \frac{R_\infty R_e}{R_e - R_\infty}$$

Thus, the index I, which is indicative of the ratio of extra- to intra-cellular fluid is given by the equation:

$$I = \frac{R_i}{R_e} = \frac{R_\infty}{R_0 - R_\infty} \qquad (3)$$

In the event that there is a likelihood of the oedema being bilateral, then the first processing system 10 typically determines the index for each limb. A ratio of the determined index for different pairs of limbs are then compared at step 790, thereby allowing the operator to determine if there is a likelihood of bilateral oedema.

Examples of the different types of available reports will now be described with reference to FIGS. 11C to 11H.

As shown in FIG. 11B, the report is presented using a GUI 1050 that includes subject details shown generally at 1051. The GUI includes controls 1052 that allow the operator to select whether reference data is to be used and the nature of the reference data. Thus, it will be appreciated that if a user varies the reference data selection, the process will return to step 540 to reassess the nature of the output dependent on the type of reference selected. At 1053A a drop down list is provided to indicate the nature of the parameter that is to be displayed, and at 1053B checkboxes are provided indicating the limbs for which the parameter is to be displayed. In addition to this, a limb of interest and a reference limb can be selected using the check boxes 1054, 1055 as shown.

The parameters available for charting include:
Weight;
Lymphogram;
Ratio of indices;
Ratio of body segment $R_0$ values;
The index for each individual body segment $R_0$ for a body segment;

$R_\infty$ for a body segment;

The intracellular fluid resistance $R_1$;

The characteristic frequency of the subject $f_c$;

Standard error of estimates;

Td time delay for each measurement.

Each of the parameters will now be described in more detail.

The Lymphogram

The lymphogram or impedance vector plot is a graphical representation of when a subject's measurements move relative to a reference ellipse. The reference ellipse can be generated from a 95% confidence interval based on the subject specific baseline data or the normal population data. When data points of a study body segment move outside the ellipse the subject's condition is worsening and lymphoedema is present in that body segment. The ellipse can be generated for and displayed for each body segment chosen using the reference limb checkbox. The data points displayed are those generated from the study body segment data for the subject. The study body segments and reference body segments are chosen using the body segment selector check boxes located underneath the chart.

Figure 11C:
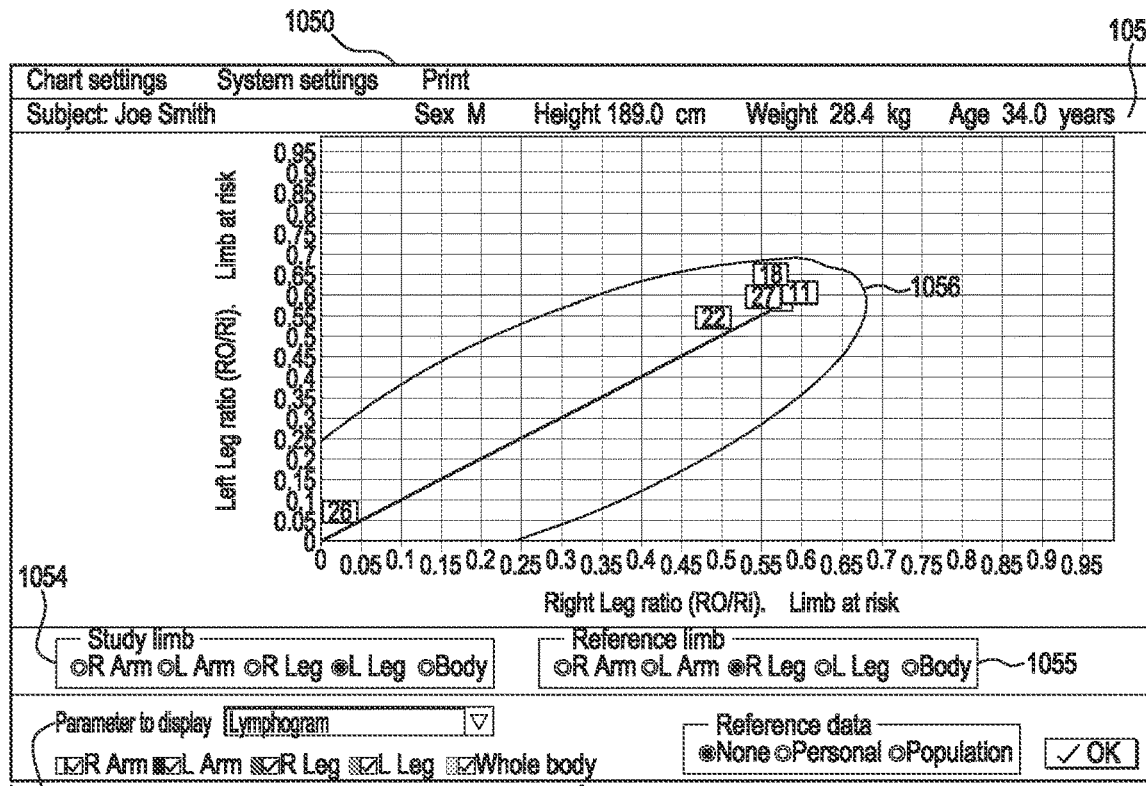
FIGS. 11C to 11H are examples of a GUI used in presenting the results of an impedance analysis.
Figure 11D:
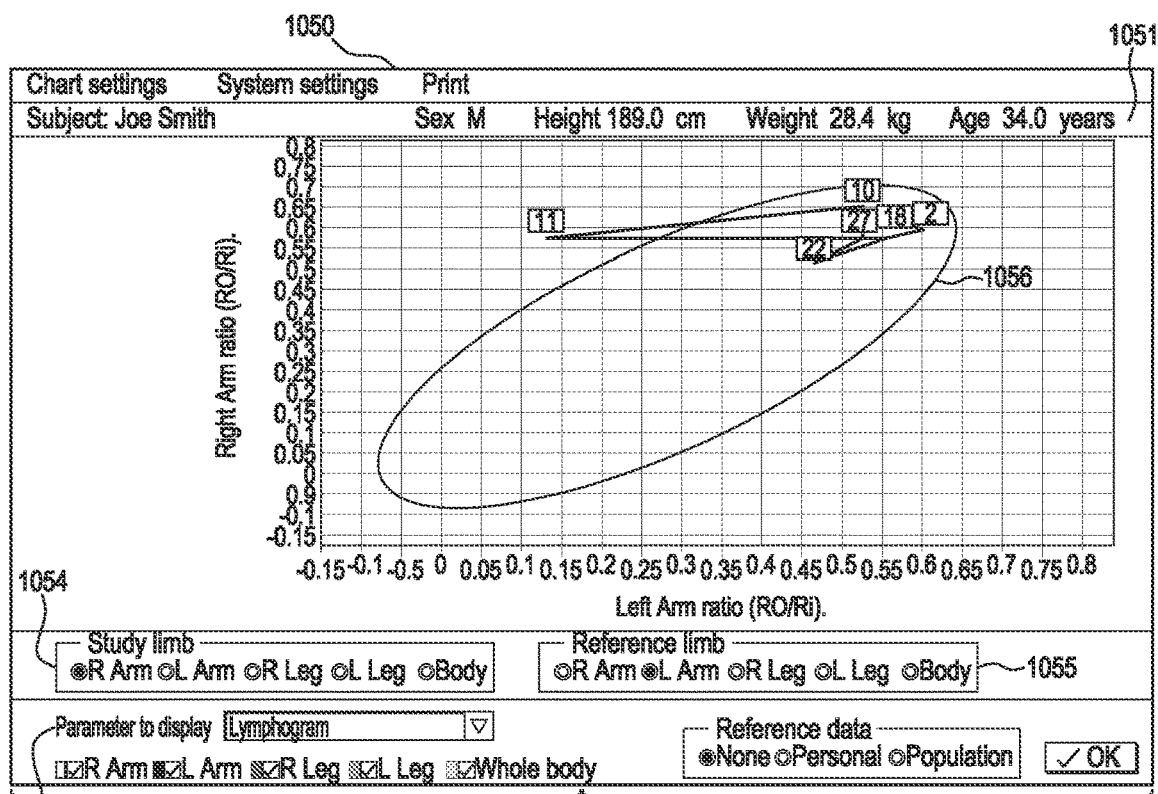

FIG. 11C shows an example of a lymphogram in which the index for left and right legs is compared. In this example, the index remains within the ellipse shown generally at 1056 highlighting that lymphoedema is not present. However, when the right arm and left arm are compared as shown in FIG. 11D, the values for the ratio comparisons fall outside the reference ellipse 1056 indicating that the right arm is suffering from oedema.

In these examples, the lymphogram includes a comparison between limbs, and accordingly, the checkboxes 1053B are not used.

Ratio of Body Segment Indices

This will display the index I for a selected reference limb divided by the index I of the limb of interest.

Figure 11E:
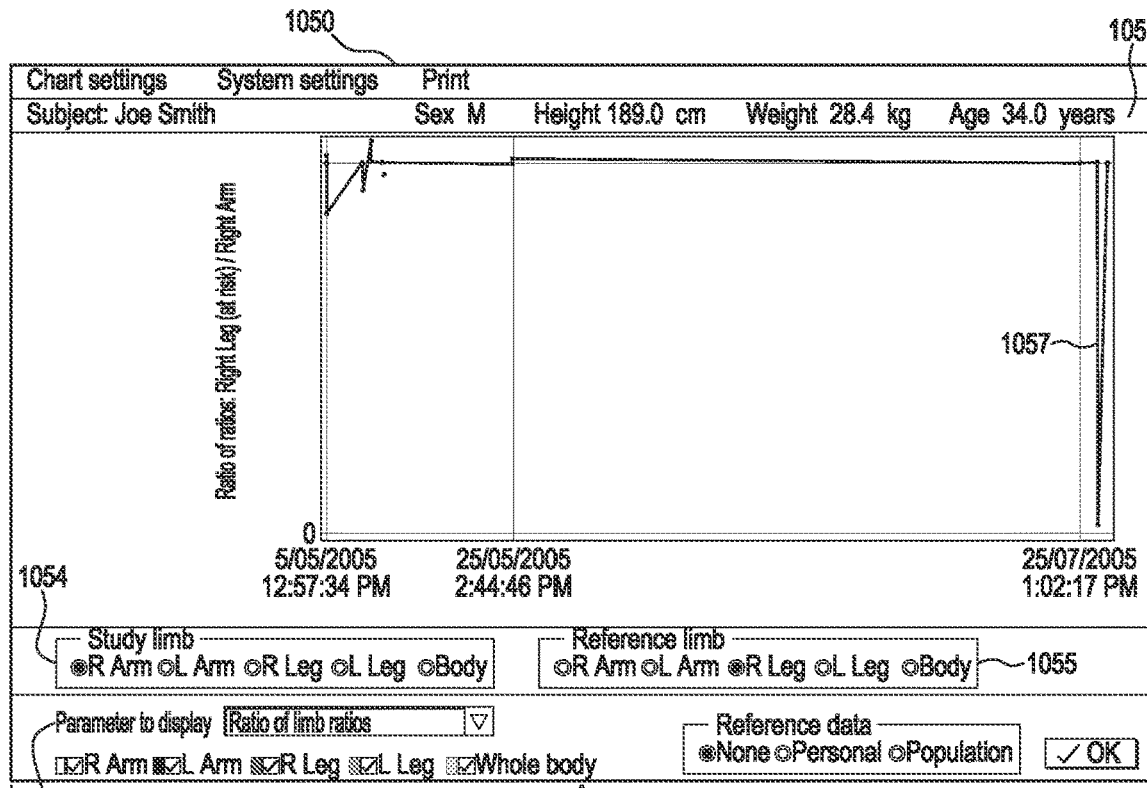

FIG. 11E is an example of the ratio of limb ratios in which a ratio of the index for the right arm and right legs is plotted against time. In this instance, it can be seen that a significant variation is present at 1057 indicating the likelihood of oedema.

In this examples, as two limbs are again compared, the checkboxes 1053B are not used, and are ignored.

Ratio of Body Segments $R_0$ Values

This function will display the ratio of the $R_0$ of the reference body segment divided by that of a study body segment for each measurement in the subject's database table.

Index I for Each Body Segment

Figure 11F:
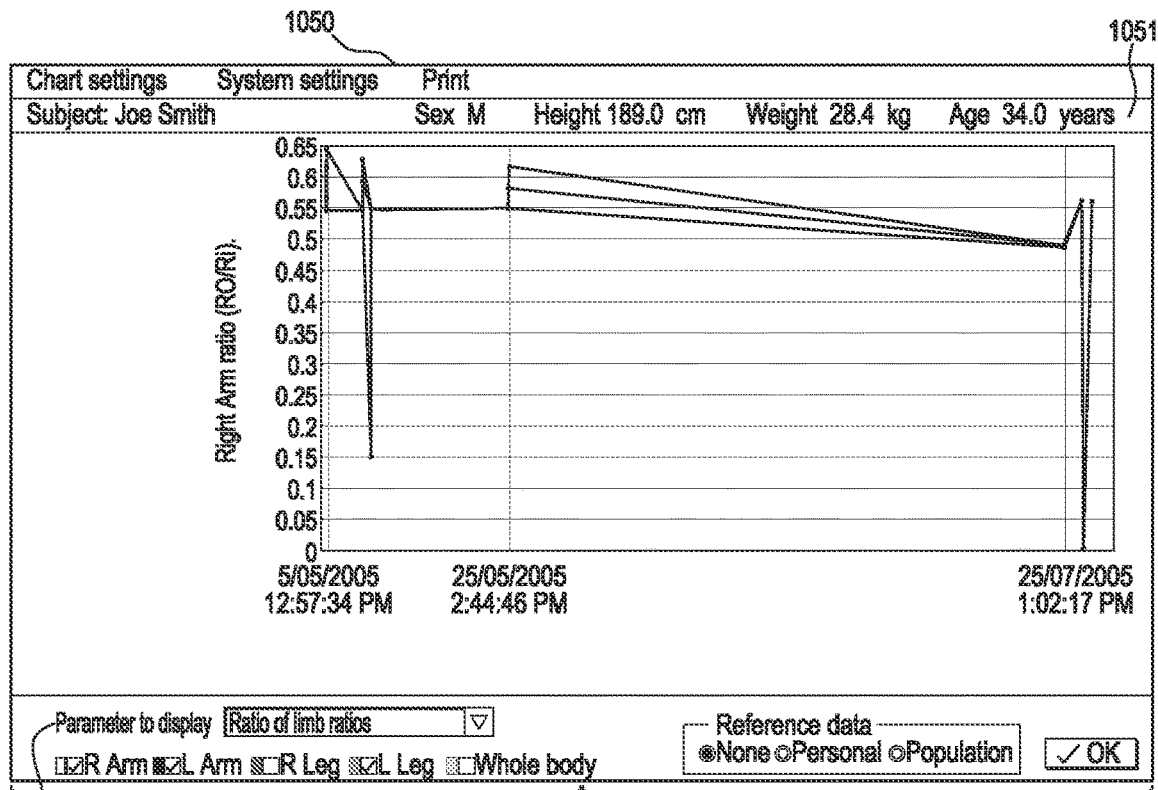
Figure 11G:
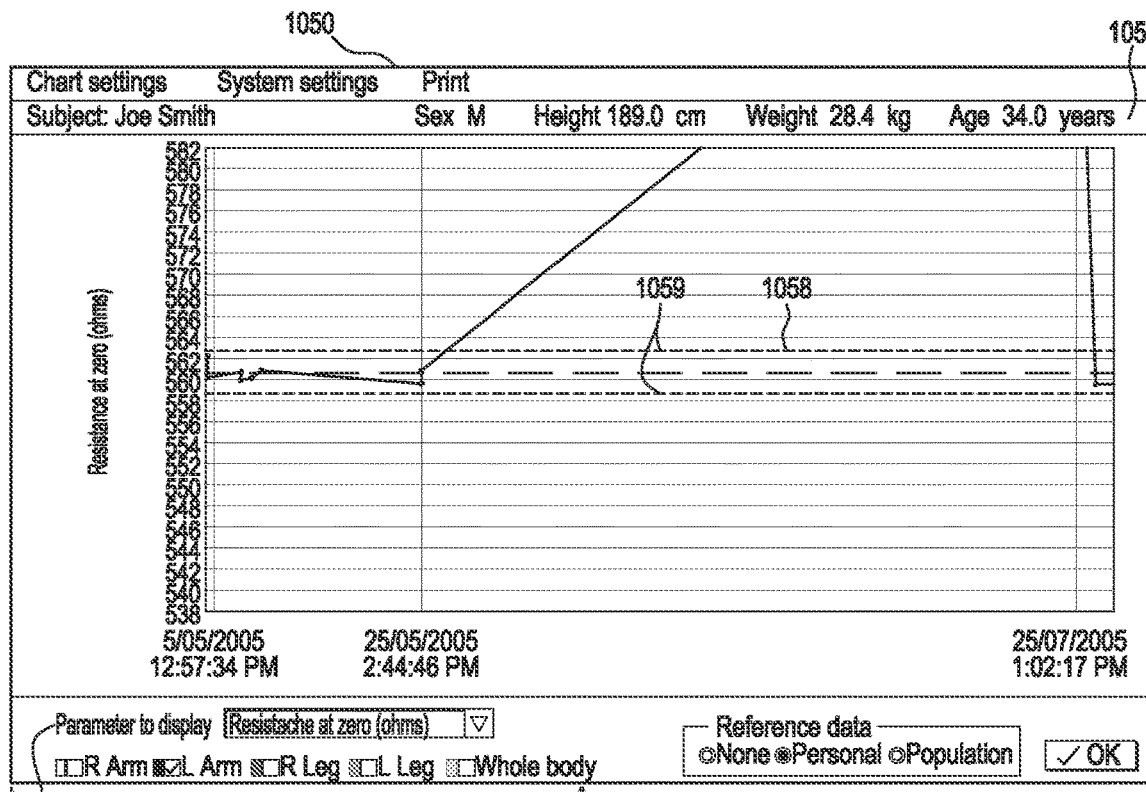
Figure 11H:
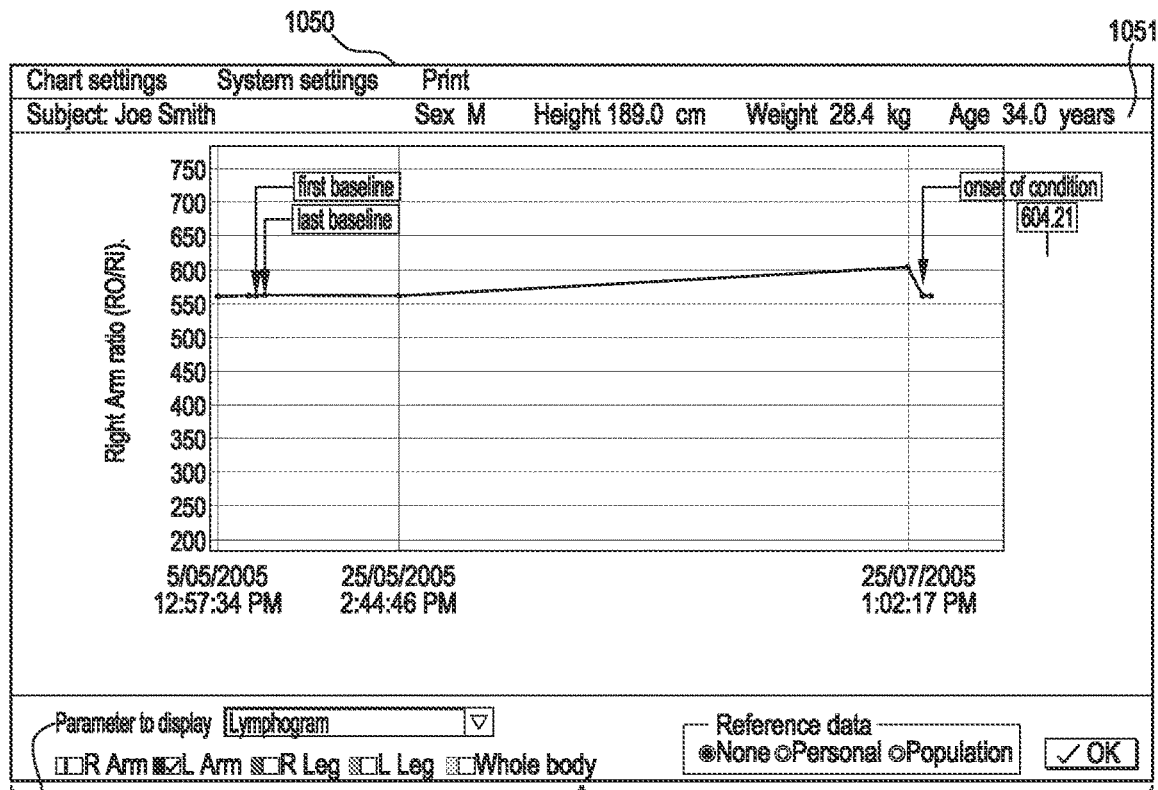

The index I can also be displayed for each body segment for all measurements in the subject's database table as a chart over time, as shown in FIG. 11F. The body segments represented on the chart are selected using the control 1053. In this instance, as reference and study limbs are not defined, the 1054, 1055 are omitted for clarity.

Resistance at Zero kHz ($R_0$) for a Single Body Segment

The value of $R_0$ can also displayed for each body segment for all measurements in the subjects database table as a chart over time.

Resistance at Infinite Frequency ($R_\infty$) for a Single Body Segment

The value of $R_\infty$ can also displayed for each body segment for all measurements in the subjects database table as a chart over time.

Resistance for the Intracellular Fluid ($R_i$) for a Single Body Segment

The value of $R_i$ can also displayed for each body segment for all measurements in the subjects database table as a chart over time.

Characteristic Frequency for Single Body Segment

The characteristic frequency can also displayed for each body segment for all measurements in the subjects database table as a chart over time.

SEE (Standard Estimate of Errors) Values for a Single Body Segment

The value of the standard estimate of errors (SEE) can also displayed for each body segment for all measurements in the subjects database table as a chart over time.

Td (Time Delay) Values for a Single Body Segment

The value of the time delay (Td) associated with each measurement can also displayed for each body segment for all measurements in the subjects database table as a chart over time.

Reference Indications

In each of the above outlined reports, reference values can also be displayed based either on the normalised population reference or subject specific reference.

An example of the use of a subject's specific reference value is shown in FIG. 11F. In this instance the reference value is based on $R_0$ as shown at 1058. Accordingly, it can be seen that variation of the value $R_0$ compared to the reference is indicative of oedema. The generation of a report by comparison to normal population data will be performed in a similar manner.

In addition to simply displaying the absolute reference value determined, it is also possible to display standard deviations as shown at 1059 to thereby provide an indication of the degree of variation from the base line.

Event Markers

A further feature of the process is the ability to associate event markers with specific measurements in the measurement database table. Event markers can provide commented time points that correspond to measurements and points in time. These can be customised by the user to indicate important events that need to be documented on the longitudinal analysis charts. Such events may include, onset date of lymphoedema, the start of massage intervention etc. These markers will be displayed automatically on the longitudinal charts that are a function over time. Event markers can also be shown on charts as shown for example in FIG. 11H.

Alternative Analysis

In the above examples, the first processing system 10 therefore selects the types of analysis or representation that is most appropriate for determining the presence or absence of oedema based on the currently available data. This therefore removes the requirement for the operator to make an assessment of which form of report would provide the most accurate indication of the onset of oedema.

In the above example, the impedance measurements are collected for each of the limbs, with the assessment of the preferred type of analysis being performed after the measurements have been performed. However, as an alternative to this, the first processing system 10 can be adapted to determine the preferred type of analysis first and then only perform the measurements required in order for the type of analysis to be performed.

Thus a limited limb analysis can be performed, in which the operator specifies the limbs for which measurements are to be made prior to the measurement process. In this instance, data will only be collected for the limbs of interest.

In addition to performing the lymphoedema measurements described above, it is possible that profiles can be configured to allow a range of different measurements to be performed.

Figures 12, 14:
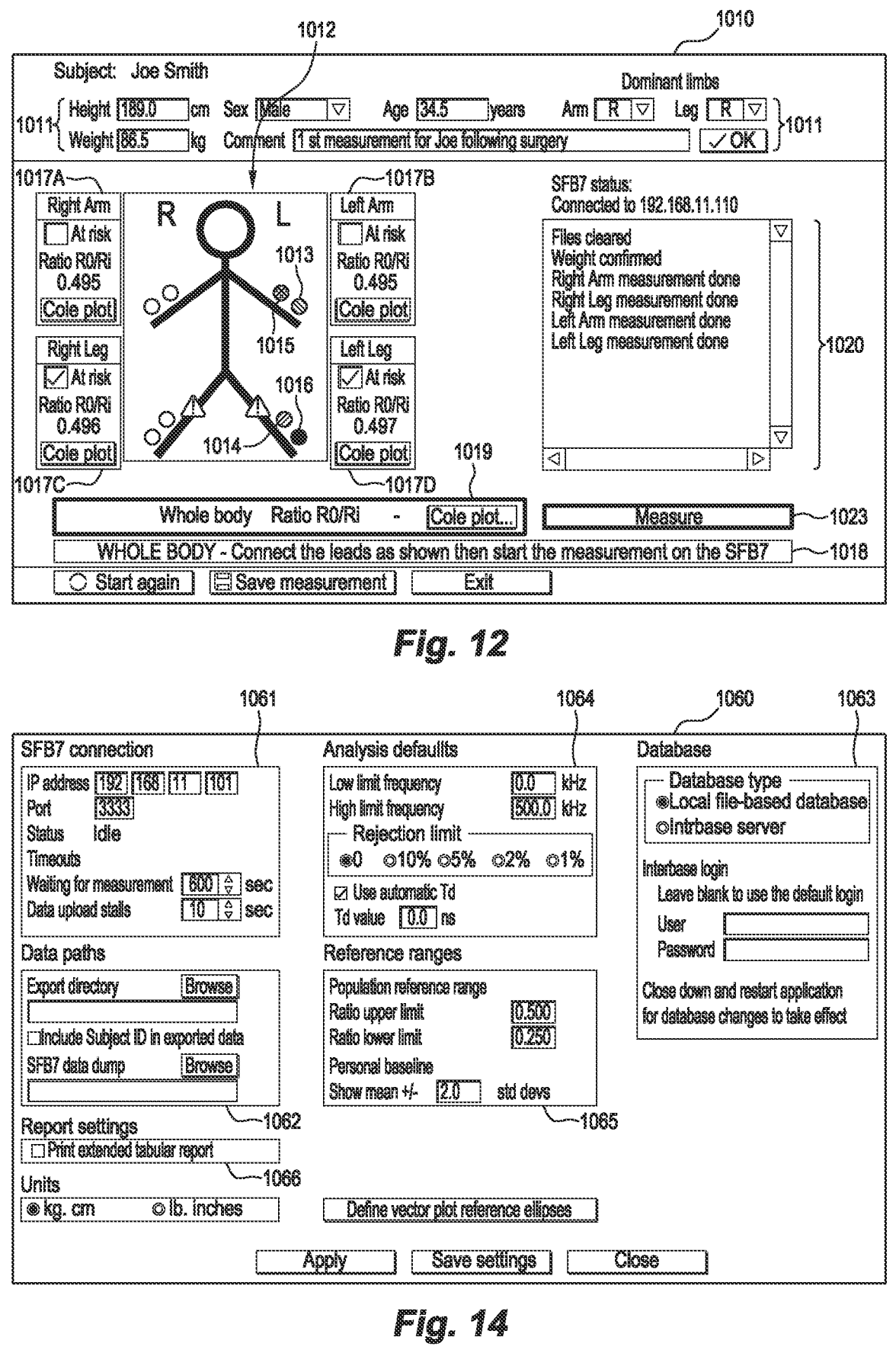

Thus, for example, by positioning the electrodes as shown in FIG. 12, this allows impedance measurements across the subject's entire body to be determined. This in turn allows information such as the subject's total body water (TBW) to be derived. In particular, TBW is given by:

$$TBW = ecf + icf \quad (4)$$

where:
TBW=total body water
ecf=volume of extracellular fluid
icf=volume of intracellular fluid In this regard, the volumes of extracellular and intracellular fluid can be derived from the values $R_0$, $R_\infty$, as these depend on the values of the extracellular and intracellular resistance, as discussed above.

The TBW can be used in:
body composition analysis
derivation of Fat Free Mass (FFM), which can in turn be used as an index of left ventricular mass;
monitoring the build up of fluid in the body of cardiac patients, which can be used as an indicator of right ventricular failure.

Furthermore, by subtracting measured impedance values obtained for each limb from the corresponding impedance values obtained for the entire body, this can be used to derive effective thoracic cavity impedance values. These values can in turn be used as indicators for pulmonary oedema, and hence left ventricular failure, as well as determining cardiac output.

Thus, it will be appreciated that measurement profiles can be determined to allow measurement of
Cardiac parameters;
Pulmonary oedema;
Lymphoedema;
Body composition; and,
Total body water.

Remote Computer System

The above examples have been described on the basis of the selection of the preferred impedance measurements and analysis being performed by a first processing system 10 provided as part of the measuring device 1. However, this is not essential and that any or all of the functionality described could be performed by a processing system that is remotely located to the measuring device 1, as will now be described with respect to FIG. 13.

In this example, a base station 1300 is coupled to a number of measuring devices 1, and a number of end stations 1303 via a communications network 1302, such as the Internet, and/or via communications networks 1304, such as local area networks (LANs), or wide area networks (WANs). The end stations 1303 may also be coupled to measuring devices 1, as shown. The end station 1303 may be any form of end station but is typically a desktop, laptop, tablet, PDA, Smart Phone or the like.

The base station 1300 includes a processing system 1310, coupled to a database 1311. This allows the base station 1300 to be used to update the measuring devices 1, as will be described in more detail below.

In this example, the measuring devices 1 can be connected via the external interface 23, directly to the end stations 1303, or via one of the networks 1302, 3104. This may be achieved via a wired, or wireless connection, depending on the nature of the external interface 23, the end stations 1303, and the networks 1302, 1304.

In this example, the end station 1303 can be used to control the measuring device 1 to perform the measurement procedure. The measuring device 1 therefore operates to generate required excitation signals, apply these to the subject, and measure the resulting voltages generated across the subject. Once impedance measurements have been collected, these are transferred via the external interface 23 to the end station 1303, which operates to analyse the measured impedance values and generate the appropriate GUIs shown in FIGS. 8 to 11.

In this instance, the operator of the system is generally required to place the measuring device 1 in a predetermined operating mode allowing the end station 1303 to generate any required control signals to activate the measurement process.

The measuring device 1 will therefore typically operate to perform single measurements at a given time. In this instance, the end station 1303 will display the next electrode configuration to be used to the operator. The operator will connect the electrodes, 13, 14, 15, 16 to the subject, in the displayed arrangement, and then indicate to the end station 1303 when this has been completed. The end station 1303 will then transfer a control signal to the measuring device 1 causing the next measurement to be performed.

As the measuring device 1 may be capable of operating in modes that perform sequences of measurements, the end station 1303 can implement a measurement-halt check. During this process if the end station 1303 detects measurements within a predetermined time interval, such as 5 seconds, the end station 1303 generates an alert indicating that the measuring device 1 is not provided in single measurement mode, and that this should be adjusted.

It will be appreciated that in this example, the end station 1303 can effectively perform the tasks to performed by the first processing system 10 in the examples throughout the specification. Accordingly, the device could be provided without the first processing system 10, with the functionality usually performed by the first processing system 10 being performed by an end station 1303. In this arrangement, the end station 1303 therefore effectively forms part or all of the first processing system 10. This allows the measuring device 1 to be provided including only the second processing system 17 coupled directly to the external interface 23 to allow the measuring device 1 to be controlled by the end station 1303. This would typically be achieved via the use of suitable applications software installed on the end station 1303.

In this example, communication between the end station 1303 and the measuring device 1 is typically controlled using the GUI 1060 shown in FIG. 14.

The GUI includes fields 1061 for defining IP connection details, which allows the end station 3 to connect to the measuring device 1, via the external interface 23, via a TCP/IP or other network. Fields 1062 are used for defining paths via which the references can be obtained, with the fields 1063 defining details of the database from which the references should be obtained.

Fields 1064 and 1065 are used to define parameters relating to the impedance analysis to be performed, including default frequency, rejection and time delay limits, as well as reference ranges or the like. Finally fields 1066 are used to define properties of the resulting analysis report.

It will therefore be appreciated from this that GUI can also be used to provide connections to remote databases, such as HL7 compliant subject databases. Furthermore, the architecture can be implemented in any one of a number of manners depending on the circumstances in which the measuring device 1 is to be used.

Thus, for example, as a further alternative, the selection and/or analysis of the impedance measurements can be performed by a central base station coupled to a number of measuring devices via a suitable communications system, such as a computer network or the like. In this instance, once the base station has selected an impedance measurement type to be performed, the base station transfers an indication of this to the respective monitoring thereby causing the measuring device 1 to display the necessary electrode connections. Once the impedance measurements have been performed, the determined measurements are returned to the base station for analysis.

Device Updates

Figure 15:
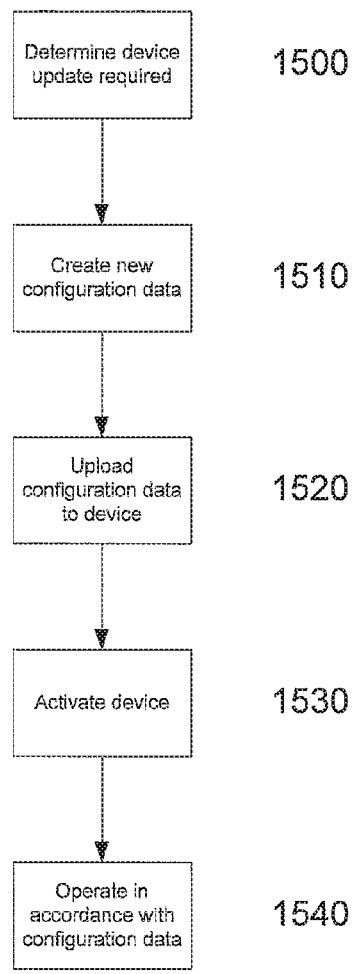
FIG. 15 is a flow chart of an overview of an example of the process of updating a measuring device.

An example of a process for updating the measuring device will now be described with reference to FIG. 15.

In one example, at step 1500 the process involves determining a measuring device 1 is to be configured with an upgrade, or the like, before configuration data is created at step 1510. At step 1520 the configuration data is typically uploaded to the device or the end station 1303 before the device is activated at 1530, or applications software on the end station 1303 is executed. At 1540 when the device commences operation the processing system 2 uses the configuration data to selectively activate features, either for example by controlling the upload of instructions, or by selectively activating instructions embedded within the processing system 2 or the controller 19. Features within applications software installed on the end station 1303 can be activated in a similar manner.

The remaining examples will focus on the updating of the device itself, and it will be appreciated that similar techniques could be implemented for updating software applications in the end station 1303.

Updating can be achieved in one of two ways. For example, the configuration data could consist of instructions, such as a software or firmware, which when implemented by the processing system 2 causes the feature to be implemented. Thus, for example, this process may be utilised to update the operation of the firmware provided in the second processing system 17, the processing system 10 or the controller 19 to allow additional functionality, improved measuring algorithms, or the like, to be implemented.

Alternatively, the configuration data could be in the form of a list of features, with this being used by the processing system 2 to access instructions already stored on the measuring device 1. Utilisation of configuration data in this manner, allows the measuring device to be loaded with a number of as yet additional features, but non-operational features, when the device is sold. In this example, by updating the configuration data provided on the measuring device 1, this allows these further features to be implemented without requiring return of the measuring device 1 for modification.

This is particularly useful in the medical industry as it allows additional features to be implemented when the feature receives approval for use. Thus, for example, techniques may be available for measuring or detecting lymphoedema in a predetermined way, such as through the use of a particular analysis of measured voltage signals or the like. In this instance when a device is sold, approval may not yet have been obtained from an administering body such as the Therapeutic Goods Administration, or the like. Accordingly, the feature is disabled by appropriate use of a configuration data. When the measurement technique subsequently gains approval, the configuration data can be modified by uploading a new updated configuration data to the measuring device, allowing the feature to be implemented.

It will be appreciated that these techniques may be used to implement any one of a number of different features, such as different measuring techniques, analysis algorithms, reports on results of measured impedance parameters, or the like.

Figure 13:
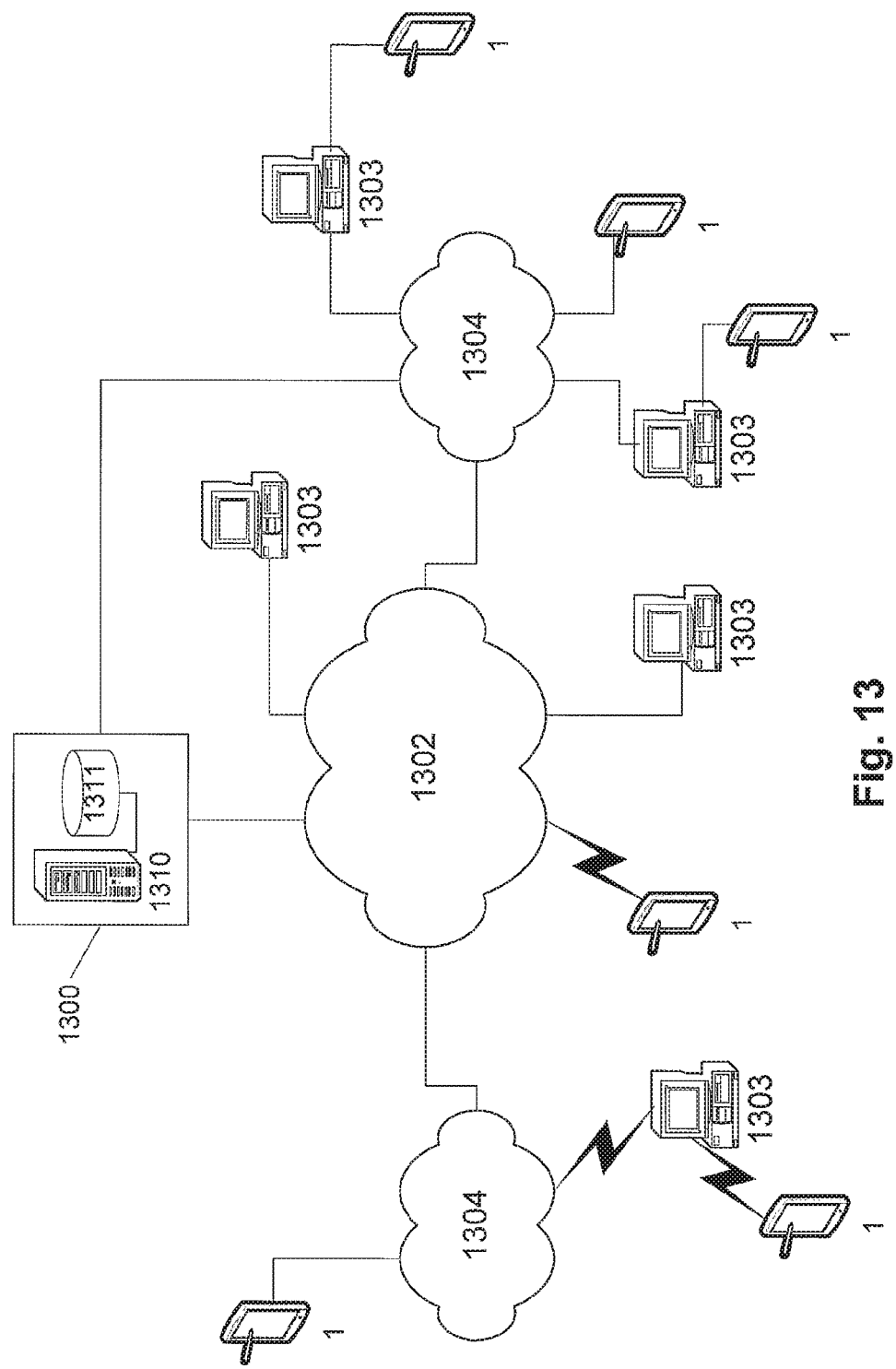
FIG. 13 is a schematic diagram of an example of a system architecture for updating a measuring device.

This can be achieved using the system of FIG. 13. In use, the base station 1300 includes a processing system 1310, coupled to a database 1311. The base station 1300 operates to determine when updates are required, select the devices to which updates are applied, generate the configuration data and provide this for update to the devices 1. It will be appreciated that the processing system 1310 may therefore be a server or the like.

This allows the configuration data to be uploaded from the server either to a user's end station 1303, such as a desk top computer, lap top, Internet terminal or the like, or alternatively allows transfer from the server via the communications network 1302, 1304, such as the Internet. It will be appreciated that any suitable communications system can be used such as wireless links, wi-fi connections, or the like.

Figure 16:
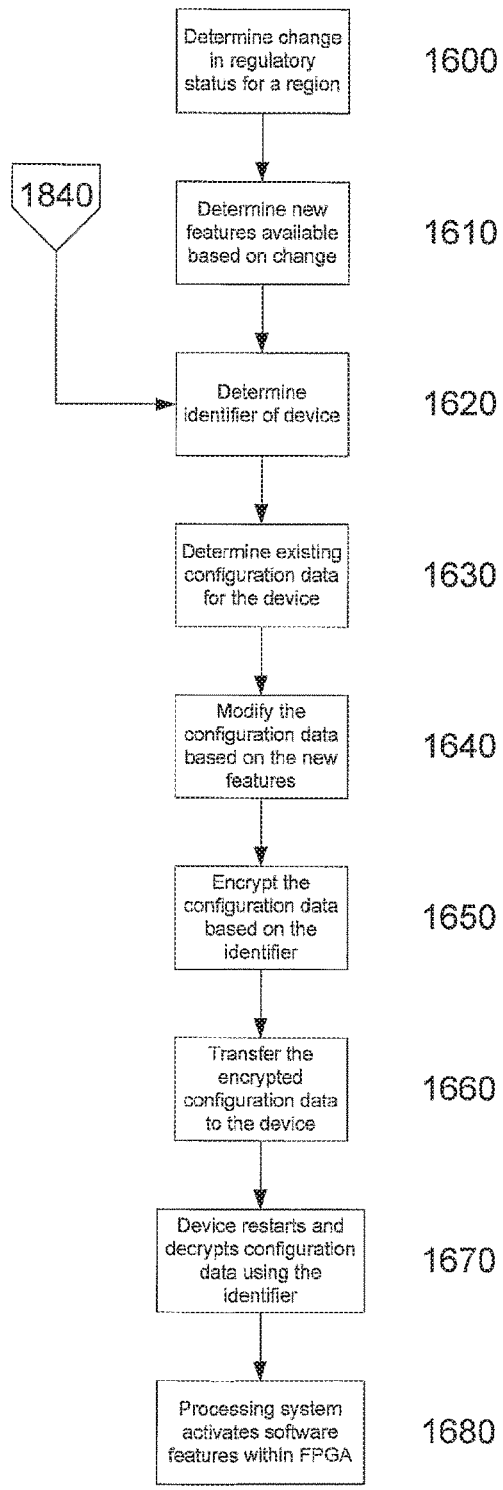
FIG. 16 is a flow chart of a first example of the process of updating a measuring device; and, FIG. 17 is a flow chart of a second example of the process of updating a measuring device.

In any event, an example of the process of updating the measuring device 1 will now be described in more detail with reference to FIG. 16. In this example, at step 1600 the base station 1300 determines that there is a change in the regulatory status of features implemented within a certain region. As mentioned above this could occur for example following approval by the TGA of new features.

The base station 1300 uses the change in regulatory status to determine new features available at step 1610, before determining an identifier associated with each measuring device 1 to be updated at step 1620. As changes in regulatory approval are region specific, this is typically achieved by having the base station 1300 access database 1311 including details of the regions in which each measuring device sold are used. The database 1311 includes the identifier for each measuring device 1, thereby allowing the identifier of each measuring device to be updated to be determined.

At step 1630, the base station 1300 determines the existing configuration data, typically from the database 1311, for a next one of the measuring devices 1, before modifying the configuration data to implement the new features at step 1640. The configuration data is then encrypted utilising a key associated with the identifier. The key may be formed from a unique prime number associated with the serial number, or partially derived from the serial number, and is typically stored in the database 1311, or generated each time it is required using a predetermined algorithm.

At step 1660 the encrypted configuration data is transferred to the measuring device 1 as described above.

At step 1670 when the device restarts and the first processing system 10 is activated, the first processing system 10 determines the encryption key, and uses this to decrypt the configuration data. This may be achieved in any one of a number of ways, such as by generating the key using the serial number or other identifier, and a predetermined algorithm. Alternatively, this may be achieved by accessing a key stored in the memory 21. It will be appreciated that any form of encryption may be used, although typically strong encryption is used, in which a secret key is used to both encrypt and decrypt the configuration data, to thereby prevent fraudulent alteration of the configuration by users, as will be explained in more detail below.

At step 1680, the first processing system 10 activates software features within the second processing system 16 using the decrypted configuration data.

It will therefore be appreciated that this provides a mechanism for automatically updating the features available on the measuring device. This may be achieved either by having the second processing system 16 receive new firmware from the processing system 10, or by activating firmware already installed on the second processing system 16, as described above.

As an alternative to performing this automatically when additional features are approved for use, the process can be used to allow features to be activated on payment of a fee. In this example, a user may purchase a measuring device 1 with limited implemented functionality. By payment of a fee, additional features can then be activated as and when required by the user.

Figure 17:
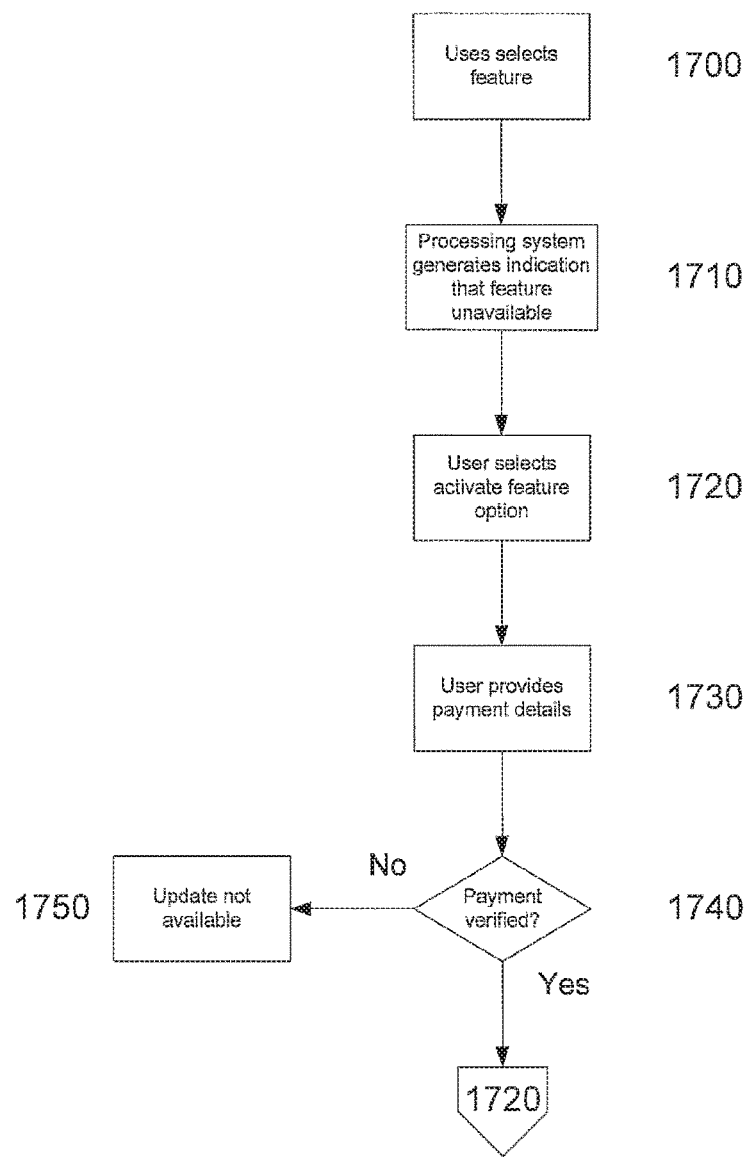

In this example, as shown in FIG. 17, when the user selects an inactive feature at step 1700, the first processing system 10 will generate an indication that the feature is unavailable at step 1710. This allows the user to select an activate feature option at step 1720, which typically prompts the user to provide payment details at step 1730. The payment details are provided to the device manufacturer in some manner and may involve having the user phone the device manufacturer, or alternatively enter the details via a suitable payment system provided via the Internet or the like.

At step 1740, once the payment is verified, the process can move to step 1620 to allow an automatic update to be provided in the form of a suitable configuration data. However, if payment details are not verified the process ends at 1750.

It will be appreciated by a person skilled in the art that encrypting the configuration data utilising a unique identifier means that the configuration data received by a measuring device 1 is specific to that measuring device. Accordingly, the first processing system 10 can only interpret the content of a configuration data if it is both encrypted and decrypted utilising the correct key. Accordingly, this prevents users exchanging configuration data, or attempting to re-encrypt a decrypted file for transfer to a different device.

It will be appreciated that in addition to, or as an alternative to simply specifying features in the configuration data, it may be necessary to upload additional firmware to the second processing system 16. This can be used for example, to implement features that could not be implemented using the firmware shipped with the measuring device 1.

In this example, it would be typical for the configuration data to include any required firmware to be uploaded, allowing this to be loaded into the second processing system 16, using the first processing system 10. This firmware can then either be automatically implemented, or implemented in accordance with the list of available features provided in the configuration data.

It will be appreciated that this provides a mechanism for updating and/or selectively activating or deactivating features, such as measuring protocols, impedance analysis algorithms, reports interpreting measured results, or the like. This can be performed to ensure the measuring device conforms to existing TGA or FDA approvals, or the like.

Throughout the above examples, the end station 1303 can be used to download configuration data, or alternatively transfer instructions to any one of the processing systems 2, 10, 17, 19 used by the measuring device 1, to allow updating of the device operation.

Persons skilled in the art will appreciate that numerous variations and modifications will become apparent. All such variations and modifications which become apparent to persons skilled in the art, should be considered to fall within the spirit and scope that the invention broadly appearing before described.

Thus, for example, it will be appreciated that features from different examples above may be used interchangeably where appropriate. Furthermore, whilst the above examples have focussed on a subject such as a human, it will be appreciated that the measuring device and techniques described above can be used with any animal, including but not limited to, primates, livestock, performance animals, such race horses, or the like.

The above described processes can be used for diagnosing the presence, absence or degree of a range of conditions and illnesses, including, but not limited to oedema, lymphoedema, body composition, or the like.

What is claimed is:

1. An apparatus configured to perform impedance measurements on a subject, the apparatus including:
   a measuring device configured to perform impedance measurements, the measuring device comprising:
   a signal generator coupled to respective electrodes in use, the signal generator configured to apply an alternating current signal to the subject; and
   a voltage sensor coupled to respective electrodes in use, the sensor configured to sense voltage signals across the subject, the measuring device configured to digitize and sample the voltage and current signals across the subject to allow the voltage and current signals to be used to determine impedance values;
   a processing system connected to the measuring device via a wireless connection, the processing system configured to:
   retrieve a selected one of a plurality of impedance profiles from a memory, the plurality of impedance profiles representing different impedance measurement types having different impedance analysis such that each of the plurality of impedance profiles corresponds to at least one impedance analysis which is unique among the plurality of impedance profiles;
   receive data representing the measured impedance values;
   determine, from the selected one of the plurality of impedance profiles, instructions required to perform at least one impedance analysis corresponding to the selected one of the plurality of impedance profiles;
   perform an analysis of the measured impedance values, in accordance with the determined instructions; and
   generate a representation of results of the analysis, wherein the steps of performing the analysis and generating the representation are performed in accordance with the one or more impedance measurement types in the retrieved impedance profile; and wherein the different impedance profiles are used to analyse the impedance values to determine at least one of:
   one or more parameters relating to dialysis;
   one or more parameters relating to cardiac function;
   the presence, absence or degree of oedema;
   the presence, absence or degree of pulmonary oedema; and
   the presence, absence or degree of lymphoedema.

2. The apparatus of claim 1, wherein the processing system is further configured to:
   determine a processing operation based on the impedance measurement type; and process the measured impedance values in accordance with the determined processing operation.

3. The apparatus of claim 1, wherein the processing system is further configured to:
select a representation type based on the impedance measurement type; and
generate the representation in accordance with the selected representation type.

4. The apparatus of claim 1, wherein the processing system is further configured to:
display an indication of available impedance measurement types, the available impedance measurement types being retrieved from memory and based on the retrieved impedance profile that provides instructions to allow the measuring device to perform required impedance measurements; and
determine the impedance measurement type based on an available impedance measurement type selected in accordance with input commands from an operator.

5. The apparatus of claim 1, wherein the processing system is further configured to:
determine at least one electrode arrangement associated with the impedance profile;
display a representation indicative of the electrode arrangement including;
the position of a set of electrodes; and
lead connections between the processing system and a number of the set of electrodes;
receive input commands indicating that the electrodes are arranged in accordance with the displayed arrangement; and
cause an impedance measurement to be performed in accordance with the received input command.

6. The apparatus of claim 5, wherein the processing system is further configured to:
determine a sequence of impedance measurements for the impedance profile; and,
generate a sequence of representations, each representation defining a respective electrode arrangement for performing a respective measurement.

7. The apparatus of claim 1, wherein the processing system is further configured to
cause at least one measurement to be performed in accordance with the selected one of the plurality of impedance measurement profiles.

8. The apparatus of claim 1, wherein the processing system is coupled to the measuring device and the processing system is further configured to:
cause the measuring device to perform the impedance measurements; and
analyze impedance values transferred from the measuring device.

9. The apparatus of claim 8, wherein:
the processing system is further configured to:
generate instructions; and
transfer the instructions to the measuring device; and
the measuring device is responsive to the instructions to cause the impedance measurements to be performed.

10. The apparatus of claim 1, wherein the processing system is further configured to:
determine at least one subject parameter relating to the subject; and
at least one of:
determine the impedance measurement type in accordance with the determined at least one subject parameter; and
process at least one measured impedance value in accordance with the determined at least one subject parameter.

11. The apparatus of claim 10, wherein the subject parameter is at least one of:
an indication of a presence, absence or degree of a condition;
an indication of an intervention;
an indication of a body segment at risk of a condition;
age;
height;
weight; and
sex.

12. The apparatus of claim 10, wherein the processing system is further configured to:
determine a unique identifier indicative of an identity of the subject; and
determine the at least one subject parameter from a remote database using the unique identifier.

13. The apparatus of claim 1, wherein the processing system is further configured to:
determine whether a reference value is available; and
at least one of:
determine the impedance measurement type depending on whether the reference value is available; and,
processes at least one measured impedance value depending on whether the reference value is available.

14. The apparatus of claim 1, wherein the processing system is further configured to:
receive configuration data indicative of at least one feature from at least one of a computer system and a communications network;
determine, using the configuration data, instructions representing the at least one feature; and
using the instructions, at least one of:
cause impedance measurements to be performed; and
perform analysis of impedance measurements.

15. The apparatus of claim 14, wherein the processing system includes first and second processing systems, and wherein:
the first processing system selects the instructions using the configuration data; and,
the second processing system causes impedance measurements to be performed using selected instructions.

16. The apparatus of claim 14, wherein the processing system is further configured to:
determine if a feature selected by a user is available;
if the feature is not available, determine if the user wishes to enable the feature; and
if the user wishes to enable the feature, cause configuration data to be received.

17. The apparatus of claim 16, wherein the processing system is further configured to:
cause the user to provide a payment to a device provider; and,
receive the configuration data in response to payment.

18. The apparatus of claim 1, wherein the voltage sensor includes a buffer circuit configured to filter and amplify voltages at the electrodes.

19. The apparatus of claim 1, wherein the retrieved impedance profile defines at least one of:
one or more of impedance measurement types;
one or more measurement procedures; and
one or more measurement sequences.

20. The apparatus of claim 1, wherein the at least one impedance analysis corresponding to the selected one of the plurality of impedance profiles comprises the calculation of an indicator value related to the selected one of the plurality of impedance profiles.

* * * * *